United States Patent
Hastings et al.

(10) Patent No.: US 10,370,667 B2
(45) Date of Patent: *Aug. 6, 2019

(54) ANTISENSE COMPOUNDS TARGETING LEUCINE-RICH REPEAT KINASE 2 (LRRK2) FOR THE TREATMENT OF PARKINSONS DISEASE

(71) Applicants: Rosalind Franklin University of Medicine and Science, North Chicago, IL (US); The McLean Hospital Corporation, Belmont, MA (US)

(72) Inventors: Michelle L. Hastings, North Chicago, IL (US); Ole Isacson, Belmont, MA (US); Joanna A. Korecka-Roet, Belmont, MA (US)

(73) Assignees: Rosalind Franklin University Of Medicine And Science, North Chicago, IL (US); The McLean Hospital Corporation, Belmont, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/837,926

(22) Filed: Dec. 11, 2017

(65) Prior Publication Data
US 2018/0094266 A1  Apr. 5, 2018

Related U.S. Application Data

(63) Continuation-in-part of application No. 15/349,840, filed on Nov. 11, 2016, now Pat. No. 9,840,710.

(60) Provisional application No. 62/257,109, filed on Nov. 18, 2015.

(51) Int. Cl.
| | | |
|---|---|---|
| A61K 48/00 | (2006.01) | |
| C07H 21/02 | (2006.01) | |
| C07H 21/04 | (2006.01) | |
| C12N 15/113 | (2010.01) | |

(52) U.S. Cl.
CPC .. *C12N 15/1137* (2013.01); *C12Y 207/11001* (2013.01); *C12N 2310/11* (2013.01); *C12N 2310/315* (2013.01); *C12N 2310/3231* (2013.01); *C12N 2310/3233* (2013.01); *C12N 2310/346* (2013.01); *C12N 2320/33* (2013.01)

(58) Field of Classification Search
CPC .......................... A61K 31/713; C12N 15/113
See application file for complete search history.

(56) References Cited

U.S. PATENT DOCUMENTS

| | | | |
|---|---|---|---|
| 5,142,047 A | 8/1992 | Summerton et al. | |
| 5,185,444 A | 2/1993 | Summerton et al. | |
| 5,780,241 A | 7/1998 | Cook | |
| 5,837,449 A | 11/1998 | Monia et al. | |
| 6,001,992 A | 12/1999 | Ackermann et al. | |
| 6,015,712 A | 1/2000 | Monia et al. | |
| 6,133,246 A | 10/2000 | McKay et al. | |
| 6,172,216 B1 | 1/2001 | Bennett et al. | |
| 6,177,246 B1 | 1/2001 | Monia et al. | |
| 6,214,986 B1 | 4/2001 | Bennett et al. | |
| 6,800,444 B1 | 10/2004 | Cook et al. | |
| 6,809,193 B2 | 10/2004 | McKay et al. | |
| 7,425,545 B2 | 9/2008 | Crooke et al. | |
| 7,846,730 B2 | 12/2010 | Zhang et al. | |
| 7,863,252 B2 | 1/2011 | Crooke et al. | |
| 8,669,102 B2 | 3/2014 | Bennett et al. | |
| 8,859,514 B2 | 10/2014 | Crooke et al. | |
| 8,957,040 B2 | 2/2015 | Bennett et al. | |
| 2003/0144221 A1 | 7/2003 | Zhang et al. | |
| 2003/0225256 A1 | 12/2003 | Watt | |
| 2003/0235913 A1 | 12/2003 | Dobie | |
| 2004/0005705 A1 | 1/2004 | Bennett et al. | |
| 2004/0110142 A1 | 6/2004 | Bennett et al. | |
| 2004/0116364 A1 | 6/2004 | Dobie | |
| 2005/0130923 A1 | 6/2005 | Bhat et al. | |
| 2011/0098340 A1 | 4/2011 | Zhang et al. | |
| 2011/0230544 A1 | 9/2011 | Crooke et al. | |
| 2011/0269818 A1 | 11/2011 | Bennett et al. | |
| 2012/0135941 A1 | 5/2012 | Collard et al. | |
| 2013/0046007 A1 | 2/2013 | Bennett et al. | |
| 2014/0005252 A1 | 1/2014 | Bennett et al. | |
| 2014/0128322 A1 | 5/2014 | Chen et al. | |

(Continued)

FOREIGN PATENT DOCUMENTS

| | | |
|---|---|---|
| WO | 2007/134181 | 11/2007 |
| WO | 2007/135426 A2 | 11/2007 |

(Continued)

OTHER PUBLICATIONS

Aartsma-Rus & Van Ommen, "Antisense-mediated exon skipping: A versatile tool with therapeutic and research applications" RNA 13(10):1609-24 (Oct. 2007).

Cooper et al., "Differentiation of human ES and Parkinson's disease iPS cells into ventral midbrain dopaminergic neurons requires a high activity form of SHH, FGF8a and specific regionalization by retinoic acid," Molecular and Cellular Neuroscience 45(3):258-66 (Nov. 2010).

Cooper et al., "Pharmacological Rescue of Mitochondrial Deficits in iPSC-Derived Neural Cells from Patients with Familial Parkinson's Disease," Sci Transl Med. 4(141):141ra90 (Jul. 2012).

(Continued)

*Primary Examiner* — Amy H Bowman
(74) *Attorney, Agent, or Firm* — McDonnell Boehnen Hulbert & Berghoff LLP

(57) ABSTRACT

The present disclosure relates generally to compounds comprising oligonucleotides complementary to a Leucine-Rich-Repeat-Kinase (LRRK2) RNA transcript. Certain such compounds are useful for hybridizing to a LRRK2 RNA transcript, including but not limited to a LRRK2 RNA transcript in a cell. In certain embodiments, such hybridization results in modulation of splicing of the LRRK2 transcript. In certain embodiments, such compounds are used to treat one or more symptoms associated with Parkinson's disease.

16 Claims, 89 Drawing Sheets

Specification includes a Sequence Listing.

(56) References Cited

U.S. PATENT DOCUMENTS

| | | | |
|---|---|---|---|
| 2014/0303235 | A1 | 10/2014 | Oestergaard et al. |
| 2014/0309279 | A1 | 10/2014 | Oestergaard et al. |
| 2014/0323707 | A1 | 10/2014 | Seth et al. |
| 2015/0051389 | A1 | 2/2015 | Seth et al. |
| 2015/0275205 | A1 | 10/2015 | Miller et al. |
| 2015/0275208 | A1 | 10/2015 | Oestergaard et al. |
| 2015/0329859 | A1 | 11/2015 | Bennett et al. |
| 2015/0376625 | A1 | 12/2015 | Oestergaard et al. |
| 2016/0138014 | A1 | 5/2016 | Kordasiewicz et al. |

FOREIGN PATENT DOCUMENTS

| | | | | |
|---|---|---|---|---|
| WO | | 2008/101157 | 8/2008 | |
| WO | | 2011/114106 A2 | 9/2011 | |
| WO | WO | 2012/087756 A1 | 6/2012 | |
| WO | | 2012/131365 A1 | 10/2012 | |
| WO | WO | 2012/131365 | * 10/2012 | ........... C12N 15/113 |
| WO | | 2013/022984 A1 | 2/2013 | |
| WO | | 2013/022990 A1 | 2/2013 | |
| WO | | 2013/148260 A1 | 10/2013 | |
| WO | | 2013/148283 A1 | 10/2013 | |
| WO | | 2014/036301 A1 | 3/2014 | |
| WO | | 2014/059356 A2 | 4/2014 | |
| WO | | 2014/121287 A2 | 8/2014 | |
| WO | | 2014/153236 A1 | 9/2014 | |
| WO | | 2015/010135 A2 | 1/2015 | |
| WO | | 2015/084884 A2 | 6/2015 | |
| WO | | 2015/143245 A1 | 9/2015 | |
| WO | | 2015/143246 A1 | 9/2015 | |
| WO | | 2015/168172 A1 | 11/2015 | |
| WO | | 2015/187989 A1 | 12/2015 | |
| WO | | 2016/019063 A1 | 2/2016 | |
| WO | | 2016/044840 A1 | 3/2016 | |
| WO | | 2016/077837 A1 | 5/2016 | |
| WO | | 2016/097212 A1 | 6/2016 | |
| WO | WO | 2017/087282 A1 | 5/2017 | |

OTHER PUBLICATIONS

Du et al., "Correction of prototypic ATM splicing mutations and aberrant ATM function with antisense morpholino oligonucleotides." PNAS, 104(14):6007-12 (Apr. 2007).
Genetools, "Endo-Porter Delivery of Morpholino Oligos" from Gene Tools, LLC, Sep. 14, 2012, pp. 1-4.
Kabanov et al., "A new class of antivirals: antisense oligonucleotides combined with a hydrophobic substituent effectively inhibit influenza virus reproduction and synthesis of virus-specific proteins in MDCK cells" FEBS Lett, 259:327-330 (Jan. 1990).
Letsinger et al., "Cholesteryl-conjugated oligonucleotides: synthesis, properties, and activity as inhibitors of replication of human immunodeficiency virus in cell culture." Proc. Natl. Acad. Sci. USA, 86(17):6553-6556 (Sep. 1989).
Oberhauser et al., "Effective incorporation of 2'-O-methyl-oligoribonucleotides into liposomes and enhanced cell association through modification with thiocholesterol." Nucl. Acids Res., 20(3):533-538 (Feb. 1992).
Reinhardt et al., "Genetic Correction of a LRRK2 Mutation in Human iPSCs Links Parkinsonian Neurodegeneration to ERK-Dependent Changes in Gene Expression." Cell Stem Cell 12(3):354-67 (Mar. 2013).
Saison-Behmoaras et al., "Short modified antisense oligonucleotides directed against Ha-ras point mutation induce selective cleavage of the mRNA and inhibit T24 cells proliferation." EMBO J., 10(5):1111-18 (May 1991).
Shea et al., "Synthesis, hybridization properties and antiviral activity of lipid-oligodeoxynucleotide conjugates." Nucl. Acids Res., 18(13):3777-83 (Jul. 1990).
Smith et al., "A combinatorial approach to create artificial homing endonucleases cleaving chosen sequences." Nucleic Acids Res. 34(22):e149 (Dec. 2006).

Smith et al., "Fibroblast Biomarkers of sporadic parkinson's disease and LRRK2 kinase inhibition," Mol Neurobiol. 53(8):5161-77 (Oct. 2016; Epub Sep. 23, 2015).
Sunberg et al., "Improved Cell Therapy Protocols for Parkinson's disease based on differentiation efficiency and safety of hESC-, hiPSC-, and non-human primate iPSC-derived dopaminergic neurons," Stem Cells. 31(8):1548-62 (Aug. 2013).
Suzuki et al., "Imaging intraorganellar Ca2+ at subcellular resolution using CEPIA," Nature Communications, 5:4153 (Jun. 2014).
Van Vliet et al., "Assessment of the feasibility of exon 45-55 multiexon skipping for Duchenne muscular dystrophy." BMC Med Genet. 9:105 (Dec. 2008).
Crooke et al., "Pharmacokinetic properties of several novel oligonucleotide analogs in mice." J. Pharmacol. Exp. Ther., 277(2):923-37 (May 1996).
Manoharan et al., "Chemical modifications to improve uptake and bioavailability of antisense oligonucleotides." Ann. N. Y. Acad. Sci., 660:306-309 (Oct. 1992).
Manoharan et al., "Introduction of a lipophilic thioether tether in the minor groove of nucleic acids for antisense applications" Bioorganic & Medicinal Chemistry Letters, 3(12):2765-2770 (Dec. 1993).
Manoharan et al., "Cholic acid-oligonucleotide conjugates for antisense applications" Bioorganic & Medicinal Chemistry Letters, 4(8):1053-1060 (Apr. 1994).
Manoharan et al., "Lipidic nucleic acids" Tetrahedron Letters, 36(21):3651-54 (May 1995).
Manoharan et al., "Oligonucleotide Conjugates: Alteration of the Pharmacokinetic Properties of Antisense Agents" Nucleosides & Nucleotides, 14(Issue 3-5): 969-973 (1995).
Mishra et al., "Improved leishmanicidal effect of phosphorotioate antisense oligonucleotides by LDL-mediated delivery." Biochim. Biophys. Acta, 1264(2):229-237 (Nov. 1995).
Srivastava et al., "Five- and six-membered conformationally locked 2',4'-carbocyclic ribo-thymidines: synthesis, structure, and biochemical studies." J. Am. Chem. Soc. 129(26):8362-8379 (Jul. 2007).
Svinarchuk et al., "Inhibition of HIV proliferation in MT-4 cells by antisense oligonucleotide conjugated to lipophilic groups" Biochimie, 75(1-2):49-54 (1993).
De Ynigo-Mojado et al., "Efficient allele-specific targeting of LRRK2 R1441 mutations mediated by RNAi." PLoS One 6(6):e21353 (Jun. 2011).
Saleh et al., "Chapter 23: Overview of alternative oligonucleotide chemistries for exon skipping." Methods in Molecular Biology 867:365-78 (2012).
Sazani et al., "Therapeutic potential of antisense oligonucleotides as modulators of alternative splicing." Journal of Clinical Investigation 112(4):481-86 (Aug. 2003).
Volta et al., "Chronic and acute LRRK2 silencing has no long-term behavioral effects, whereas wild-type and mutant LRRK2 overexpression induce motor and cognitive deficits and altered regulation of dopamine release." Parkinsonism and Related Disorder, 21(10):1156-63 (Oct. 2015).
Zhao et al., "Antisense oligonucleotides to LRRK2 ameliorate alpha-synuclein pathology and behavioral deficit induced by preformed alpha—synuclein fibrils" Neurology 86(16): Poster Session V 354 (Apr. 2016). Abstract submitted.
The International Search Report for International Application No. PCT/US2016/061664, dated Feb. 24, 2017, pp. 1-7.
Rosado, C.J., et al., "Rosella: A Fluorescent pH-Biosensor for Reporting Vacuolar Turnover of Cytosol and Organelles in Yeast", Autophagy., Feb. 2008, vol. 4(2), pp. 205-213, Epub Nov 21, 2007. (Abstract only).
Smith, G.A., et al., "Fibroblast Biomarkers of Sporadic Parkinson's Disease and LRRK2 Kinase Inhibition", Mol. Neurobiol., Oct. 2016, vol. 53(8), pp. 5161-5177, doi:10.1007/s12035-015-9435-4, Epub Sep. 23, 2015.
van Deutekom, et al., "Local Dystrophin Restoration with Antisense Oligonucleotide PRO051", N Engl J Med, Dec. 2007, vol. 357(26), pp. 2677-2686.
Zhao et al., "LRRK2 Antisense Oligonucleotides Ameliorate alpha-Synuclein Inclusion Formation in a Parkinson's Disease Mouse Model" Molecular Therapy-Nucleic Acids 8(1):508-19 (Sep. 2017).

(56) References Cited

OTHER PUBLICATIONS

The International Search Report for International Application No. PCT/US20181064693; dated Feb. 25, 2019, pp. 1-7.

* cited by examiner

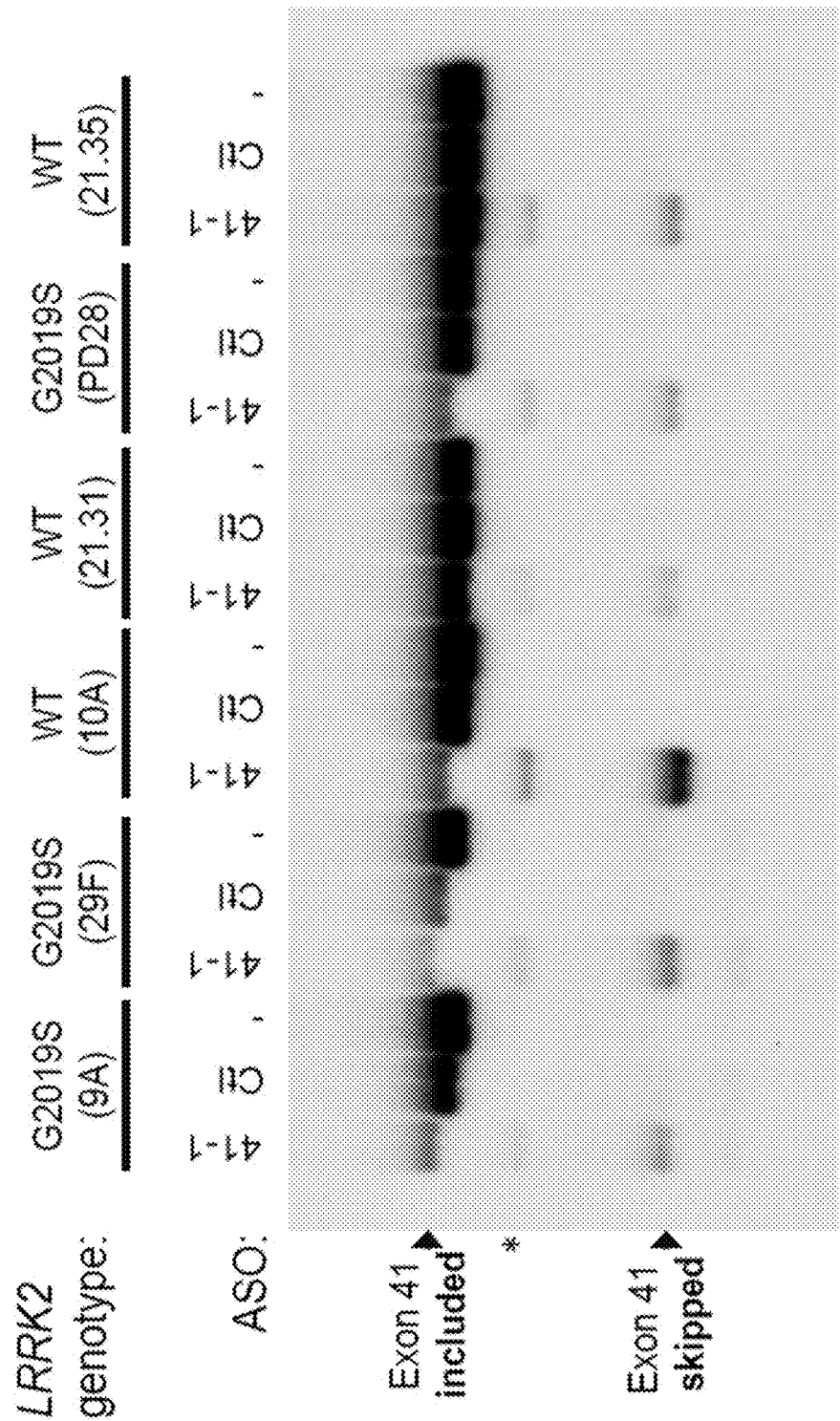

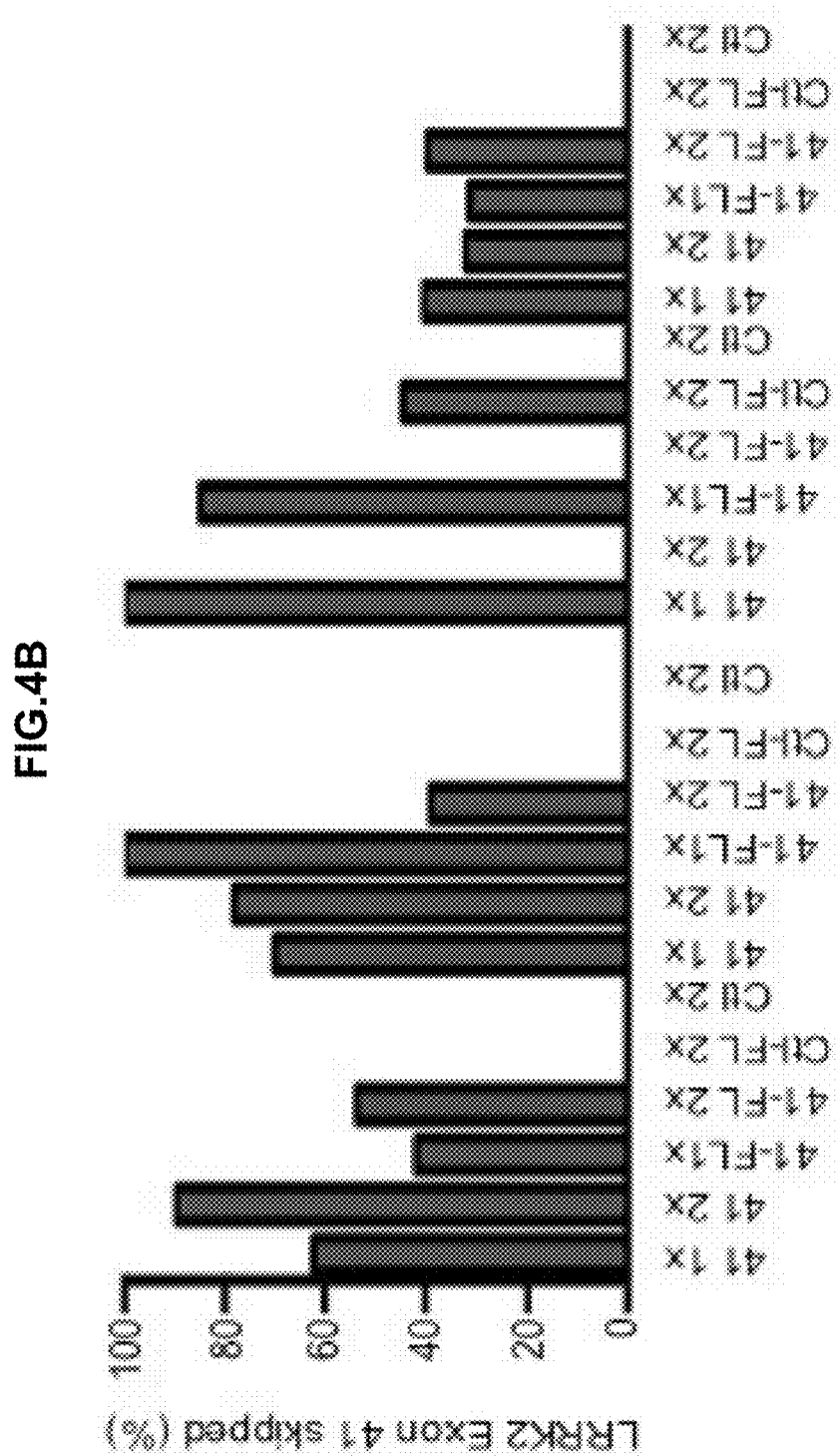

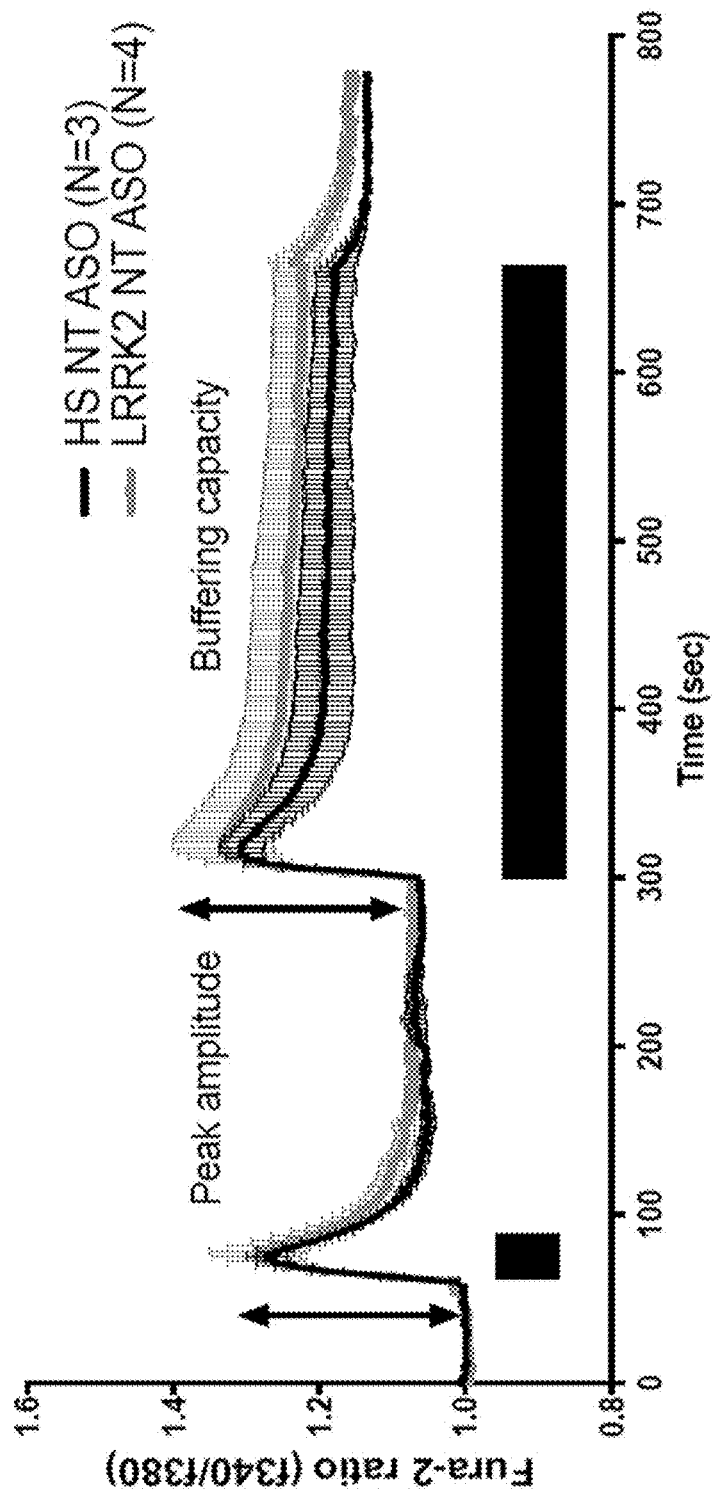

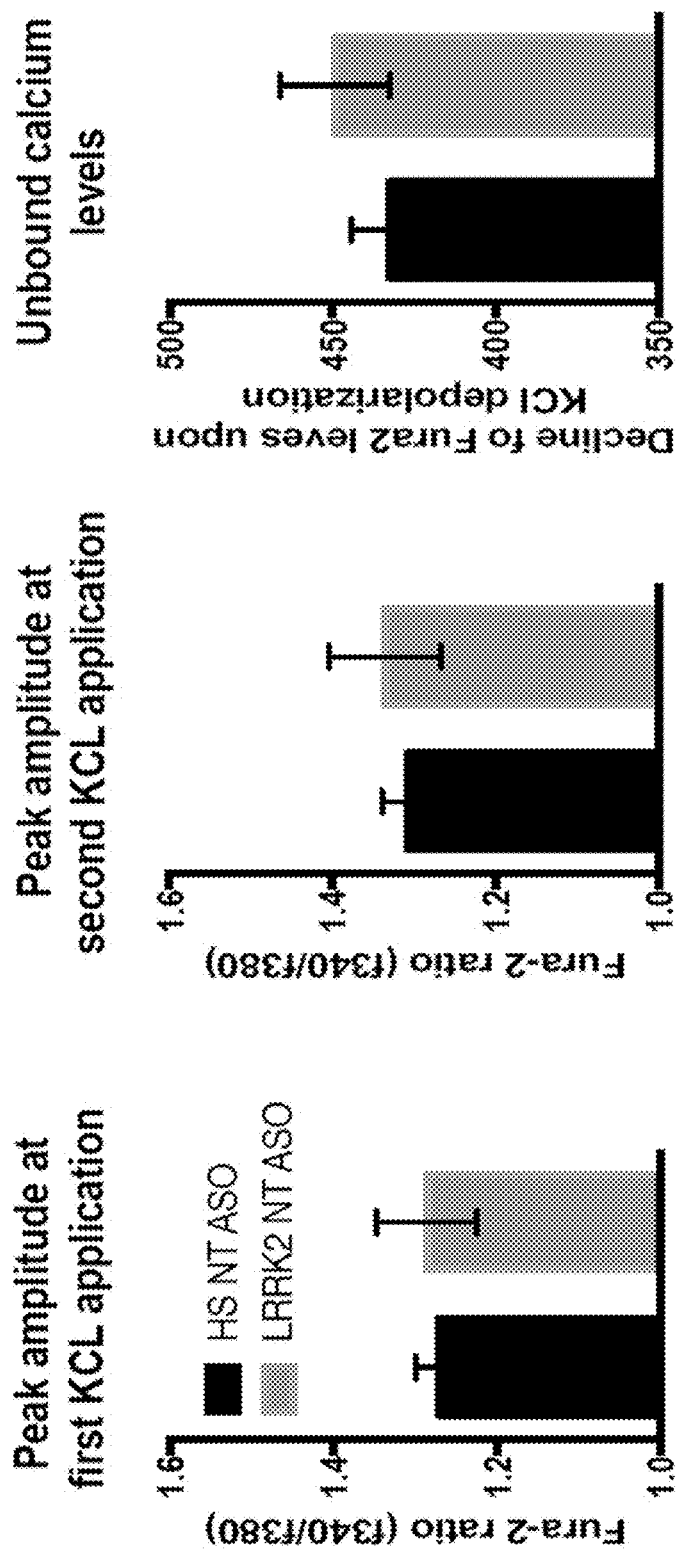

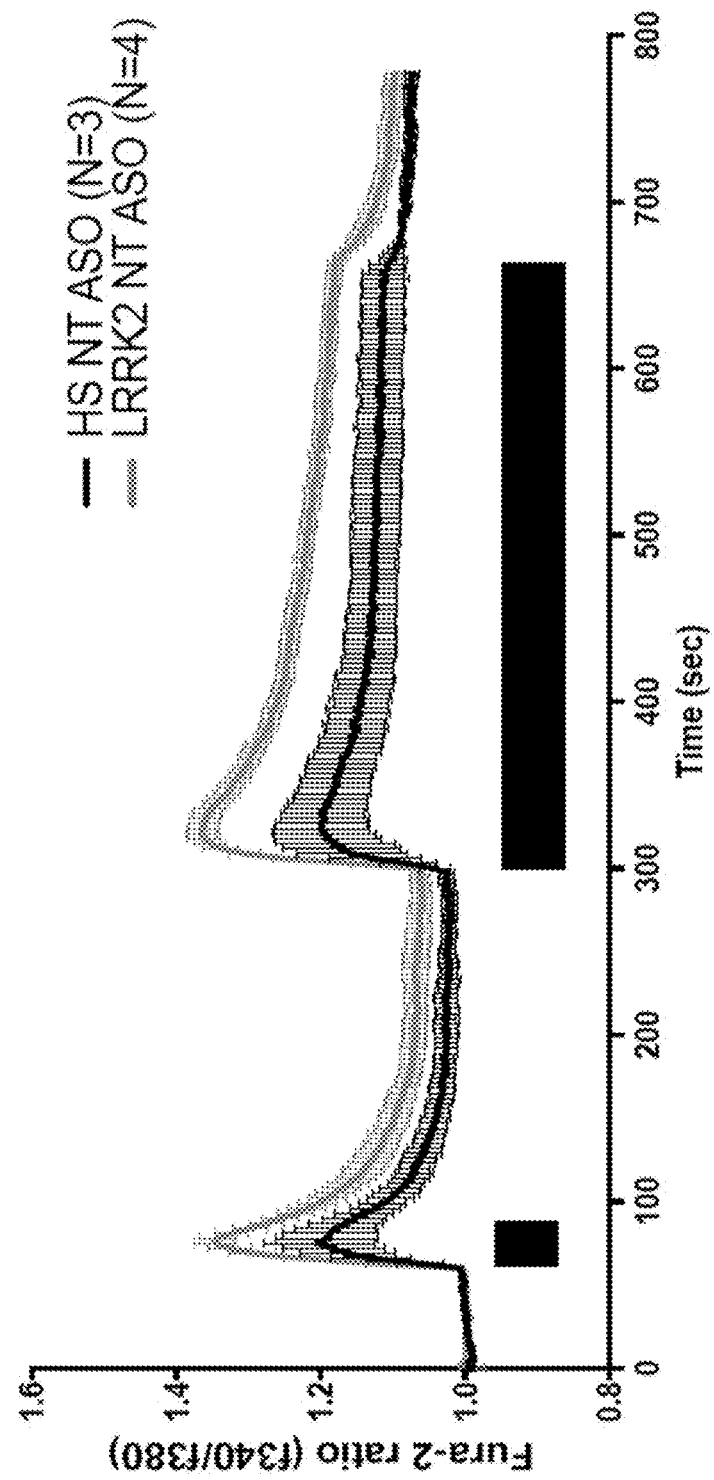

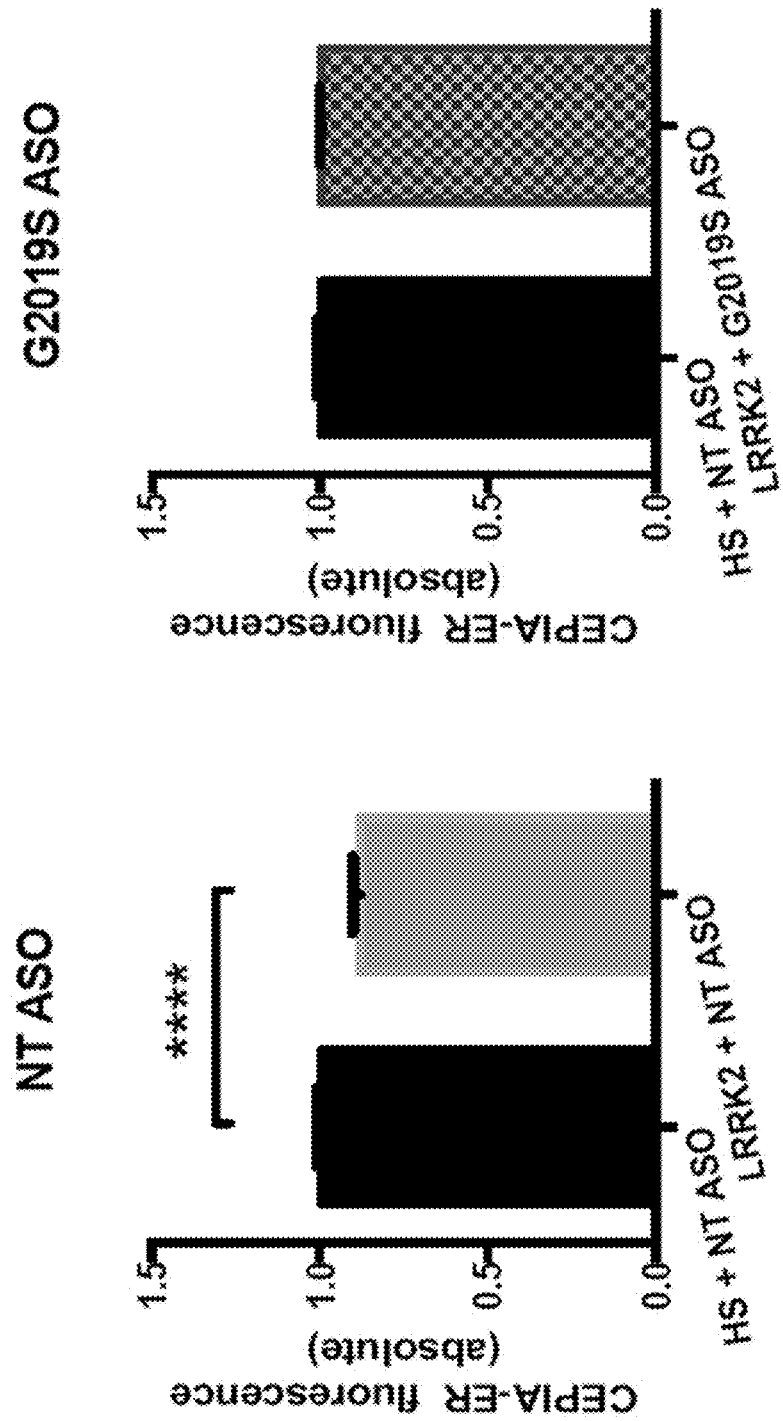

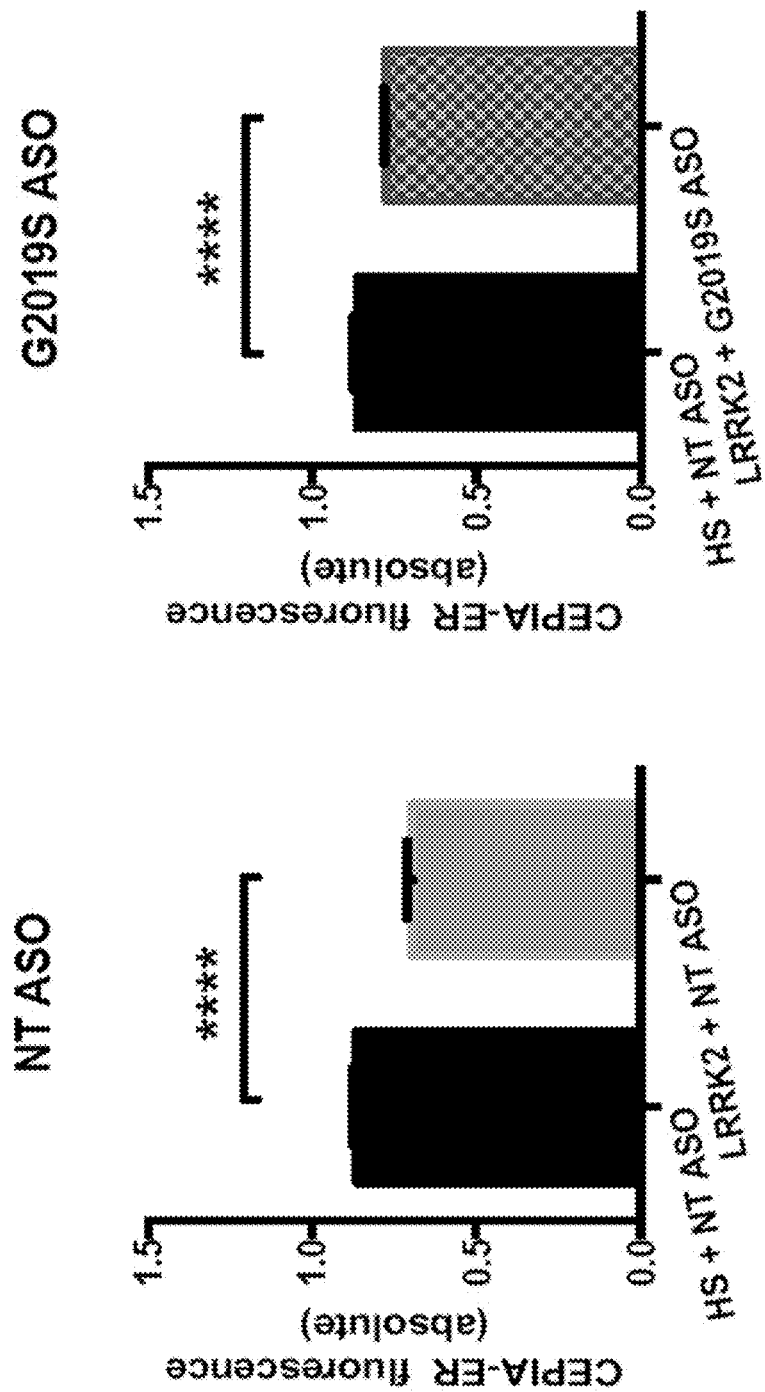

FIG.8C
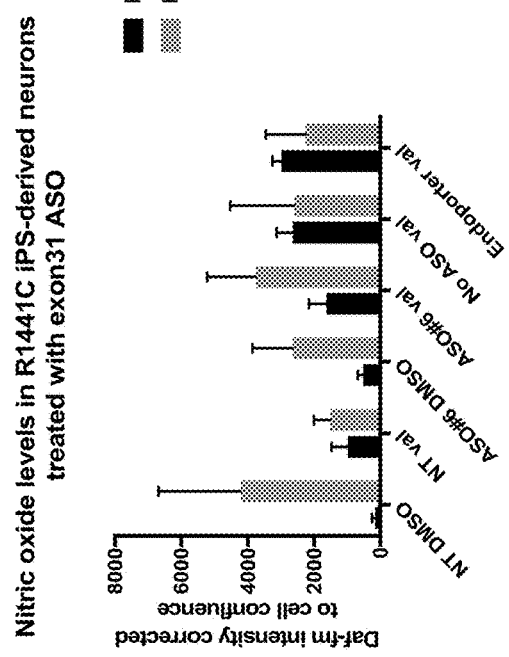
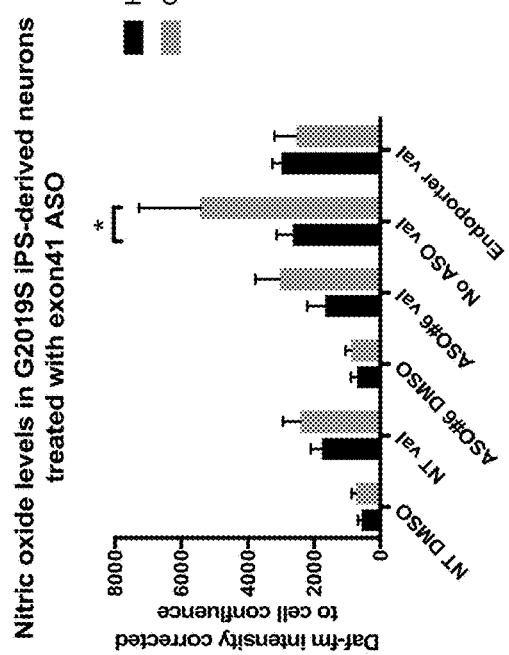

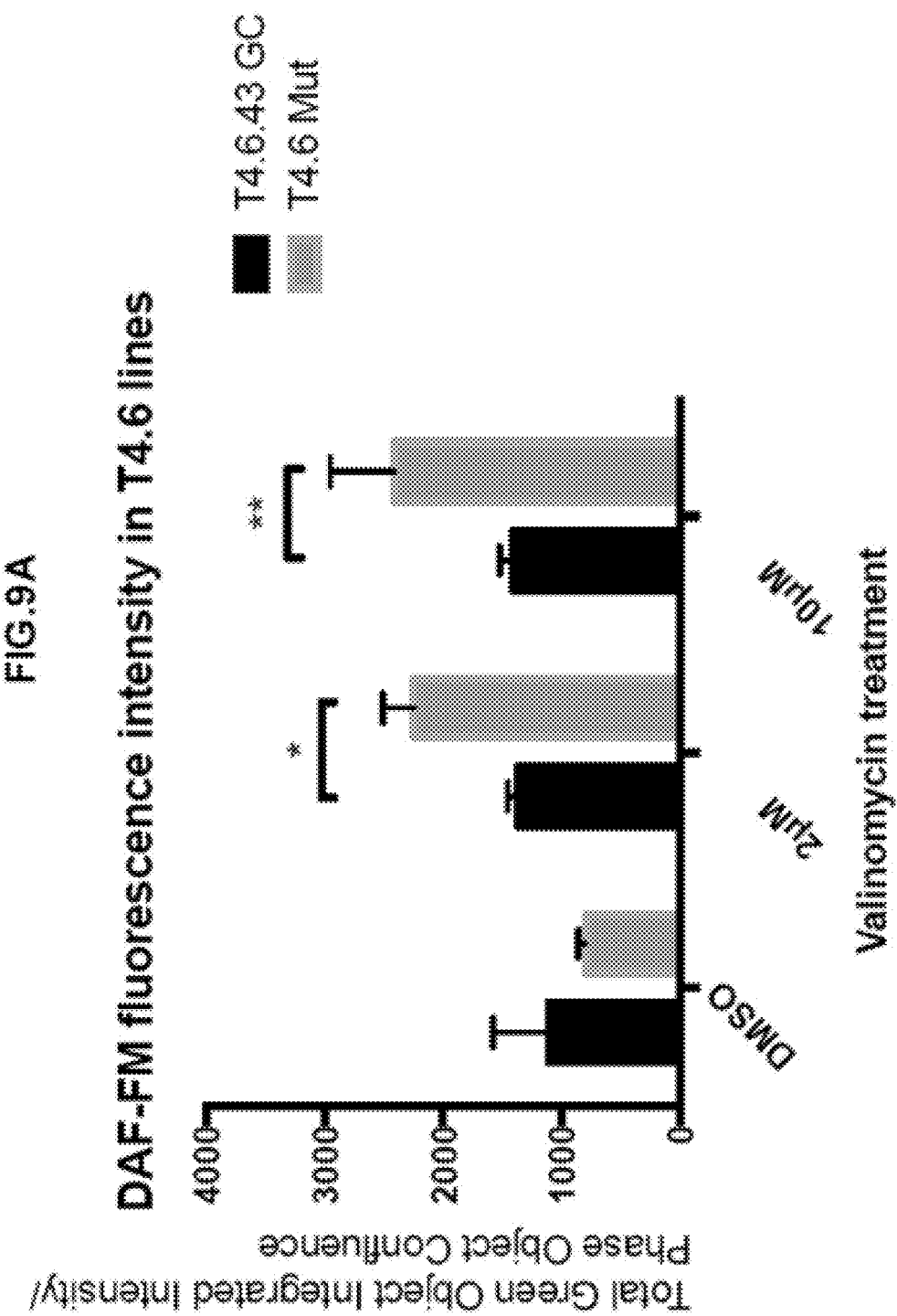

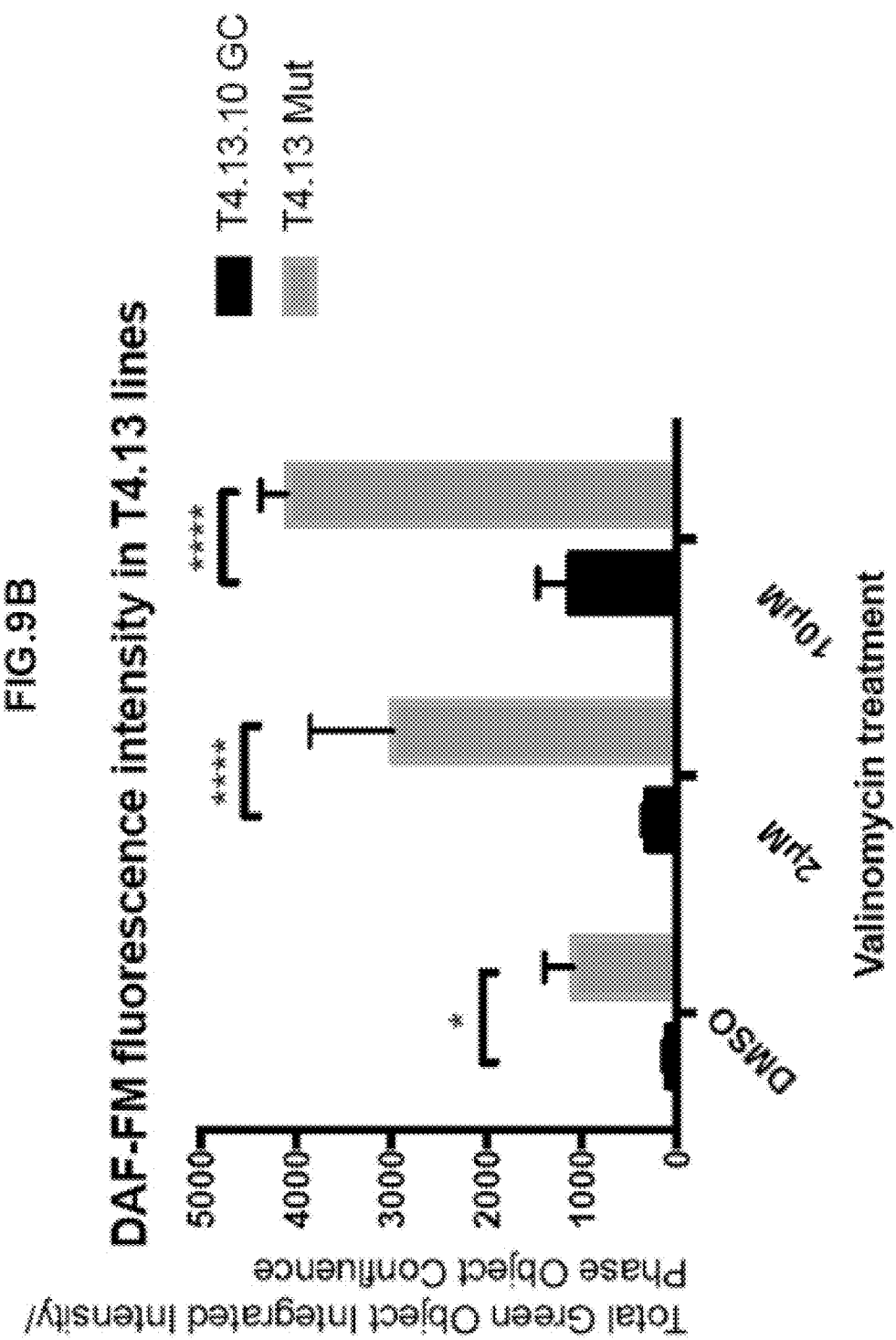

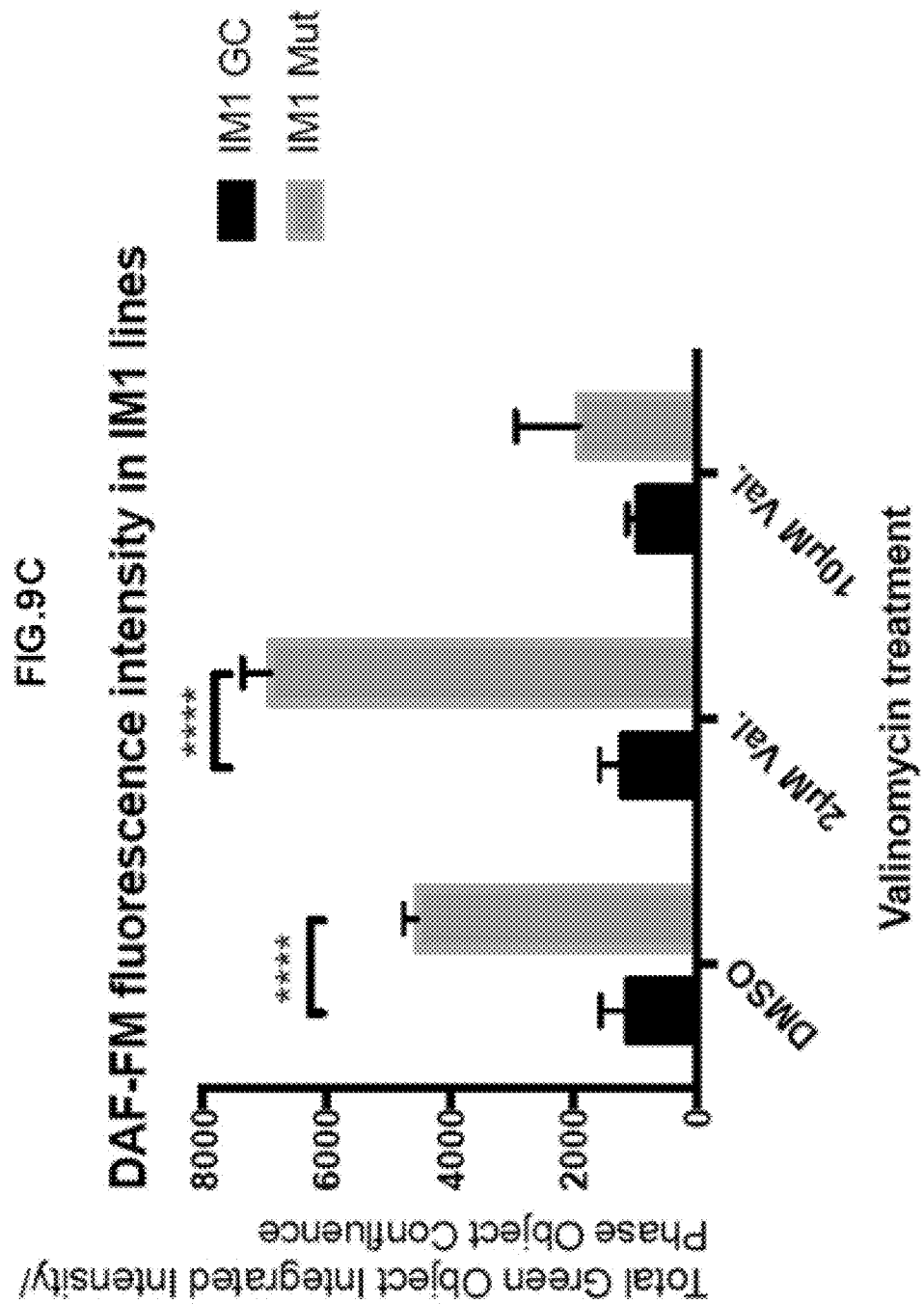

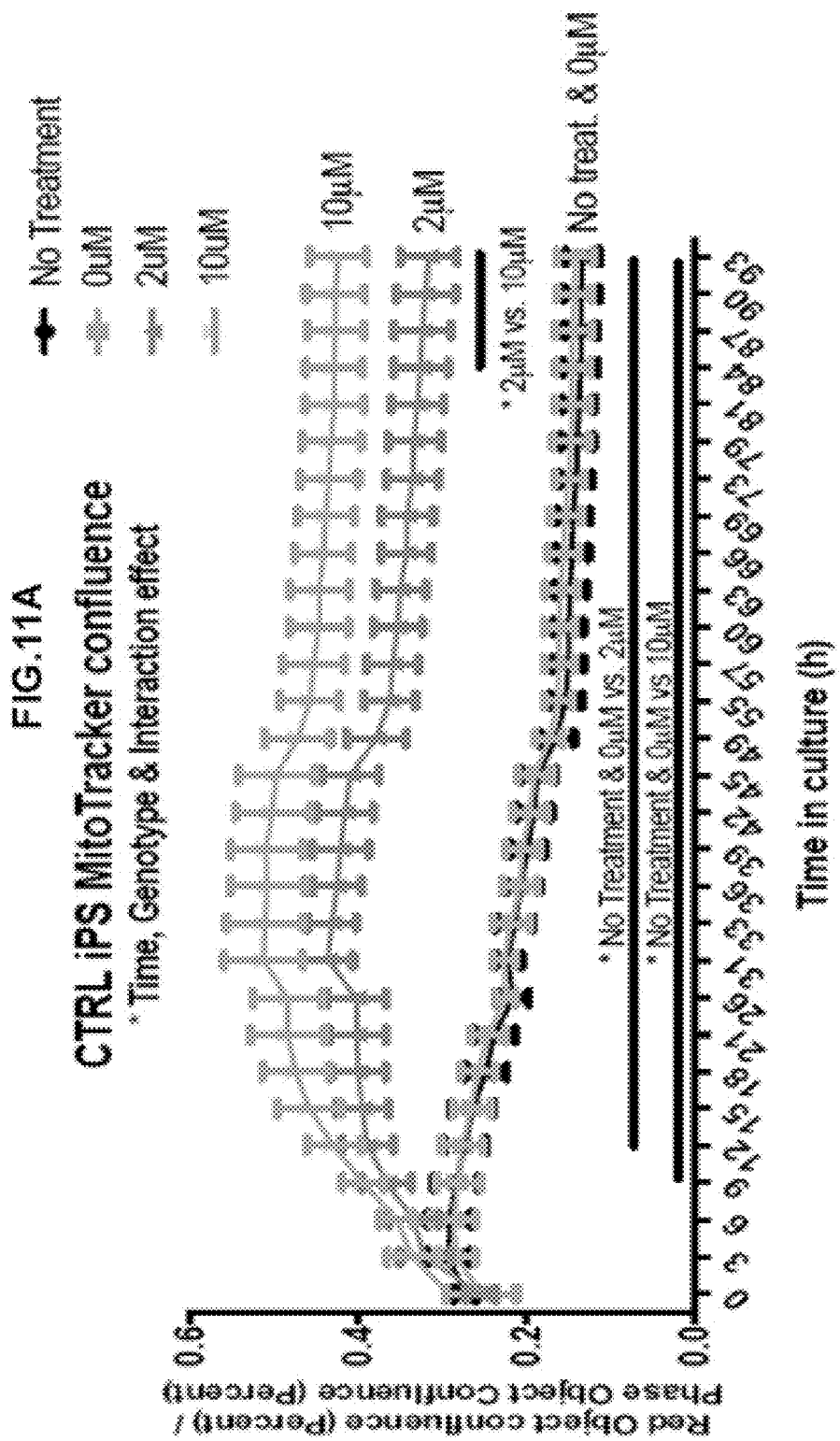

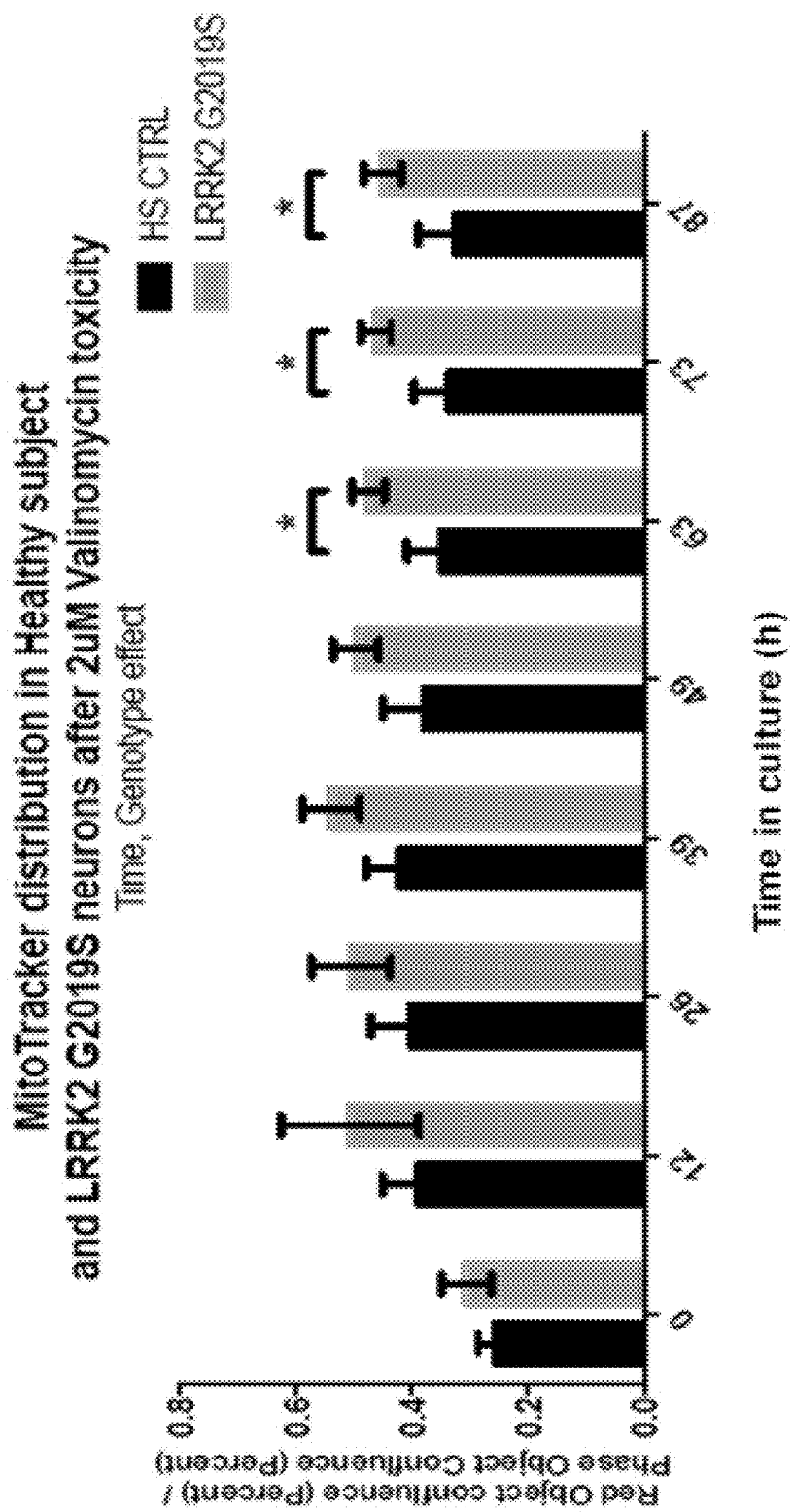

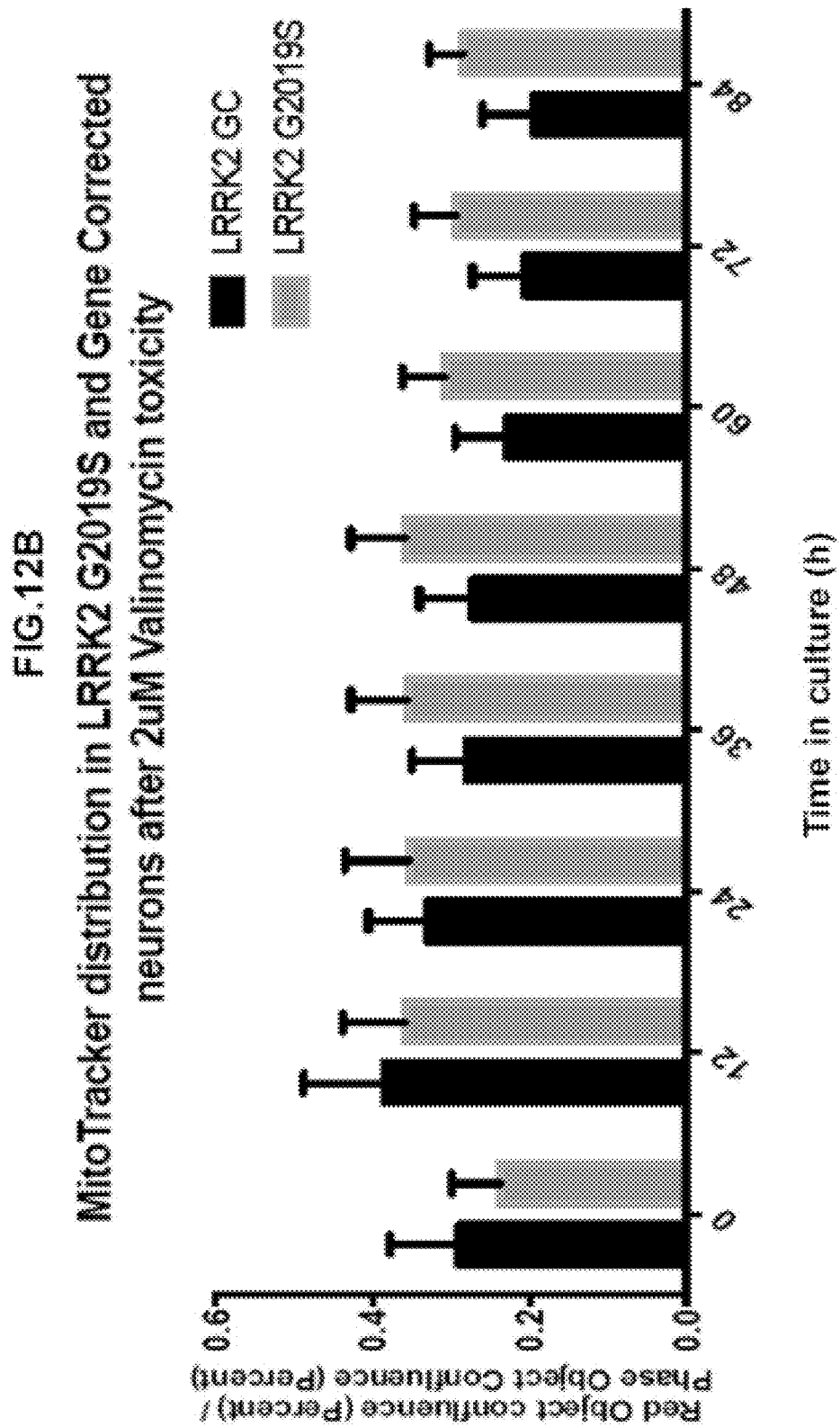

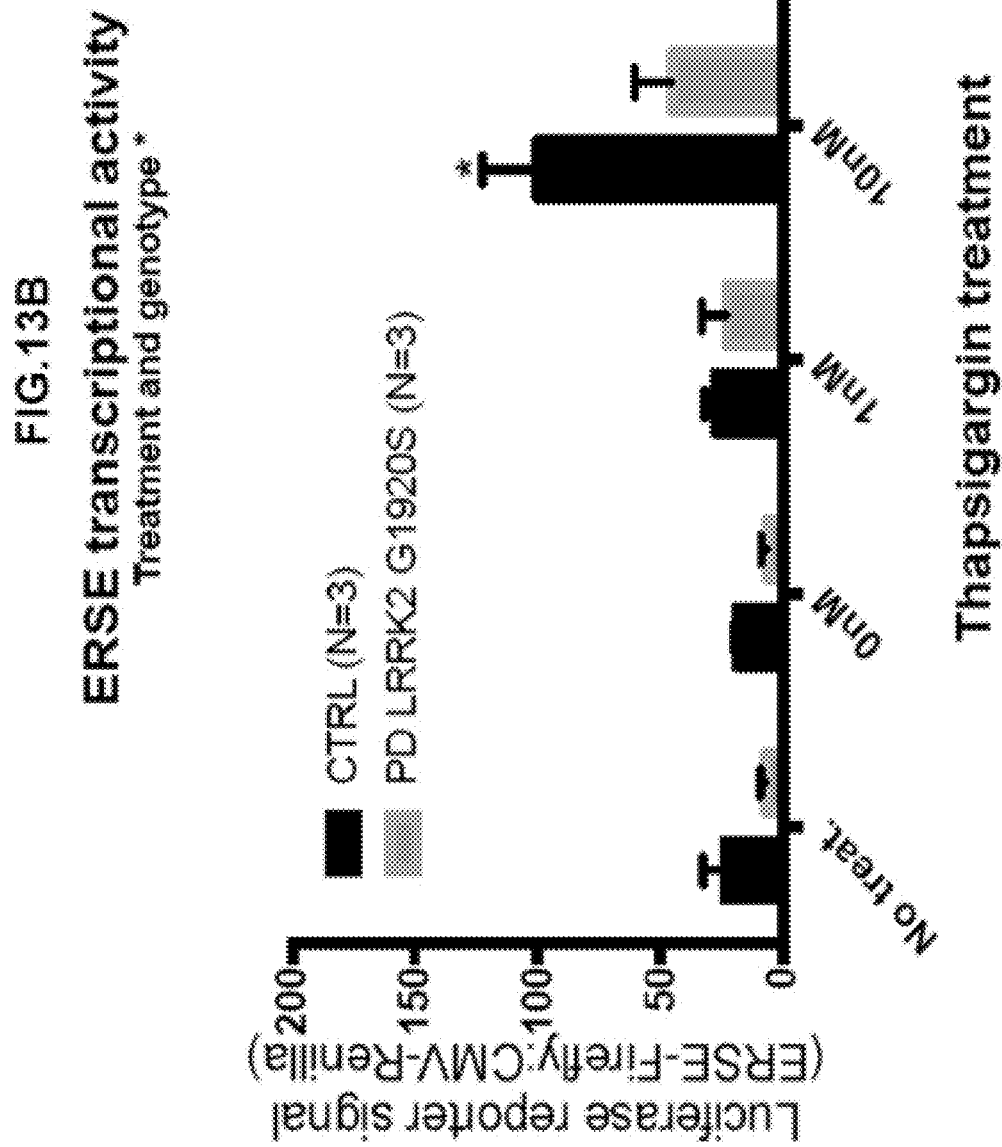

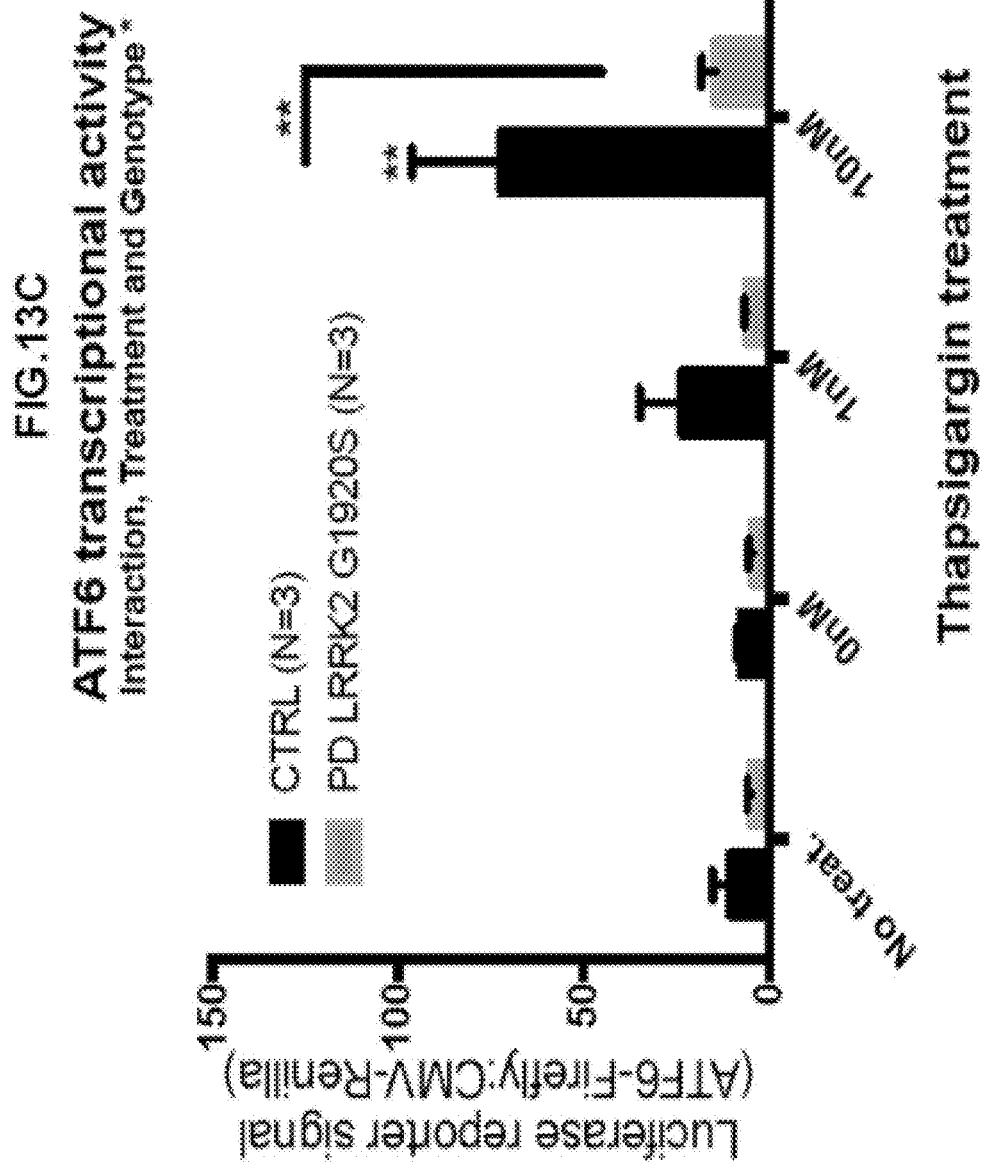

Rosella (Red and Green), Tom20 and Hoechst ICC

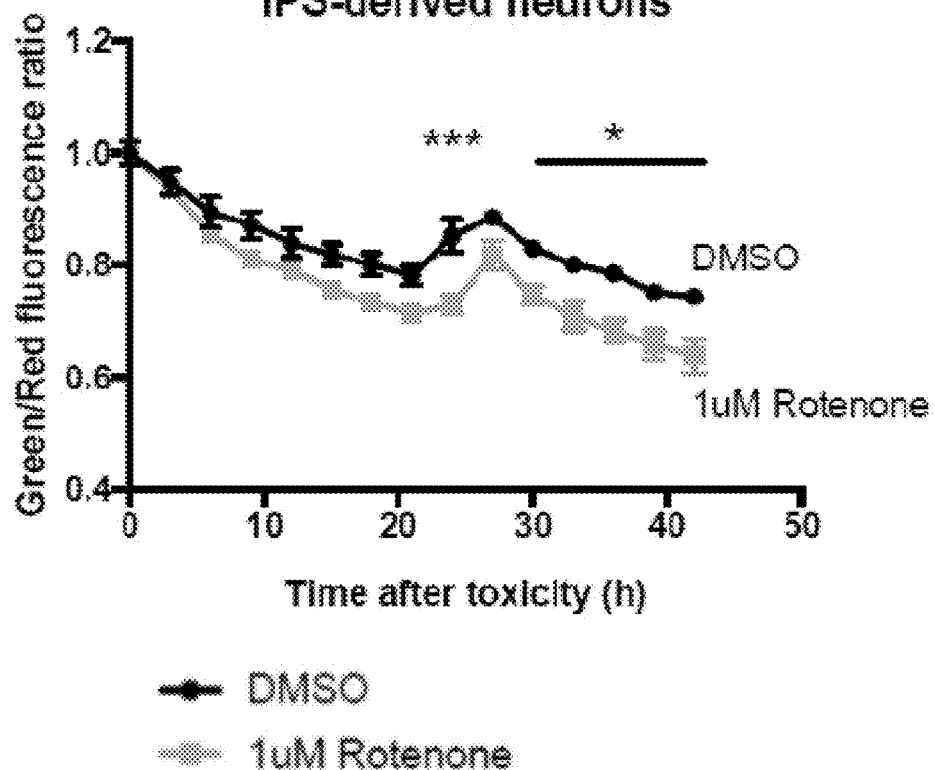

FIG. 15
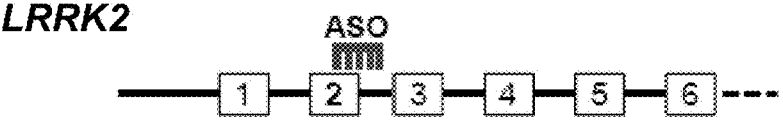
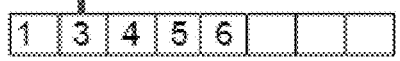
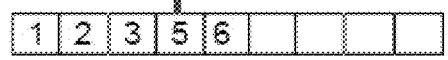

FIG.18
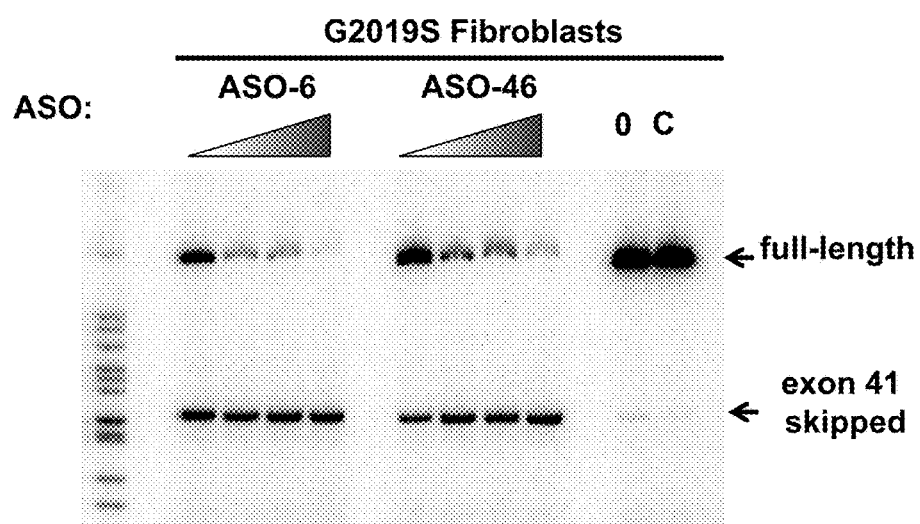
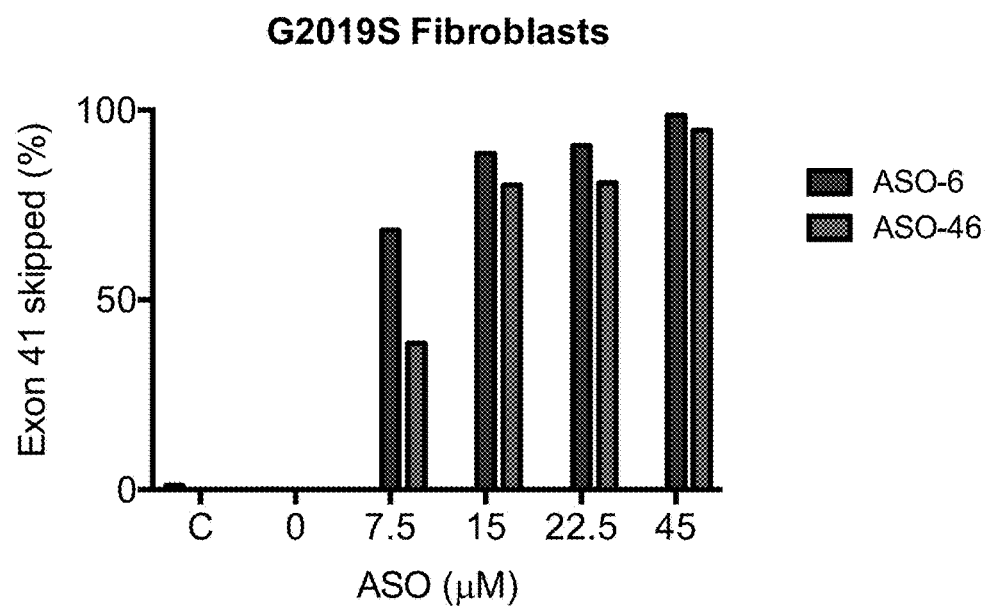

FIG. 21
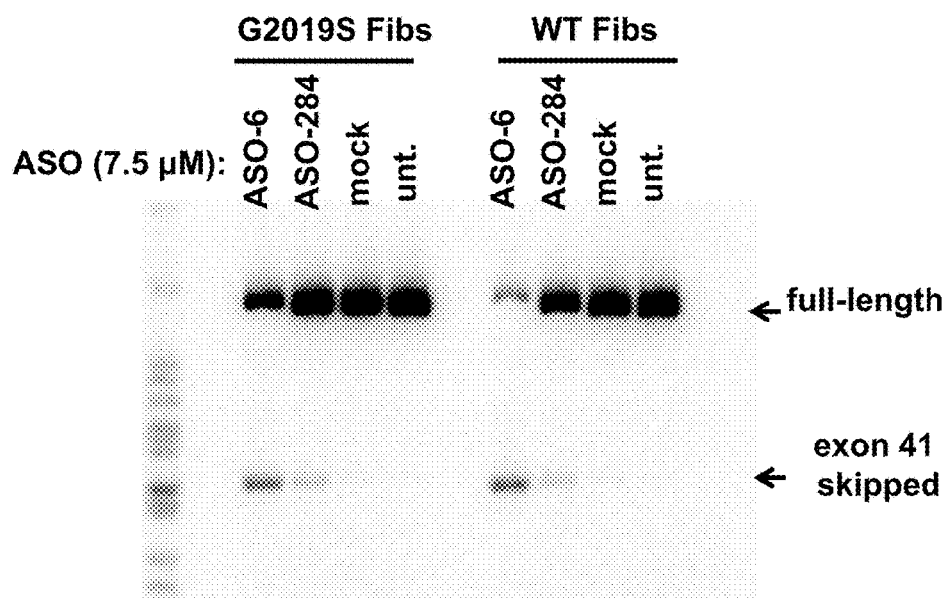
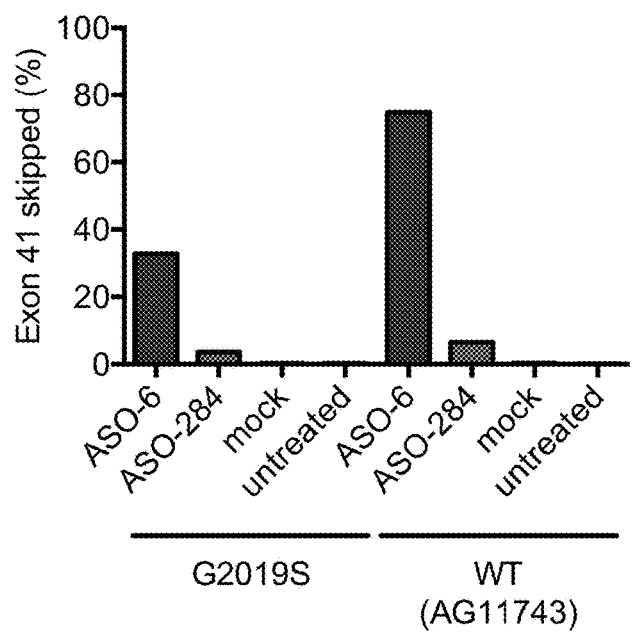

Cellular toxicity in LRRK2 G2019S fibroblasts
after 40uM Valinomycin and exon 41 ASO treatment Mitochondrial acidification in HS and LRRK2 R1441C fibroblasts upon exon 2 skipping

FIG.32A
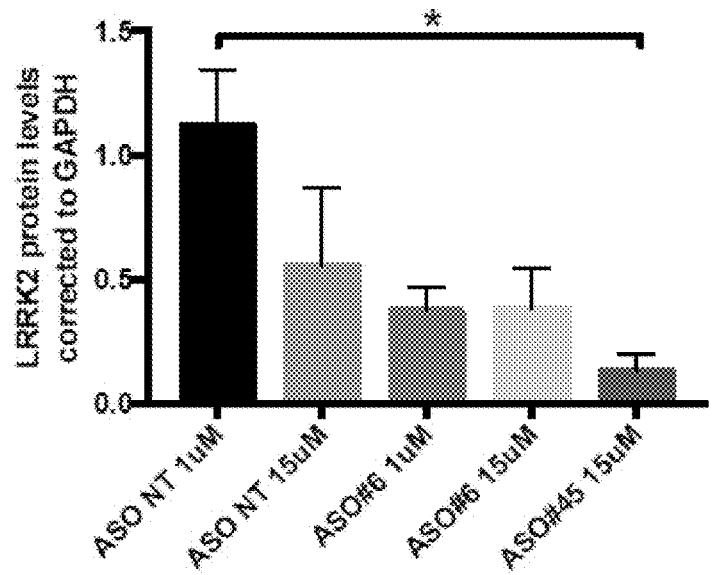
LRRK2 protein levels in human HS fibroblasts after ASO-induced exon41 and exon2 skipping
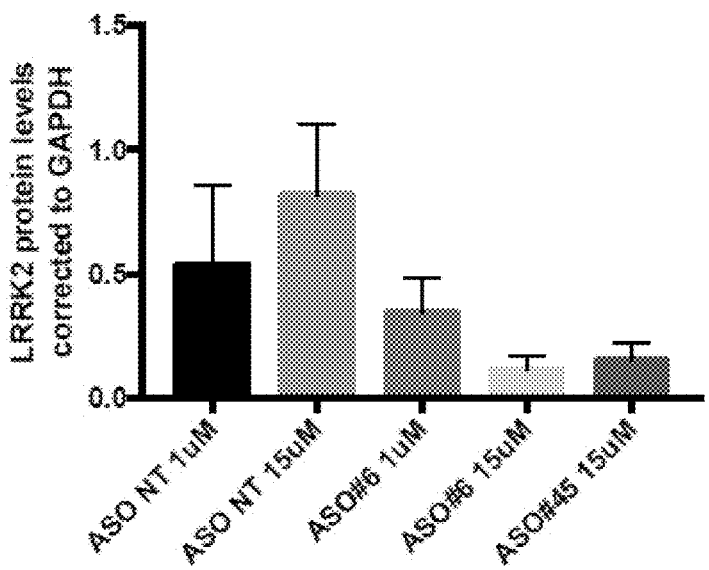
LRRK2 protein levels in human LRRK2 G2019S fibroblasts after ASO-induced exon41 and exon2 skipping LRRK2 protein levels in human HS and LRRK2 G2019SS fibroblasts after ASO-induced exon41 and exon2 skipping FIG.33
Ser935 LRRK2 protein levels in human LRRK2 G2019S fibroblasts after ASO-induced exon41 and exon2 skipping
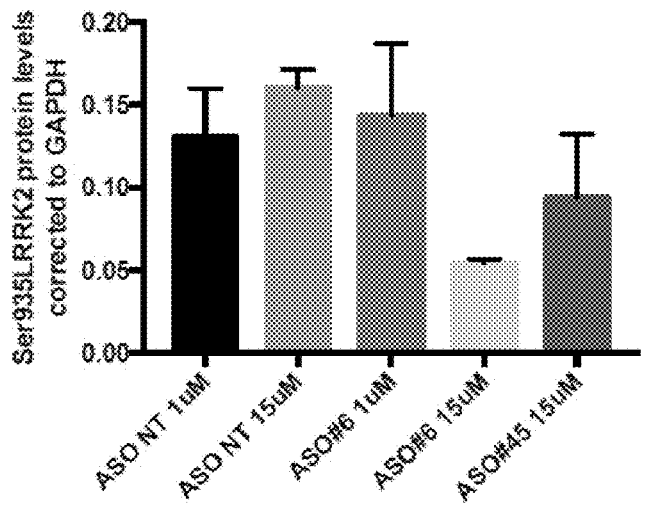
Ser935 LRRK2 protein levels in human LRRK2 G2019S fibroblasts after ASO-induced exon41 and exon2 skipping
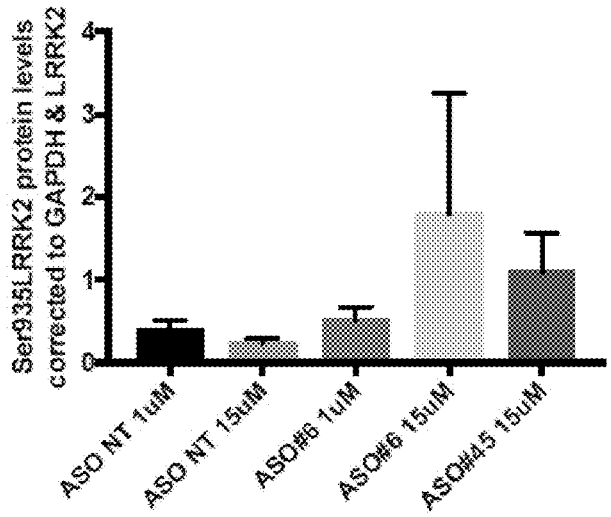

LRRK2 kinase activity measured by LRRK2 Ser935 levels in human fibroblasts after exon31 skipping (ASO#5 15uM)

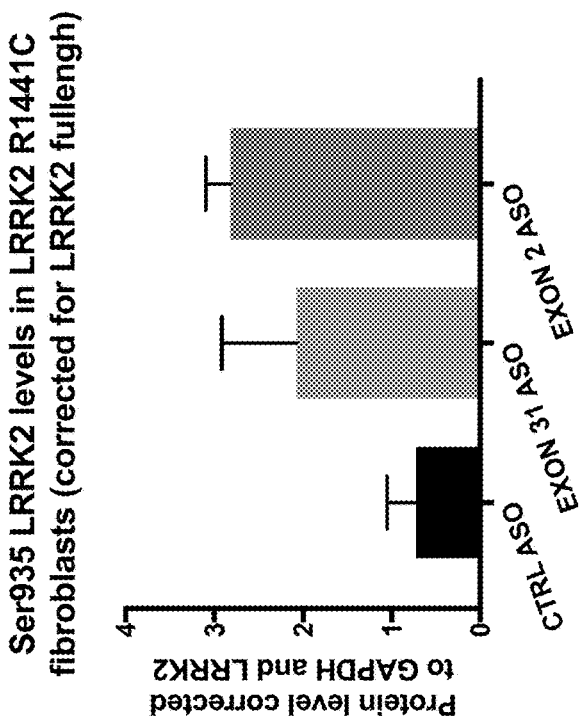
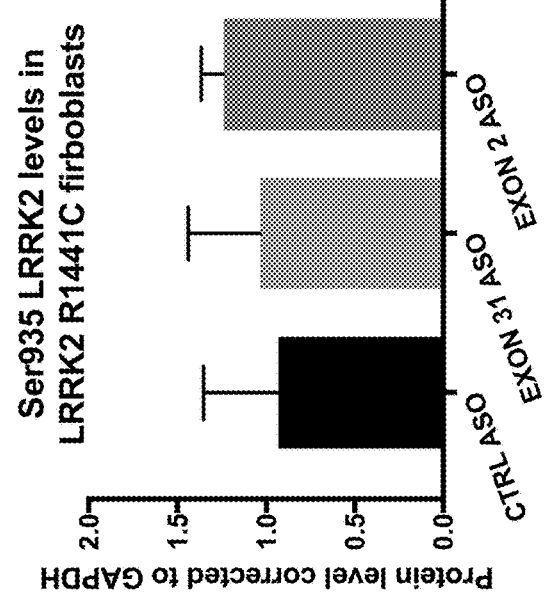
FIG.36

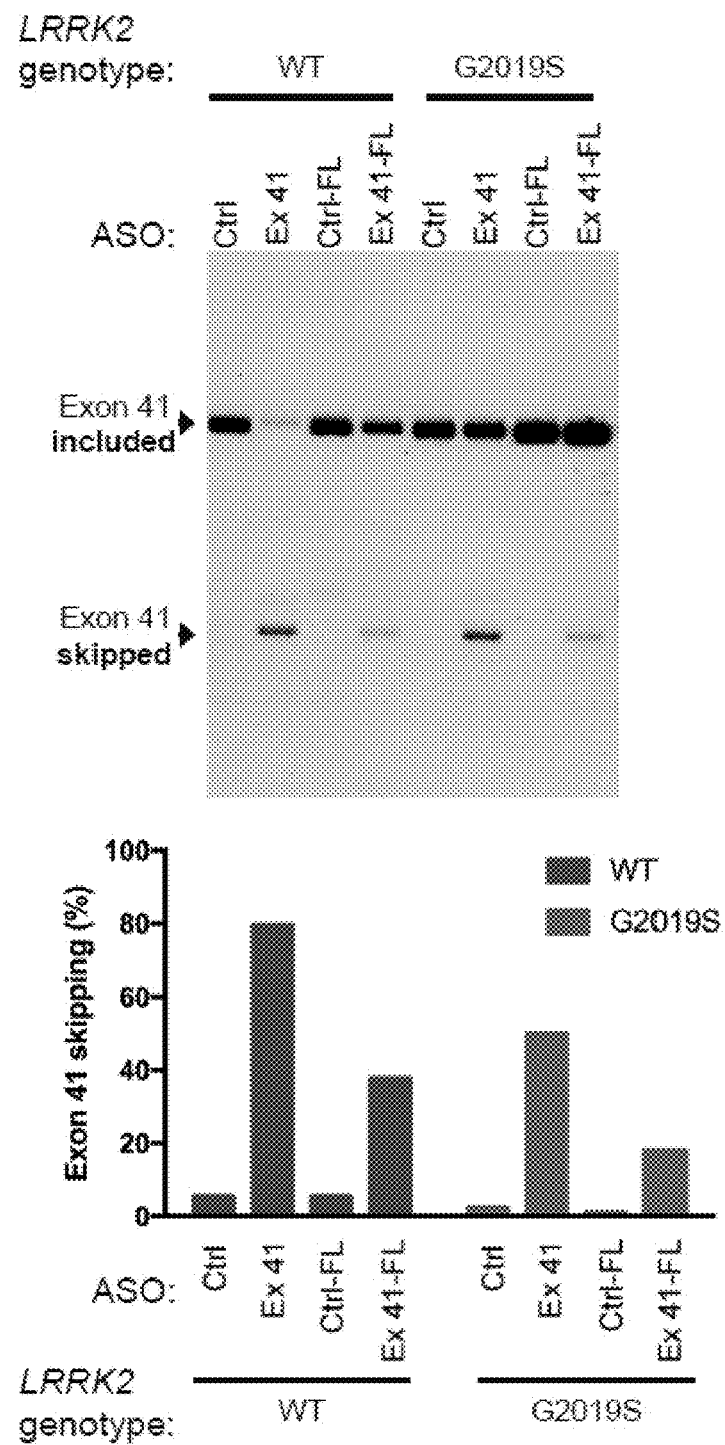

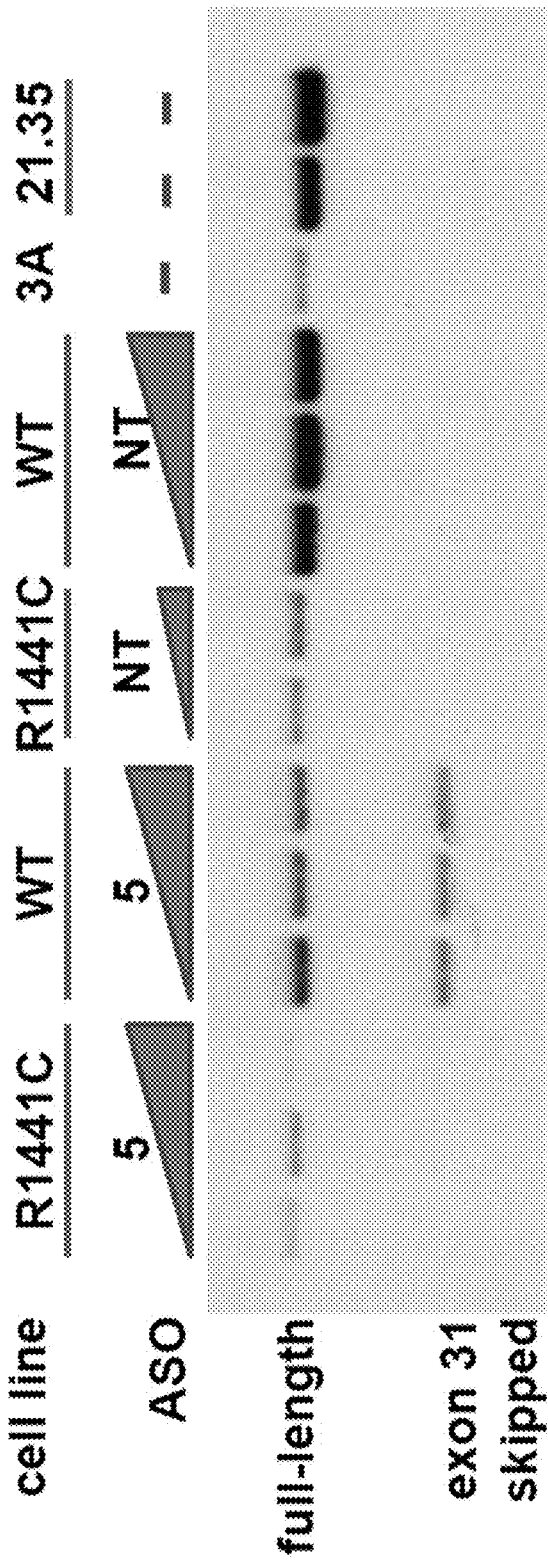

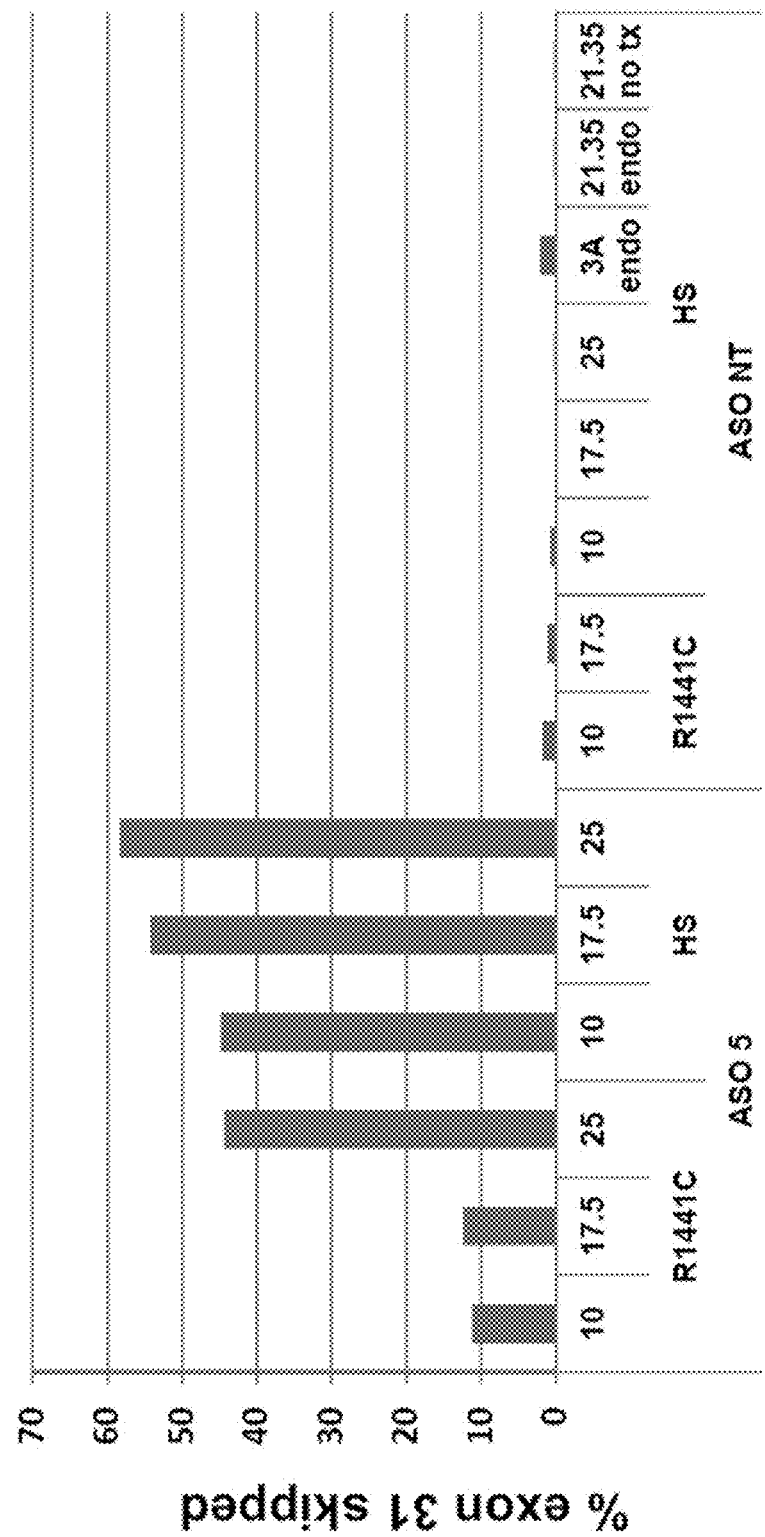

ANTISENSE COMPOUNDS TARGETING LEUCINE-RICH REPEAT KINASE 2 (LRRK2) FOR THE TREATMENT OF PARKINSONS DISEASE

CROSS REFERENCE TO RELATED APPLICATIONS

This application is a continuation-in-part of U.S. application Ser. No. 15/349,840, filed Nov. 11, 2016, now U.S. Pat. No. 9,840,710, issued Dec. 12, 2017, which is a non-provisional application of U.S. Provisional Application 62/257,109, filed Nov. 18, 2015, the disclosures of each of which are incorporated by reference in their entirety.

SEQUENCE LISTING

The sequence listing submitted herewith is incorporated by reference in its entirety.

FIELD OF THE DISCLOSURE

The present disclosure relates generally to compounds comprising oligonucleotides complementary to a Leucine-Rich-Repeat-Kinase (LRRK2) RNA transcript. Certain such compounds are useful for hybridizing to a LRRK2 transcript, including but not limited to a LRRK2 RNA transcript in a cell. In certain embodiments, such hybridization results in modulation of splicing of the LRRK2 transcript. In certain embodiments, such compounds are used to treat one or more symptoms associated with Parkinson's Disease (PD).

BACKGROUND OF THE DISCLOSURE

Parkinson's disease belongs to a group of conditions called motor system disorders, which are the result of the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. Other symptoms may include depression and other emotional changes; difficulty in swallowing, chewing, and speaking; urinary problems or constipation; skin problems; and sleep disruptions. There are currently no blood or laboratory tests that have been proven to help in diagnosing sporadic PD, and diagnosis is based on medical history and a neurological examination.

Currently, there is no cure for PD, but a variety of medications provide relief from the symptoms. Usually, affected individuals are given levodopa combined with carbidopa, which delays the conversion of levodopa into dopamine until it reaches the brain. Nerve cells can use levodopa to make dopamine and replenish the brain's dwindling supply. Although levodopa helps at least three-quarters of parkinsonian cases, not all symptoms respond equally to the drug. Bradykinesia and rigidity respond best, while tremor may be only marginally reduced. Problems with balance and other symptoms may not be alleviated at all. Anticholinergics may help control tremor and rigidity. Other drugs, such as bromocriptine, pramipexole, and ropinirole, mimic the role of dopamine in the brain, causing the neurons to react as they would to dopamine. An antiviral drug, amantadine, also appears to reduce symptoms.

An estimated 53 million people have PD resulting in about 103,000 deaths globally. Parkinson's disease typically occurs in people over the age of 60, with males being affected more often than females. The average life expectancy following diagnosis is between 7 and 14 years. Parkinson's disease is typically idiopathic (having no specific known cause); however, a proportion of cases can be attributed to known genetic factors. For example, mutations in specific genes have been shown to cause PD (e.g., alpha-synuclein (SNCA), parkin (PRKN), leucine-rich repeat kinase 2. (LRRK2), PTEN-induced putative kinase 1 (PINK1), DJ-1 and ATP13A2). Mutations in LRRK2 are the most common known cause of familial and sporadic PD, accounting for approximately 5% of individuals with a family history of the disease and 3% of sporadic cases. The LRRK2 G2019S gain of function gene mutation is one of the most prevalent mutations contributing to PD pathogenesis. While treatments for PD are available, more effective therapies are needed.

SUMMARY OF THE DISCLOSURE

The present disclosure relates to general compounds and methods to treat Parkinson's disease in subjects using antisense oligonucleotides (ASOs) that block specific pre-mRNA splicing events in LRRK2 gene transcripts resulting in non-sense mRNAs or mRNAs that code for LRRK2 proteins with lower kinase activity.

In one aspect, the disclosure provides a compound comprising a modified oligonucleotide having 8 to 30 linked nucleosides having a nucleobase sequence comprising a complementary region, wherein the complementary region comprises at least 8 contiguous nucleobases complementary to an equal-length portion of a target region of a leucine-rich repeat kinase 2 (LRRK2) transcript. In certain embodiments, the target region of the LRRK2 transcript comprises at least a portion of exon 2, exon 4, exon 31 or exon 41 of the LRRK2 transcript. In an embodiment, the target region can be a splice site in the LRRK2 gene. In other embodiments, the nucleobase sequence of the antisense oligonucleotide comprises SEQ ID NO:01, SEQ ID NO:02, SEQ ID NO:06, SEQ ID NO:07, SEQ ID NO:08, or SEQ ID NO:09.

In another aspect, the disclosure provides a pharmaceutical composition comprising at least one compound as described herein and a pharmaceutically acceptable carrier or diluent.

In yet another aspect, the disclosure provides a method of modulating splicing or expression of a LRRK2 transcript in a cell comprising contacting the cell with at least one compound as described herein.

The yet another aspect, the disclosure provides a method of treating Parkinson's disease, comprising administering at least one compound as described herein to an animal in need thereof.

The present disclosure provides the following non-limiting numbered embodiments:

Embodiment 1

A compound comprising a modified oligonucleotide consisting of 8 to 30 linked nucleosides and having a nucleobase sequence comprising a complementary region, wherein the complementary region comprises at least 8 contiguous nucleobases complementary to an equal-length portion of a target region of a leucine-rich repeat kinase 2 (LRRK2) transcript.

Embodiment 2

The compound of embodiment 1, wherein the target region of the LRRK2 transcript comprises at least a portion of exon 2, exon 4, exon 31 or exon 41 of the LRRK2 transcript.

Embodiment 3a

The compound of embodiment 1, wherein the target region of the LRRK2 transcript comprises at least a portion of exon 2 of the LRRK2 transcript.

Embodiment 3b

The compound of embodiment 1, wherein the target region of the LRRK2 transcript comprises at least a portion of exon 4 of the LRRK2 transcript.

Embodiment 4

The compound of embodiment 1, wherein the target region of the LRRK2 transcript comprises at least a portion of exon 31 of the LRRK2 transcript.

Embodiment 5

The compound of embodiment 1, wherein the target region of the LRRK2 transcript comprises at least a portion of exon 41 of the LRRK2 transcript.

Embodiment 6

The compound of embodiment 1, wherein the target region of the LRRK2 transcript comprises a splice site.

Embodiment 7

The compound of embodiment 1, wherein the LRRK2 transcript encodes a protein that has a G2019S mutation or a R1441C mutation.

Embodiment 8

The compound of any of embodiments 1 to 7, wherein the complementary region of the modified oligonucleotide is at least 80%, at least 85%, at least 90%, at least 95% or at least 100% complementary to the target region.

Embodiment 9

The compound of any of embodiments 1 to 8, wherein the complementary region of the modified oligonucleotide comprises at least 10 contiguous nucleobases.

Embodiment 10

The compound of any of embodiments 1 to 8, wherein the complementary region of the modified oligonucleotide comprises at least 12 contiguous nucleobases.

Embodiment 11

The compound of any of embodiments 1 to 8, wherein the complementary region of the modified oligonucleotide comprises at least 14 contiguous nucleobases.

Embodiment 12

The compound of any of embodiments 1 to 8, wherein the complementary region of the modified oligonucleotide comprises at least 15 contiguous nucleobases.

Embodiment 13

The compound of any of embodiments 1 to 8, wherein the complementary region of the modified oligonucleotide comprises at least 16 contiguous nucleobases.

Embodiment 14

The compound of any of embodiments 1 to 8, wherein the complementary region of the modified oligonucleotide comprises at least 17 contiguous nucleobases.

Embodiment 15

The compound of any of embodiments 1 to 8, wherein the complementary region of the modified oligonucleotide comprises at least 18 contiguous nucleobases.

Embodiment 16

The compound of any of embodiments 1 to 8, wherein the complementary region of the modified oligonucleotide comprises at least 19 contiguous nucleobases.

Embodiment 17

The compound of any of embodiments 1 to 8, wherein the complementary region of the modified oligonucleotide comprises at least 20 contiguous nucleobases.

Embodiment 18

The compound of any of embodiments 1 to 17, wherein the nucleobase sequence of the oligonucleotide is at least 80% complementary to an equal-length region of the LRRK2 transcript, as measured over the entire length of the oligonucleotide.

Embodiment 19

The compound of any of embodiments 1 to 17, wherein the nucleobase sequence of the oligonucleotide is at least 90% complementary to an equal-length region of the LRRK2 transcript, as measured over the entire length of the oligonucleotide.

Embodiment 20

The compound of any of embodiments 1 to 17, wherein the nucleobase sequence of the oligonucleotide is 100% complementary to an equal-length region of the LRRK2 transcript, as measured over the entire length of the oligonucleotide.

Embodiment 21

The compound of any of embodiments 1 to 20, wherein the nucleobase sequence of the antisense oligonucleotide comprises any one of SEQ ID NO:01, SEQ ID NO:02, SEQ ID NO:06, SEQ ID NO:07, SEQ ID NO:08, or SEQ ID NO:09.

Embodiment 22

The compound of any of embodiments 1 to 21, wherein the modified oligonucleotide comprises at least one modified nucleoside.

Embodiment 23

The compound of embodiment 22, wherein at least one modified nucleoside comprises a modified sugar moiety.

Embodiment 24

The compound of embodiment 23, wherein at least one modified sugar moiety is a 2'-substituted sugar moiety.

Embodiment 25

The compound of embodiment 24, wherein the 2'-substitutent of at least one 2'-substituted sugar moiety is selected from among: 2'-OMe, 2'-F, and 2'-MOE.

Embodiment 26

The compound of any of embodiments 22 to 25, wherein the 2'-substituent of at least one 2'-substituted sugar moiety is a 2'-MOE.

Embodiment 27

The compound of any of embodiments 1 to 26, wherein at least one modified sugar moiety is a bicyclic sugar moiety.

Embodiment 28

The compound of embodiment 27, wherein at least one bicyclic sugar moiety is LNA or cEt.

Embodiment 29

The compound of any of embodiments 1 to 28, wherein at least one sugar moiety is a sugar surrogate.

Embodiment 30

The compound of embodiment 29, wherein at least one sugar surrogate is a morpholino.

Embodiment 31

The compound of embodiment 29, wherein at least one sugar surrogate is a modified morpholino.

Embodiment 32

The compound of any of embodiments 1 to 31, wherein the modified oligonucleotide comprises at least 5 modified nucleosides, each independently comprising a modified sugar moiety.

Embodiment 33

The compound of embodiment 32, wherein the modified oligonucleotide comprises at least 10 modified nucleosides, each independently comprising a modified sugar moiety.

Embodiment 34

The compound of embodiment 32, wherein the modified oligonucleotide comprises at least 15 modified nucleosides, each independently comprising a modified sugar moiety.

Embodiment 35

The compound of embodiment 32, wherein each nucleoside of the modified oligonucleotide is a modified nucleoside, each independently comprising a modified sugar moiety

Embodiment 36

The compound of any of embodiments 1 to 35, wherein the modified oligonucleotide comprises at least two modified nucleosides comprising modified sugar moieties that are the same as one another.

Embodiment 37

The compound of any of embodiments 1 to 35, wherein the modified oligonucleotide comprises at least two modified nucleosides comprising modified sugar moieties that are different from one another.

Embodiment 38

The compound of any of embodiments 1 to 37, wherein the modified oligonucleotide comprises a modified region of at least 5 contiguous modified nucleosides.

Embodiment 39

The compound of any of embodiments 1 to 38, wherein the modified oligonucleotide comprises a modified region of at least 10 contiguous modified nucleosides.

Embodiment 40

The compound of any of embodiments 1 to 39, wherein the modified oligonucleotide comprises a modified region of at least 15 contiguous modified nucleosides.

Embodiment 41

The compound of any of embodiments 1 to 39, wherein the modified oligonucleotide comprises a modified region of at least 20 contiguous modified nucleosides.

Embodiment 42

The compound of any of embodiments 36 to 41, wherein each modified nucleoside of the modified region has a modified sugar moiety independently selected from among: 2'-F, 2'-OMe, 2'-MOE, cEt, LNA, morpholino, and modified morpholino.

Embodiment 43

The compound of any of embodiments 36 to 42 wherein the modified nucleosides of the modified region each comprise the same modification as one another.

Embodiment 44

The compound of embodiment 43, wherein the modified nucleosides of the modified region each comprise the same 2'-substituted sugar moiety.

Embodiment 45

The compound of embodiment 43, wherein the 2'-substituted sugar moiety of the modified nucleosides of the region of modified nucleosides is selected from 2'-F, 2'-OMe, and 2'-MOE.

Embodiment 46

The compound of embodiment 45, wherein the 2'-substituted sugar moiety of the modified nucleosides of the region of modified nucleosides is 2'-MOE.

Embodiment 47

The compound of embodiment 43, wherein the modified nucleosides of the region of modified nucleosides each comprise the same bicyclic sugar moiety.

Embodiment 48

The compound of embodiment 47, wherein the bicyclic sugar moiety of the modified nucleosides of the region of modified nucleosides is selected from LNA and cEt.

Embodiment 49

The compound of embodiment 41, wherein the modified nucleosides of the region of modified nucleosides each comprises a sugar surrogate.

Embodiment 50

The compound of embodiment 49, wherein the sugar surrogate of the modified nucleosides of the region of modified nucleosides is a morpholino.

Embodiment 51

The compound of embodiment 50, wherein the sugar surrogate of the modified nucleosides of the region of modified nucleosides is a modified morpholino.

Embodiment 52

The compound of any of embodiments 1 to 51, wherein the modified nucleotide comprises no more than 4 contiguous naturally occurring nucleosides.

Embodiment 53

The compound of any of embodiments 1 to 52, wherein each nucleoside of the modified oligonucleotide is a modified nucleoside.

Embodiment 54

The compound of embodiment 53, wherein each modified nucleoside comprises a modified sugar moiety.

Embodiment 55

The compound of embodiment 54, wherein the modified nucleosides of the modified oligonucleotide comprise the same modification as one another.

Embodiment 56

The compound of embodiment 55, wherein the modified nucleosides of the modified oligonucleotide each comprise the same 2'-substituted sugar moiety.

Embodiment 57

The compound of embodiment 56, wherein the 2'-substituted sugar moiety of the modified oligonucleotide is selected from 2'-F, 2'-OMe, and 2'-MOE.

Embodiment 58

The compound of embodiment 56, wherein the 2'-substituted sugar moiety of the modified oligonucleotide is 2'-MOE.

Embodiment 59

The compound of embodiment 55, wherein the modified nucleosides of the modified oligonucleotide each comprise the same bicyclic sugar moiety.

Embodiment 60

The compound of embodiment 59, wherein the bicyclic sugar moiety of the modified oligonucleotide is selected from LNA and cEt.

Embodiment 61

The compound of embodiment 55, wherein the modified nucleosides of the modified oligonucleotide each comprises a sugar surrogate.

Embodiment 62

The compound of embodiment 61, wherein the sugar surrogate of the modified oligonucleotide is a morpholino.

Embodiment 63

The compound of embodiment 61, wherein the sugar surrogate of the modified oligonucleotide is a modified morpholino.

Embodiment 64

The compound of any of embodiments 1 to 63, wherein the modified oligonucleotide comprises at least one modified internucleoside linkage.

Embodiment 65

The compound of embodiment 64, wherein each internucleoside linkage is a modified internucleoside linkage.

Embodiment 66

The compound of embodiment 64 or 65, comprising at least one phosphorothioate internucleoside linkage.

Embodiment 67

The compound of embodiment 64, wherein each internucleoside linkage is a modified internucleoside linkage and wherein each internucleoside linkage comprises the same modification.

Embodiment 68

The compound of embodiment 67, wherein each internucleoside linkage is a phosphorothioate internucleoside linkage.

Embodiment 69

The compound of any of embodiments 1 to 68, comprising at least one conjugate.

Embodiment 70

The compound of any of embodiments 1 to 69, consisting of the modified oligonucleotide.

Embodiment 71

The compound of any of embodiments 1 to 70, wherein the compound modulates splicing of the LRRK2 transcript.

Embodiment 72

The compound of any of embodiments 1 to 71, having a nucleobase sequence comprising any of the sequences as set forth in SEQ ID NO:02, SEQ ID NO:08, or SEQ ID NO:09.

Embodiment 73

The compound of any of embodiments 1 to 72, having a nucleobase sequence comprising any of the sequences as set forth in SEQ ID NO:01.

Embodiment 74

The compound of any of embodiments 1 to 72, having a nucleobase sequence comprising any of the sequences as set forth in SEQ ID NO:06.

Embodiment 73

The compound of any of embodiment 73, having a nucleobase sequence comprising SEQ ID NO:07.

Embodiment 74

A pharmaceutical composition comprising a compound according to any of embodiments 1 to 73 and a pharmaceutically acceptable carrier or diluent.

Embodiment 75

The pharmaceutical composition of embodiment 74, wherein the pharmaceutically acceptable carrier or diluent is sterile saline.

Embodiment 76

A method of modulating splicing of a LRRK2 transcript in a cell comprising contacting the cell with a compound according to any of embodiments 1 to 75.

Embodiment 77

The method of embodiment 76, wherein the cell is in vitro.

Embodiment 78

The method of embodiment 76, wherein the cell is in an animal.

Embodiment 79a

The method of any of embodiments 76 to 78, wherein the amount of LRRK2 mRNA without exon 2 is increased.

Embodiment 79b

The method of any of embodiments 76 to 78, wherein the amount of LRRK2 mRNA without exon 4 is increased.

Embodiment 80

The method of any of embodiments 76 to 78, wherein the amount of LRRK2 mRNA without exon 31 is increased.

Embodiment 81

The method of any of embodiments 76 to 78, wherein the amount of LRRK2 mRNA without exon 41 is increased.

Embodiment 82

The method of any of embodiments 76 to 81, wherein the LRRK2 transcript is transcribed from a LRRK2 gene.

Embodiment 83

A method of modulating the expression of LRRK2 in a cell, comprising contacting the cell with a compound according to any of embodiments 1 to 75.

Embodiment 84

The method of embodiment 83, wherein the cell is in vitro.

Embodiment 85

The method of embodiment 83, wherein the cell is in an animal.

Embodiment 86

A method comprising administering the compound according to any of embodiments 1 to 73 or the pharmaceutical composition of embodiments 74 or 75 to an animal.

Embodiment 87

The method of embodiment 86, wherein the administering step comprises delivering to the animal by intracerebroventricular injection, inhalation, parenteral injection or infusion, oral, subcutaneous or intramuscular injection, buccal, transdermal, transmucosal and topical.

Embodiment 88

The method of embodiment 87, wherein the administration is by intracerebroventricular injection.

Embodiment 89

The method of any of embodiments 86 to 88, wherein the animal has one or more symptoms associated with Parkinson's disease.

Embodiment 90

The method of any of embodiments 86 to 88, wherein the administration results in amelioration of at least one symptom of Parkinson's disease.

Embodiment 91

The method of any of embodiments 86 to 90, wherein the animal is a human.

Embodiment 92

A method of treating Parkinson's disease, comprising administering the compound according to any of embodiments 1 to 73 or the pharmaceutical composition of embodiments 74 or 75 to an animal in need thereof.

Embodiment 93

Use of the compound according to any of embodiments 1 to 73 or the pharmaceutical composition of embodiments 74 or 75 for the preparation of a medicament for use in the treatment of Parkinson's disease.

Embodiment 94

Use of the compound according to any of embodiments 1 to 73 or the pharmaceutical composition of embodiments 74 or 75 for the preparation of a medicament for use in the amelioration of one or more symptoms associated with Parkinson's disease.

Embodiment 95

A compound comprising a modified oligonucleotide consisting of 8 to 30 linked nucleosides and having a nucleobase sequence comprising a complementary region, wherein the complementary region comprises at least 8 contiguous nucleobases complementary to an equal-length portion of a target region of a LRRK2 transcript.

Embodiment 96

The compound of embodiment 95, wherein the LRRK2 transcript comprises the nucleobase sequence of SEQ ID NO:03.

Embodiment 97

The compound of embodiment 95 or 96, wherein the complementary region of the modified oligonucleotide is 100% complementary to the target region.

Embodiment 98

The compound of any of embodiments 95 to 97, wherein the complementary region of the modified oligonucleotide comprises at least 10 contiguous nucleobases.

Embodiment 99

The compound of any of embodiments 95 to 97, wherein the complementary region of the modified oligonucleotide comprises at least 12 contiguous nucleobases.

Embodiment 100

The compound of any of embodiments 95 to 97, wherein the complementary region of the modified oligonucleotide comprises at least 14 contiguous nucleobases.

Embodiment 101

The compound of any of embodiments 95 to 97, wherein the complementary region of the modified oligonucleotide comprises at least 15 contiguous nucleobases.

Embodiment 102

The compound of any of embodiments 95 to 97, wherein the complementary region of the modified oligonucleotide comprises at least 16 contiguous nucleobases.

Embodiment 103

The compound of any of embodiments 95 to 97, wherein the complementary region of the modified oligonucleotide comprises at least 17 contiguous nucleobases.

Embodiment 104

The compound of any of embodiments 95 to 97, wherein the complementary region of the modified oligonucleotide comprises at least 18 contiguous nucleobases.

Embodiment 105

The compound of any of embodiments 95 to 104, wherein the nucleobase sequence of the modified oligonucleotide is at least 80% complementary to an equal-length region of the LRRK2 transcript, as measured over the entire length of the oligonucleotide.

Embodiment 106

The compound of any of embodiments 95 to 104, wherein the nucleobase sequence of the modified oligonucleotide is at least 90% complementary to an equal-length region of the LRRK2 transcript, as measured over the entire length of the oligonucleotide.

Embodiment 107

The compound of any of embodiments 95 to 104, wherein the nucleobase sequence of the modified oligonucleotide is

Embodiment 108

The compound of any of embodiments 95 to 107, wherein the target region is within exon 2, exon 4, exon 31 or exon 41 of human LRRK2.

Embodiment 109

The compound of embodiment 108, wherein the target region is within exon 31 of human LRRK2.

Embodiment 110

The compound of embodiment 108, wherein the target region is within exon 41 of human LRRK2.

Embodiment 111

The compound of any of embodiments 95 to 107, wherein the modified oligonucleotide has a nucleobase sequence comprising any of the sequences as set forth in SEQ ID NO:02, SEQ ID NO:08, or SEQ ID NO:09.

Embodiment 112

The compound of any of embodiments 95 to 107, wherein the modified oligonucleotide has a nucleobase sequence consisting of the nucleobase sequence of any one of SEQ ID NO:01.

Embodiment 113

The compound of any of embodiments 95 to 107, wherein the modified oligonucleotide has a nucleobase sequence comprising the nucleobase sequence of SEQ ID NO:06.

Embodiment 114

The compound of any of embodiments 95 to 107, wherein the modified oligonucleotide has a nucleobase sequence consisting of the nucleobase sequence of SEQ ID NO:07.

Embodiment 115

The compound of any of embodiments 95 to 107, wherein the modified oligonucleotide has a nucleobase sequence comprising the nucleobase sequence of SEQ ID NO:01 SEQ ID NO:02, SEQ ID NO:06, SEQ ID NO:07, SEQ ID NO:08, or SEQ ID NO:09.

Embodiment 116

The compound of embodiment 115, wherein the modified oligonucleotide has a nucleobase sequence consisting of the nucleobase sequence of SEQ ID NO:09.

Embodiment 117

The compound of any of embodiments 95 to 116, wherein the modified oligonucleotide comprises at least one modified nucleoside.

Embodiment 118

The compound of any of embodiments 95 to 117, wherein each nucleoside of the modified oligonucleotide is a modified nucleoside selected from among: 2'-OMe, 2'-F, and 2'-MOE or a sugar surrogate.

Embodiment 119

The compound of embodiment 118, wherein the modified nucleoside is 2'-MOE.

Embodiment 120

The compound of embodiment 117, wherein the modified nucleoside is a morpholino.

Embodiment 121

The compound of embodiment 117, wherein at least one modified nucleoside comprises a modified sugar moiety.

Embodiment 122

The compound of embodiment 121, wherein at least one modified sugar moiety is a 2'-substituted sugar moiety.

Embodiment 123

The compound of embodiment 122, wherein the 2'-substitutent of at least one 2'-substituted sugar moiety is selected from among: 2'-OMe, 2'-F, and 2'-MOE.

Embodiment 124

The compound of any of embodiments 122 to 123, wherein the 2'-substituent of at least one 2'-substituted sugar moiety is a 2'-MOE.

Embodiment 125

The compound of any of embodiments 95 to 124, wherein at least one modified sugar moiety is a bicyclic sugar moiety.

Embodiment 126

The compound of embodiment 125, wherein at least one bicyclic sugar moiety is LNA or cEt.

Embodiment 127

The compound of any of embodiments 95 to 126, wherein at least one sugar moiety is a sugar surrogate.

Embodiment 128

The compound of embodiment 127, wherein at least one sugar surrogate is a morpholino.

Embodiment 129

The compound of embodiment 128, wherein at least one sugar surrogate is a modified morpholino.

Embodiment 130

The compound of any of embodiments 95 to 129, wherein the modified oligonucleotide comprises at least 5 modified nucleosides, each independently comprising a modified sugar moiety.

Embodiment 131

The compound of any of embodiments 95 to 130, wherein the modified oligonucleotide comprises at least 10 modified nucleosides, each independently comprising a modified sugar moiety.

Embodiment 132

The compound of any of embodiments 95 to 130, wherein the modified oligonucleotide comprises at least 15 modified nucleosides, each independently comprising a modified sugar moiety.

Embodiment 133

The compound of any of embodiments 95 to 130, wherein each nucleoside of the modified oligonucleotide is a modified nucleoside, each independently comprising a modified sugar moiety.

Embodiment 134

The compound of any of embodiments 95 to 133, wherein the modified oligonucleotide comprises at least two modified nucleosides comprising modified sugar moieties that are the same as one another.

Embodiment 135

The compound of any of embodiments 95 to 133, wherein the modified oligonucleotide comprises at least two modified nucleosides comprising modified sugar moieties that are different from one another.

Embodiment 136

The compound of any of embodiments 95 to 136, wherein the modified oligonucleotide comprises a modified region of at least 5 contiguous modified nucleosides.

Embodiment 137

The compound of any of embodiments 95 to 135, wherein the modified oligonucleotide comprises a modified region of at least 10 contiguous modified nucleosides.

Embodiment 138

The compound of any of embodiments 95 to 135, wherein the modified oligonucleotide comprises a modified region of at least 15 contiguous modified nucleosides.

Embodiment 139

The compound of any of embodiments 95 to 135, wherein the modified oligonucleotide comprises a modified region of at least 16 contiguous modified nucleosides.

Embodiment 140

The compound of any of embodiments 95 to 135, wherein the modified oligonucleotide comprises a modified region of at least 17 contiguous modified nucleosides.

Embodiment 141

The compound of any of embodiments 95 to 135, wherein the modified oligonucleotide comprises a modified region of at least 18 contiguous modified nucleosides.

Embodiment 142

The compound of any of embodiments 95 to 135, wherein the modified oligonucleotide comprises a modified region of at least 20 contiguous modified nucleosides.

Embodiment 143

The compound of any of embodiments 136 to 142, wherein each modified nucleoside of the modified region has a modified sugar moiety independently selected from among: 2'-F, 2'-OMe, 2'-MOE, cEt, LNA, morpholino, and modified morpholino.

Embodiment 144

The compound of any of embodiments 136 to 143, wherein the modified nucleosides of the modified region each comprise the same modification as one another.

Embodiment 145

The compound of embodiment 144, wherein the modified nucleosides of the modified region each comprise the same 2'-substituted sugar moiety.

Embodiment 146

The compound of embodiment 144, wherein the 2'-substituted sugar moiety of the modified nucleosides of the region of modified nucleosides is selected from 2'-F, 2'-OMe, and 2'-MOE.

Embodiment 147

The compound of embodiment 144, wherein the 2'-substituted sugar moiety of the modified nucleosides of the region of modified nucleosides is 2'-MOE.

Embodiment 148

The compound of embodiment 144, wherein the modified nucleosides of the region of modified nucleosides each comprise the same bicyclic sugar moiety.

Embodiment 149

The compound of embodiment 148, wherein the bicyclic sugar moiety of the modified nucleosides of the region of modified nucleosides is selected from LNA and cEt.

Embodiment 150

The compound of embodiment 144, wherein the modified nucleosides of the region of modified nucleosides each comprises a sugar surrogate.

Embodiment 151

The compound of embodiment 150, wherein the sugar surrogate of the modified nucleosides of the region of modified nucleosides is a morpholino.

Embodiment 152

The compound of embodiment 150, wherein the sugar surrogate of the modified nucleosides of the region of modified nucleosides is a modified morpholino.

Embodiment 153

The compound of any of embodiments 95 to 152, wherein the modified nucleotide comprises no more than 4 contiguous naturally occurring nucleosides.

Embodiment 154

The compound of any of embodiments 95 to 152, wherein each nucleoside of the modified oligonucleotide is a modified nucleoside.

Embodiment 155

The compound of embodiment 154, wherein each modified nucleoside comprises a modified sugar moiety.

Embodiment 156

The compound of embodiment 155, wherein the modified nucleosides of the modified oligonucleotide comprise the same modification as one another.

Embodiment 157

The compound of embodiment 156, wherein the modified nucleosides of the modified oligonucleotide each comprise the same 2'-substituted sugar moiety.

Embodiment 158

The compound of embodiment 157, wherein the 2'-substituted sugar moiety of the modified oligonucleotide is selected from 2'-F, 2'-OMe, and 2'-MOE.

Embodiment 159

The compound of embodiment 157, wherein the 2'-substituted sugar moiety of the modified oligonucleotide is 2'-MOE.

Embodiment 160

The compound of embodiment 158, wherein the modified nucleosides of the modified oligonucleotide each comprise the same bicyclic sugar moiety.

Embodiment 161

The compound of embodiment 160, wherein the bicyclic sugar moiety of the modified oligonucleotide is selected from LNA and cEt.

Embodiment 162

The compound of embodiment 156, wherein the modified nucleosides of the modified oligonucleotide each comprises a sugar surrogate.

Embodiment 163

The compound of embodiment 162, wherein the sugar surrogate of the modified oligonucleotide is a morpholino.

Embodiment 164

The compound of embodiment 162, wherein the sugar surrogate of the modified oligonucleotide is a modified morpholino.

Embodiment 165

The compound of any of embodiments 95 to 164, wherein the modified oligonucleotide comprises at least one modified internucleoside linkage.

Embodiment 166

The compound of embodiment 165, wherein each internucleoside linkage is a modified internucleoside linkage.

Embodiment 167

The compound of embodiment 165 or 166, comprising at least one phosphorothioate internucleoside linkage.

Embodiment 168

The compound of embodiment 166, wherein each internucleoside linkage is a modified internucleoside linkage and wherein each internucleoside linkage comprises the same modification.

Embodiment 169

The compound of embodiment 168, wherein each internucleoside linkage is a phosphorothioate internucleoside linkage.

Embodiment 170

The compound of any of embodiments 95 to 169, comprising at least one conjugate.

Embodiment 171

The compound of any of embodiments 95 to 170, consisting of the modified oligonucleotide.

Embodiment 172

The compound of any of embodiments 95 to 171, wherein the compound modulates splicing of the LRRK2 transcript.

Embodiment 173

A pharmaceutical composition comprising a compound according to any of embodiments 95 to 172 and a pharmaceutically acceptable carrier or diluent.

Embodiment 174

The pharmaceutical composition of embodiment 173, wherein the pharmaceutically acceptable carrier or diluent is sterile saline.

Embodiment 175

A method of modulating splicing of a LRRK2 transcript in a cell comprising contacting the cell with a compound according to any of embodiments 95 to 174.

Embodiment 176

The method of embodiment 175, wherein the cell is in vitro.

Embodiment 177

The method of embodiment 175, wherein the cell is in an animal.

Embodiment 178

The method of any of embodiments 175 to 177, wherein the amount of LRRK2 mRNA without exon 2 is increased.

Embodiment 179

The method of any of embodiments 175 to 177, wherein the amount of LRRK2 mRNA without exon 31 is increased.

Embodiment 180

The method of any of embodiments 175 to 177, wherein the amount of LRRK2 mRNA with exon 41 is increased.

Embodiment 181

The method of any of embodiments 175 to 180, wherein the LRRK2 transcript is transcribed from a LRRK2 gene.

Embodiment 182

A method of modulating the expression of LRRK2 in a cell, comprising contacting the cell with a compound according to any of embodiments 95 to 174.

Embodiment 183

The method of embodiment 182, wherein the cell is in vitro.

Embodiment 184

The method of embodiment 182, wherein the cell is in an animal.

Embodiment 185

A method comprising administering the compound of any of embodiments 95 to 172 to an animal.

Embodiment 186

The method of embodiment 185, wherein the administering step comprises delivering to the animal by intracerebroventricular injection, inhalation, parenteral injection or infusion, oral, subcutaneous or intramuscular injection, buccal, transdermal, transmucosal and topical.

Embodiment 187

The method of embodiment 185, wherein the administration is intracerebroventricular injection.

Embodiment 188

The method of any of embodiments 185 to 187, wherein the animal has one or more symptoms associated with Parkinson's disease.

Embodiment 189

The method of any of embodiments 185 to 187, wherein the administration results in amelioration of at least one symptom of Parkinson's disease.

Embodiment 190

The method of any of embodiments 185 to 189, wherein the animal is a human.

Embodiment 191

A method of preventing or slowing one or more symptoms associated with Parkinson's disease, comprising administering the compound according to any of embodiments 95 to 172 to an animal in need thereof.

Embodiment 192

The method of embodiment 191, wherein the animal is a human.

Embodiment 193

Use of the compound according to any of embodiments 95 to 172 for the preparation of a medicament for use in the treatment of Parkinson's disease.

Embodiment 194

Use of the compound according to any of embodiments 95 to 172 for the preparation of a medicament for use in the amelioration of one or more symptoms associated with Parkinson's disease.

Embodiment 195

Use of the compound according to any of embodiments 95 to 172 for the preparation of a medicament for use in the amelioration of one or more symptoms associated with Parkinson's disease.

These and other features and advantages of the present disclosure will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

A better understanding of the disclosure may be obtained in light of the following drawings which are set forth for illustrative purposes, and should not be construed as limiting the scope of the disclosure in any way.

FIG. 3A demonstrates that antisense oligonucleotides (ASO-41-1) successfully induces skipping of LRRK2 exon 41 containing the G2019S mutation in neurons derived from human induced pluripotent stem cells.

FIG. 4B shows quantification of the percentage of exon 41 skipped when compared to the amount of the full length LRRK2 RNA product per treatment condition. Treatment conditions: 41 1x-single treatment of cells with exon 41 ASO, 41 2x-double treatment of cells with exon 41 ASO, 41-FL 1x-single treatment of cells with exon 41 Fluorescent ASO, 41 2x-double treatment of cells with exon 41 Fluorescent ASO, Ctl-FL 2x-double treatment of cells with non-target Fluorescent ASO, Ctl 2x-double treatment of cells with non-target Fluorescent ASO. Results demonstrate that LRRK2 exon 41 skipping induced by antisense oligonucleotides (ASO) in iPS-derived neurons derived from healthy subject controls (CTRL 10A and 21.31) or PD patients carrying LRRK2 G2019S mutation (G2019S 29F and PD28).

FIG. 5A shows intracellular calcium levels were not altered in human iPS neurons carrying LRRK2 G2019S mutation compared to healthy subject (HS) controls. Detailed analysis showed no differences in the 1st and the 2nd calcium peak amplitude upon KCl depolarization (arrows). Additionally, no difference was observed in calcium buffering upon a prolonged KCl depolarization indicating no difference in the binding and compartmentalization of the unbound calcium. Results demonstrate iPS-derived neurons carrying LRRK2 G2019S mutation show altered calcium homeostasis after ER calcium pump Serca inhibition, which can be rescued by LRRK2 G2019S antisense oligonucleotide.

FIG. 5B shows intracellular calcium levels were not altered in human iPS neurons carrying LRRK2 G2019S mutation compared to healthy subject (HS) controls. Detailed analysis showed no differences in the 1st and the 2nd calcium peak amplitude upon KCl depolarization (arrows). Additionally, no difference was observed in calcium buffering upon a prolonged KCl depolarization indicating no difference in the binding and compartmentalization of the unbound calcium. Results demonstrate iPS-derived neurons carrying LRRK2 G2019S mutation show altered calcium homeostasis after ER calcium pump Serca inhibition, which can be rescued by LRRK2 G2019S antisense oligonucleotide.

FIG. 5C shows that upon Serca inhibition with 10 nM thapsigargin (THP), intracellular calcium levels were significantly increased in human iPS neurons carrying LRRK2 G2019S mutation compared to HS control. Detailed analysis showed an increase in the 2nd calcium peak amplitude upon KCl depolarization and an increase in the unbound calcium levels indicating decreased calcium buffering. Results demonstrate iPS-derived neurons carrying LRRK2 G2019S mutation show altered calcium homeostasis after ER calcium pump Serca inhibition, which can be rescued by LRRK2 G2019S antisense oligonucleotide.

FIG. 6A shows total ER-calcium levels were significantly decreased in the iPS midbrain neurons carrying LRRK2 G2019S mutation compared to the healthy subject control at baseline. Neurons were treated with non-target negative control ASO (NT ASO). This decrease in the ER calcium levels in the LRRK2 midbrain neurons was rescued with the G2019S exon 41 antisense oligonucleotide (G2019S ASO). ER calcium levels were measured by total CEPIA-ER-GFP expression emission. Results demonstrate that iPS-derived midbrain neurons carrying LRRK2 G2019S mutation show decreased total ER-calcium levels, which can be partially rescued by antisense oligonucleotide induced exon 41 skipping. Statistical analysis was performed using unpaired student T-test. ****p<0.0001

FIG. 6B shows total ER-calcium levels were 20% significantly decreased in the NT ASO treated iPS midbrain neurons carrying LRRK2 G2019S mutation compared to the healthy subject control after 24h of 10 nM thapsigargin induced Serca inhibition. Upon treatment with the G2019S ASO, total ER-calcium levels in the LRRK2 midbrain neurons were 11% significantly lowered compared to the NT treated HS neurons suggesting a partial rescue of the ER calcium levels by the G2019S ASO. Data was collected from one PD patient iPS-derived line carrying LRRK2 G2019S mutation and one healthy subject control line with the direct control over the ASO treatment (NT vs G2019S); each neuronal genotype represents a pool of 3 technical replicates quantifying more than 100 neurons per each condition. ER calcium levels were measured by total CEPIA-ER-GFP expression emission. Results demonstrate that iPS-derived midbrain neurons carrying LRRK2 G2019S mutation show decreased total ER-calcium levels, which can be partially rescued by antisense oligonucleotide induced exon 41 skipping. Statistical analysis was performed using unpaired student T-test. ****p<0.0001.

FIG. 8C shows the nitric oxide levels in LRRK2 G2019S iPS-derived neurons treated with exon 41 ASO (SEQ ID NO:02) and exon 31 ASO (SEQ ID NO:01). *p<0.05.

FIG. 9A shows the DAF-FM fluorescence intensity in T4.6 cell lines demonstrating that nitric oxide levels are lower in LRRK2 G2019S gene corrected iPS neurons.

FIG. 9B shows the DAF-FM fluorescence intensity in T4.13 cell lines demonstrating that nitric oxide levels are lower in LRRK2 G2019S gene corrected iPS neurons.

FIG. 9C shows the DAF-FM fluorescence intensity in IM1 cell lines demonstrating that nitric oxide levels are lower in LRRK2 G2019S gene corrected iPS neurons.

FIG. 11A shows the MitoTracker® confluence in iPS control cells and that disruption of mitochondrial intracellular distribution in iPS-derived neurons after mitochondrial depolarization.

FIG. 12A shows the MitoTracker® distribution in iPS LRRK2 G2019S neuron cells and healthy control cells after 2 uM valinomycin toxicity. Demonstrates altered mitochondrial intracellular distribution in LRRK2 G2019S iPS-derived neurons after mitochondrial depolarization induced by valinomycin toxicity compared to healthy control neurons.

FIG. 12B shows the MitoTracker® distribution in iPS LRRK2 G2019S neuron cells and gene corrected neurons after 2 uM valinomycin toxicity. Demonstrates trend towards altered mitochondrial intracellular distribution in LRRK2 G2019S iPS-derived neurons after mitochondrial depolarization induced by valinomycin toxicity.

FIG. 13B shows the ERSE transcriptional activity in control and PD LRRK2 G2019S cells and the decreased ER stress response in LRRK2 G2019S neurons. 2-way ANOVA indicates genotype significance for all comparisons. Results demonstrate that the ER stress response has lower activation threshold in LRRK2 G2019S human neurons compared to healthy subject neurons after calcium store depletion induced by thapsigargin (THP).

FIG. 13C shows the ATF6 transcriptional activity in control and PD LRRK2 G2019S cells and the decreased ER stress response in LRRK2 G2019S neurons. 2-way ANOVA indicates genotype significance for all comparisons. Results demonstrate that the ER stress response has lower activation threshold in LRRK2 G2019S human neurons compared to healthy subject neurons after calcium store depletion induced by thapsigargin (THP).

FIG. 14C shows mitophagy measured with Rosella bioprobe in healthy subject iPS-derived neurons. Results demonstrate that mitophagy can be successfully detected in healthy subject control human iPS neurons treated with 1 μM rotenone using live cell imaging of Rosella bioprobe (indicated by lower levels of the Green/Red fluorescent ratio).

FIG. 15 is a schematic of the antisense oligonucleotides (ASOs) designed to block splicing to either exon 2 or exon 4 in patients carrying a LRRK2 R1441C and/or a LRRK2 G2019S mutation. ASOs that block splicing of exon 2 or exon 4 will result in a frame-shift in the LRRK2 mRNA and protein product, which will essentially eliminate LRRK2 expression. Both of the ASO-induced LRRK2 mRNA transcripts are predicted to mitigate disease symptoms by lessening the toxic effects of the mutated LRRK2 protein.

FIG. 18 shows that ASOs directed to exon 41 induce dose responsive exon 41 skipping in fibroblast cells isolated from a patient having a LRRK2 G2019S mutation. Cells were treated with 7.5 μM, 15 μM, 22.5 μM, or 45 μM of each ASO: ASO-6 (AGACAGACCTGATCACCTACCTGGT; SEQ ID NO:02, targeting exon 41), or ASO-46 (GGTATCT-GCCAGAAAATGCACAGGA; SEQ ID NO:08, targeting exon 41).

FIG. 21 shows that an ASO specific to the LRRK2 G2019S mutation can induce exon 41 skipping in fibroblast cells isolated from a patient having a LRRK2 G2019S mutation. Cells were treated with 7.5 μM of each ASO: ASO-284 (AATGCTGTAGTCAGCAATCTTTGCA; SEQ ID NO:09, targeting the LRRK2 G2019S mutation), ASO-6 (AGACAGACCTGATCACCTACCTGGT; SEQ ID NO:02, targeting exon 41).

FIG. 32A shows a decrease in LRRK2 protein expression in HS fibroblasts and PD patient derived fibroblasts carrying the LRRK2 G2019S mutation when treated with ASOs targeting exon 41 or exon 2. Treatment with 1 μM or 15 μM of ASO#6, or 15 μM of ASO#45 results in a decrease in LRRK2 protein levels. One way ANOVA with Dunnett's multiple testing correction; *p<0.05.

FIG. 33 shows changes in phosphorylated LRRK2 protein levels (phosphorylation at Serine 935) in HS fibroblasts and PD patient derived fibroblasts carrying the LRRK2 G2019S mutation when treated with ASOs targeting exon 41 or exon 2. Treatment with 1 μM or 15 of ASO#6, or 15 μM of ASO#45 results in a change in phosphorylated LRRK2 protein levels.

FIG. 36 shows changes in phosphorylated LRRK2 protein levels (phosphorylation at Serine 935) in PD patient derived fibroblasts carrying the LRRK2 R1441C mutation when treated with ASOs targeting exon 31 or exon 2 (treatment with 5 μM of ASO#5 or 5 μM of ASO#45).

FIG. 38A shows that ASOs directed to exon 41 induce exon 41 skipping in iPS-derived neurons with WT LRRK2 or LRRK2 carrying the G2019S mutation. Cells were treated with 2×10 μM of an ASO specific to exon 41 (ASO#6; SEQ ID NO:02).

FIG. 39A shows that antisense oligonucleotides treatment of iPS-derived neurons with an ASO targeting exon 31 successfully induces skipping of LRRK2 exon 31. Cells were treated with 10 μM, 17.5 μM, or 25 μM of an ASO specific to exon 31 (ASO#5; SEQ ID NO:01).

FIG. 39B shows quantification of the percentage of exon 31 skipped when treated with an ASO targeting exon 31. Cells were treated with 10 μM, 17.5 μM, or 25 μM of an ASO specific to exon 31 (ASO#5; SEQ ID NO:01).

Figure 1:
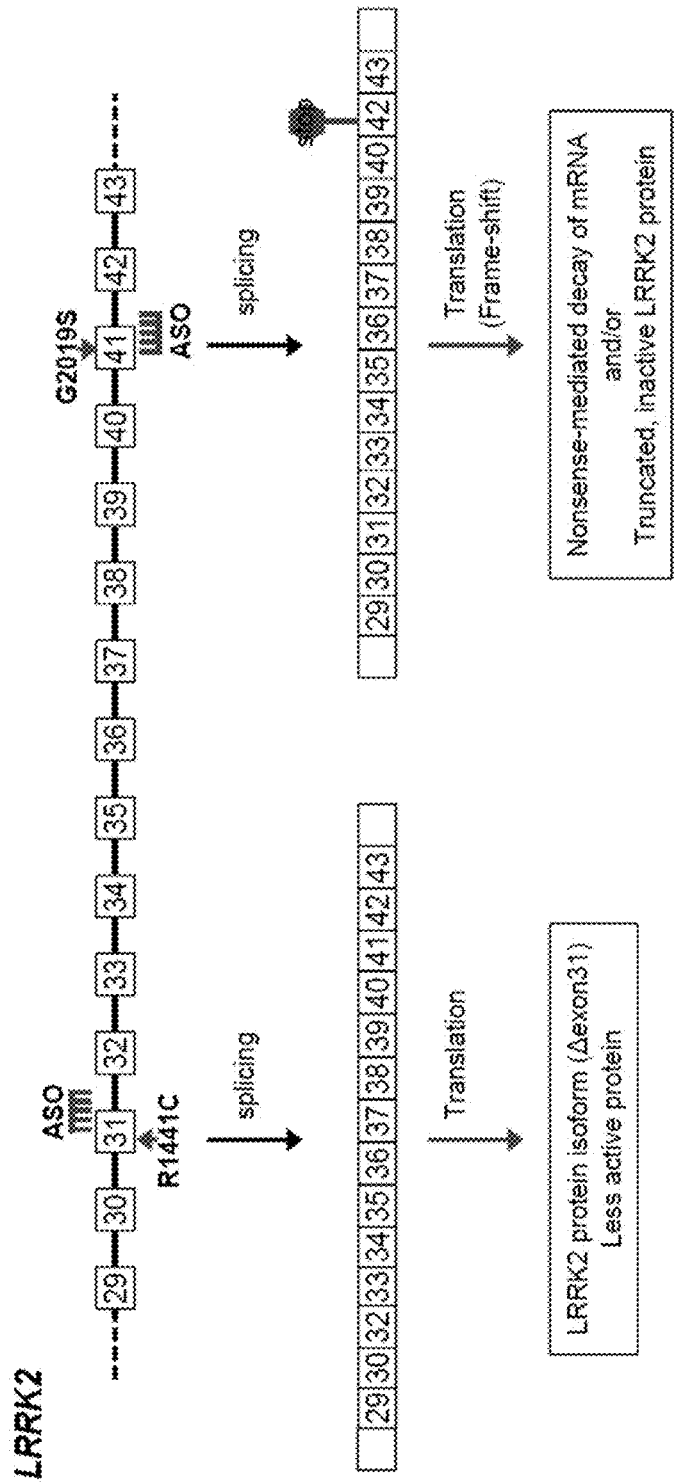
FIG. 1 is a schematic of the antisense oligonucleotides (ASOs) designed to block splicing to either exon 31 in patients with a LRRK2 R1441C mutation or exon 41 in patients with a G2019S mutation. ASOs that block splicing of exon 41 will result in a frame-shift in the LRRK2 mRNA and protein product, which will essentially eliminate LRRK2 expression. ASOs that block splicing of exon 31 will eliminate the R1441C mutation and result in the production of an alternative LRRK2 isoform predicted to have lower kinase activity. Both of the ASO-induced LRRK2 mRNA transcripts are predicted to mitigate disease symptoms by lessening the toxic effects of the mutated LRRK2 protein.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present disclosure.

DETAILED DESCRIPTION OF THE DISCLOSURE

The present disclosure relates to general compounds and methods to treat Parkinson's disease in subjects using antisense oligonucleotides (ASOs) that induce specific pre-mRNA splicing events in LRRK2 gene transcripts that result in mRNAs that code for proteins that fully or partially restore the function of LRRK2 (i.e., resulting in increased levels of correctly localized LRRK2 protein at the plasma membrane and with increased function). For example, some ASOs can base-pair with the target RNA and correct aberrant splicing caused by mutations, and other ASOs can induce skipping of exons with mutations that cause open reading frame-shifts. In such instances, skipping of the mutated exon using ASOs can restore the reading frame and generate an mRNA that codes for a LRRK2 isoform with partial function.

ASOs have been effectively used to alter pre-mRNA splicing (for review, Aartsma-Rus & van Ommen 2007; Smith et al., 2006). For example, ASOs targeted to cryptic splice sites created by mutations in the ATM gene were recently demonstrated to effectively redirect splicing to the correct splice site and improve protein expression (Du et al., 2007). The first clinical trials based on ASO-induced skipping of exons as a therapy for Duchenne muscular dystrophy (DMD) have shown success in increasing dystrophin protein levels in muscle cells surrounding the site of injection (van Deutekom et al., 2008). ASO-based therapies may provide a customizable approach to mutation-based treatments for disease. The effectiveness of ASOs in modulating splicing in a therapeutically beneficial manner has been demonstrated for a number of diseases.

In an embodiment, this disclosure provides a therapeutic treatment of human subjects having Parkinson's Disease by administering to the human subject an ASO oligonucleotide having 8 to 30 linked nucleosides having a nucleobase sequence comprising a complementary region comprising at least 8 contiguous nucleobases complementary to a target region of equal length within an LRRK2 transcript. In an embodiment, the ASO may target exon 2, exon 4, exon 31 or exon 41 of an LRRK2 transcript. More specifically, suitable ASOs will bind consecutive nucleotides of exon 31 or exon 41 of LRRK2 via complementary base-pairing interactions and have a length of 8 to 30 nucleotides, more preferably 15 to 30 nucleotides, even more preferably 15 to 27 nucleotides and most preferably 15-25 nucleotides or any range or combination of ranges therein. The ASOs targeting exon 2 or exon 4 induce exon 2 or exon 4 skipping, respectively, which will disrupt the LRRK2 reading frame and result in a truncated LRRK2 protein. Thus, exon 2 or exon 4 skipping induced by the ASO results in an overall reduction in LRRK2 protein. The ASOs successfully reduce full-length LRRK2 expression by inducing skipping of LRRK2 exon 31 and 41 containing LRRK2 with the R1441C or G2019S mutation, respectively.

The LRRK2 gene encodes a member of the leucine-rich repeat kinase family and encodes a protein with an ankryin repeat region, a leucine-rich repeat (LRR) domain, a kinase domain, a DFG-like motif, a RAS domain, a GTPase domain, a MLK-like domain, and a WD40 domain. The protein is present largely in the cytoplasm but also associates with the mitochondrial outer membrane. Mutations in LRRK2 are the most common known cause of familial and sporadic PD, accounting for approximately 5% of individuals with a family history of the disease and 3% of sporadic cases. It has been suggested that the G2019S mutation in LRRK2 results in stabilization of microtubules by tubulin-beta phosphorylation and may represent a physiologic function of LRRK2 in neurons. Phosphorylation of tubulin was enhanced 3-fold by the LRRK2 G2019S mutation (i.e, a gain of function mutation), which suggested that mutant LRRK2-induced neurodegeneration in PD may be partly mediated by increased phosphorylation of tubulin-beta, which may interfere with neurite outgrowth, axonal transport, and synapse formation.

Human (*Homo sapiens*) leucine-rich repeat kinase 2 (LRRK2) is located on chromosome 12 (genomic coordinates (GRCh38): 12:40,224,894-40,369,284). The gene is 9239 bp mRNA (RefSeq Gene ID: 120892; Official Symbol: LRRK2; Official Full Name: leucine rich repeat kinase 2) and is assigned NCBI Reference Sequence: NM_198578.3 (SEQ ID NO: 3); ACCESSION: NM_198578; Ensembl: ENSG00000188906. LRRK2 is also known as: PARKS; RIPK7; ROCO2; AURA17; DARDARIN; FLJ45829; DKFZp434H2111. Human LRRK2 protein is assigned NCBI Reference Sequence: NP_940980.3 (2527 aa; SEQ ID NO: 4).

Antisense compounds, (e.g. antisense oligonucleotides (ASOs)) have been used to modulate target nucleic acids. Antisense compounds comprising a variety of chemical modifications and motifs have been reported. In certain instances, such compounds are useful as research tools, diagnostic reagents, and as therapeutic agents. In certain instances, antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Pre-mRNA splicing involves the precise and accurate removal of introns from the pre-messenger RNA and the ligation of exons together after intron removal to generate the mature mRNA which serves as the template for protein translation. Pre-mRNA splicing is a two-step reaction carried out by a spliceosome complex comprising protein and small RNA components which recognize conserved sequence elements within the introns and exons of the RNA. Recognition of these sequence elements, including the 5' splice site, 3' splice site and branch point sequence, is the primary mechanism directing the correct removal of introns.

Splicing requires direct base-pairing between small nuclear RNA (snRNA) components of the spliceosome and the splice site nucleotides of the mRNA. This interaction can be disrupted by gene mutations or by artificial blocking using short oligonucleotides complementary to the RNA. Such so called antisense oligonucleotides (ASOs), when designed to be complementary to a splice sites, will compete for base-pairing with the snRNAs, thereby blocking an essential step in splicing at the site. In this way, antisense oligonucleotides can potently block unwanted splicing or redirect splicing to alternative splice sites, and can result in mRNAs that code for proteins that fully or partially restore the function to target transcripts. For example, antisense oligonucleotides (ASOs) can be designed to block splicing to either exon 31 in patients with a LRRK2 R1441C mutation or exon 41 in patients with a G2019S mutation. ASOs that block splicing of exon 41 will result in a frame-shift in the LRRK2 mRNA and protein product, which will essentially eliminate LRRK2 expression. ASOs that block splicing of exon 31 will eliminate the R1441C mutation and result in the production of an alternative LRRK2 isoform predicted to have lower kinase activity. Both of the ASO-induced LRRK2 mRNA transcripts are predicted to mitigate disease symptoms by lessening the toxic effects of the mutated LRRK2 protein.

For example, ASOs can target the GLY2019SER (G2019S) mutation in exon 41 of the LRRK2 gene. This mutation in LRRK2 is the most common known cause of familial and sporadic PD, accounting for approximately 5% of individuals with a family history of the disease and 3% of sporadic cases. The G2019S mutation lies within the mixed-lineage kinase-like domain, and does not appear to alter the steady-state level, turnover, or intracellular localization of the LRRK2 protein, but the G2019S mutation appears to enhance protein kinase activity in a dominant negative fashion. ASOs that block splicing of exon 41 will result in a frame-shift in the LRRK2 mRNA and protein product, which will essentially eliminate LRRK2 expression and mitigate PD symptoms by lessening the toxic effects of mutated LRRK2 protein. Non-limiting examples of an ASO that prevents splicing of exon 41 are:

SEQ ID NO:02 (5'-AGACAGACCTGATCACCTAC-CTGGT-3'),

SEQ ID NO:08 (5'-GGTATCTGCCAGAAAATGCACA-GGA-3'), or

SEQ ID NO:09 (5'-AATGCTGTAGTCAGCAATCTTT-GCA-3').

In another non-limiting example, ASOs can target the ILE2020THR (I2020T) mutation in exon 41 of the LRRK2 gene. The I2020T mutation in LRRK2 has been found in PD patients. The I2020T mutation mutant protein shows significantly increased (about 40%) autophosphorylation activity compared to wildtype LRRK2, consistent with a gain of function. ASOs that block splicing of exon 41 will result in a frame-shift in the LRRK2 mRNA and protein product, which will essentially eliminate LRRK2 expression and mitigate PD symptoms by lessening the toxic effects of mutated LRRK2 protein.

In yet another non-limiting example, antisense oligonucleotides can target the ARG1441CYS (R1441C) mutation in exon 31 of the LRRK2 gene. This mutation has been observed in patients with Parkinson's disease. The R1441C mutation lies within the GTPase domain of LRRK2, and does not appear to alter the steady-state level, turnover, or intracellular localization of the LRRK2 protein, but the R1441C mutation appears to enhance protein kinase activity. ASOs that block splicing of exon 31 will eliminate the R1441C mutation and result in the production of an alternative LRRK2 isoform predicted to have lower kinase activity, which should mitigate disease symptoms by lessening the toxic effects of the mutated LRRK2 protein. A non-limiting example of an ASO that prevents splicing of exon 31 is SEQ ID NO:01 (5'-CTACCAGCCTACCATGT-TACCTTGA-3').

In another non-limiting example, antisense oligonucleotides can target the ARG1441HIS (R1441H) mutation in exon 31 of the LRRK2 gene. The R1441H mutation was found in PD patients. ASOs that block splicing of exon 31 will eliminate the R1441H mutation and result in the production of an alternative LRRK2 isoform predicted to have lower kinase activity, which should mitigate disease symptoms by lessening the toxic effects of the mutated LRRK2 protein.

In another non-limiting example, antisense oligonucleotides can target the ARG1441GLY (R1441G) mutation in exon 31 of the LRRK2 gene. The R1441G mutation was found in 13.15% of 418 PD patients from the Basque region. ASOs that block splicing of exon 31 will eliminate the R1441G mutation and result in the production of an alternative LRRK2 isoform predicted to have lower kinase activity, which should mitigate disease symptoms by lessening the toxic effects of the mutated LRRK2 protein.

In yet another non-limiting example, the ASOs can target exon 2 or exon 4, and induce exon 2 or exon 4 skipping, respectively, which will disrupt the LRRK2 reading frame and result in a truncated LRRK2 protein. Thus, exon 2 or exon 4 skipping induced by the ASO results in an overall reduction in LRRK2 protein. A non-limiting example of an ASO targeting exon 2 is SEQ ID NO:07 (5'-AGT-GAAAACAATGCCTTTACCTGCT-3'). A non-limiting example of an ASO targeting exon 4 is SEQ ID NO:06 (5'-ATACACATATTACCTGAAGTTAGGA-3'). Also see FIG. 15.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "antisense compound" or "antisense oligonucleotide (ASO)" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to, furanosyls comprising substituents at the 2'-position, the 3'-position, the 5'-position and/or the 4'-position.

As used herein, "2'-substituted sugar moiety" means a furanosyl comprising a substituent at the 2'-position other than —H or —OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring).

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments, the 4 to 7 membered ring is a furanosyl. In certain such embodiments, the bridge connects the 2'-carbon and the 4'-carbon of the furanosyl.

As used herein, the term "sugar surrogate" means a structure that does not comprise a furanosyl and that is capable of replacing the naturally occurring sugar moiety of a nucleoside, such that the resulting nucleoside is capable of: (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used here, the term "morpholino" means a sugar surrogate having the following structure:

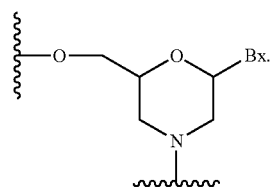

In certain embodiments, morpholinos may be modified, for example by adding or altering various substituent groups from the above morpholino structure. Such sugar surrogates are referred to herein as "modified morpholinos." Morpholino comprising compositions are described in U.S. Pat. Nos. 5,142,047 and 5,185,444, incorporated by reference in their entirety. In other embodiments, morpholinos may be unmodified. For example, the structure of an unmodified oligonucleotide is:

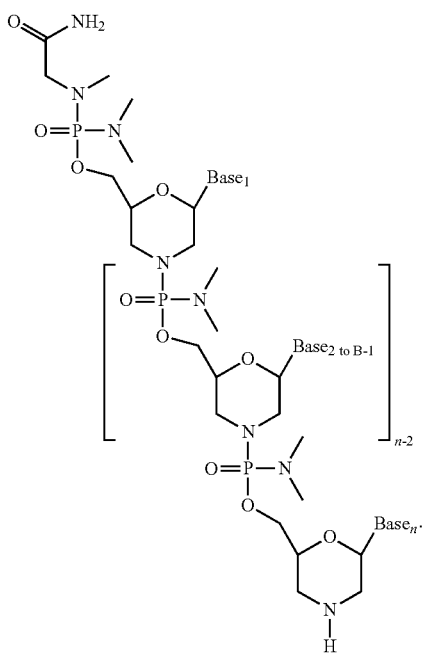

Combinations of modifications are also provided without limitation, such as 2'-F-5'-methyl substituted nucleosides (see WO 2008/101157 for other disclosed 5',2'-bis substituted nucleosides) and replacement of the ribosyl ring oxygen atom with S and further substitution at the 2'-position (see U.S. Patent Application US2005-0130923,) or alternatively 5'-substitution of a bicyclic nucleic acid (see WO 2007/134181, wherein a 4'-CH.sub.2-O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "nucleotide" means a nucleoside further comprising a phosphate linking group.

As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein, the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)-O-2'bridge.

As used herein, "locked nucleic acid nucleoside" or "LNA" means a nucleoside comprising a bicyclic sugar moiety comprising a 4'-CH$_2$-O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more substructures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to, pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, 20 or 25 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleotides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment. Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett,* 1990, 259, 327-330; Svinarchuk et al., *Biochimie,* 1993, 75, 49-54), a phospholipid, e.g., di-hexadecyl-rac-glycerol or triethyl-ammonium 1,2-di-0-hexadecyl-rac-glycero-3-H-phosphonate (Manoharan et al., *Tetrahedron Lett.,* 1995, 36:3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36:3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some non-limiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_2$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Pharmaceutical Compositions

In certain embodiments, the present invention provides pharmaceutical compositions comprising one or more antisense compound. The pharmaceutical composition may comprise a cocktail of antisense compounds, wherein the cocktail comprises 2, 3, 4, 5, 6, 7, 8, 9, 10 or more antisense compounds. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations.

Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide (DMSO) are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human. In certain embodiments, the animal is a mouse.

In certain embodiments, the present invention provides methods of administering a pharmaceutical composition comprising an oligomeric compound of the present invention to an animal. Suitable administration routes include, but are not limited to, oral, rectal, transmucosal, transdermal, intestinal, enteral, topical, suppository, through inhalation, intrathecal, intracerebroventricular, intraperitoneal, intranasal, intratumoral, and parenteral (e.g., intravenous, intramuscular, intramedullary, and subcutaneous). In certain embodiments, a pharmaceutical composition is prepared for intracerebroventricular administration or intracerebroventricular injection. In such embodiments penetrants appropriate to the blood-brain barrier to be permeated are used in the formulation. Such penetrants are generally known in the art. In certain embodiments, pharmaceutical compositions are administered to achieve local rather than systemic exposures.

In certain embodiments, a pharmaceutical composition is administered to an animal having at least one symptom associated with Parkinson's disease. In some embodiments, the animal has a mutation in the LRRK2 gene and protein encoded by the mutated gene. Non-limiting examples of such mutants include, but are not limited to, G2019S, I2020T, R1441C, R1441H, or R1141G. In other embodiments, the mutation can be any mutation in LRRK2 associated with Parkinson's disease. In certain embodiments, such administration results in amelioration of at least one symptom. In certain embodiments, administration of a pharmaceutical composition to an animal results in an increase in functional LRRK2 protein in a cell. In certain embodiments, the administration of certain antisense oligonucleotides (ASOs) delays the onset of Parkinson's disease. In certain embodiments, the administration of certain antisense oligonucleotides prevents the onset of Parkinson's disease. In certain embodiments, the administration of certain antisense oligonucleotides rescues cellular phenotype.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence

EXAMPLES

The Examples that follow are illustrative of specific embodiments of the invention, and various uses thereof. They are set forth for explanatory purposes only, and are not to be taken as limiting the invention.

Methods

Antisense Oligonucleotides (ASOs).

ASOs were filtered, selectively precipitated, resuspended in pure water, and freeze dried to remove all contaminants. No acids or salts were used in purification. ASOs with phosphorodiamidate morpholino (PMO) chemistries were generated by GeneTools LLC and were dissolved in 0.9% saline.

Cell Culture and Transfection.

Primary fibroblast cell lines established from non-disease (Healthy Subject (HS) Control; CTRL) or a Parkinson's disease patient (G2019S or R1441C) skin biopsy were transfected with ASOs (1.0 µM, 5 µM, 7.5 µM, 15 µM, 22.5 µM, or 45 µM final concentration) using Endo-Porter transfection reagent (GeneTools) according to manufacturer's protocol (see "Endo-Porter Delivery of Morpholino Oligos" from Gene Tools, LLC, 14 Sep. 2012, pages 1-4). RNA was collected 48 hours post-transfection. IPS-derived neurons were treated with the LRRK2 G2019S exon 41 anti-sense oligonucleotide with the sequence 5'-AGACAGACCTGAT-CACCTACCTGGT-3' (SEQ ID NO: 2) and a non-sense control oligonucleotide sequence 5'-CCTCTTACCTCAGT-TACAATTTATA-3' (SEQ ID NO: 5) either once (5 days post differentiation, DIV37) or two times (2 and 5 days post end of the differentiation (DIV37 and DIV41)). Each time neurons were treated with 10 µM LRRK2 ASOs using Endo-Porter delivery method according to the manufacturer's protocol (Gene Tools, 4 µl per 1 mL solution). Exon skipping efficiency was also assessed by comparing between the non-tag and the carboxyflourescein-3' tag ASO sequences. RNA was collected 48 hours post the second transfection (DIV43).

RNA Isolation and Analysis.

RNA was isolated from cells using TRIZOL™ reagent (Life Technologies, Carlsbad, Calif.) according to the manufacturer's protocol, followed by reverse transcription with GoScript™ reverse transcription system (Promega, Madison, Wis.). Radiolabeled PCR was carried out using primers specific for human LRRK2 region encompassing the ASO target exon. PCR products were separated by polyacrylamide gel electrophoresis and bands on gels were quantitated by densitometry analysis using Image J software or phosphorimage analysis using a TYPHOON™ phosphorimager.

Differentiation of Neurons from Human iPSCs.

Human induced pluripotent stem cells (iPS) cells derived from biopsied fibroblasts from Parkinson's patients and healthy subject controls (Cooper et al., 2012, "Pharmacological Rescue of Mitochondrial Deficits in iPSC-Derived Neural Cells from Patients with Familial Parkinson's Disease," Sci Transl Med. 2012, 4; 4(141):141ra90; see Table 1) were grown on a feeder layer of mouse embryonic fibroblasts (MEFs) (GlobalStem, GSC-6001G) in HESCM media consisting of DMEM/F-12 (Life Technologies, 11330-032), 20% Knockout Serum (Life Technologies, 10828-028), Penicillin-Streptomycin (Life Technologies, 15140-122), 1 mM L-Glutamine (Life Technologies, 25030-081), 55 µM β-Mercaptoethanol (Gibco, 21985-023), and MEM non-essential amino acids (Life Technologies, 11140-050). LRRK2 G2019S gene corrected iPSC lines were obtained from and previously characterized by Reinhardt et al., 2013, ("Genetic Correction of a LRRK2 Mutation in Human iPSCs Links Parkinsonian Neurodegeneration to ERK-Dependent Changes in Gene Expression." *Cell Stem Cell* 12, 354-367). Table 1 provides an overview of the iPS cell lines used.

TABLE 1

List of the human iPSC lines used in phenotypic assays

| Line Name | Genotype |
|---|---|
| 10A | Control (CTRL) |
| 21.31 | Control (CTRL) |
| 21.35 | Control (CTRL) |
| 9A | LRRK2 G2019S |
| 2F | LRRK2 R1441C |
| 3C | LRRK2 R1441C |
| PD28 | LRRK2 G2019S |
| PD28 Nurr1:GFP | LRRK2 G2019S |
| 29F | LRRK2 G2019S |
| T4.6Mut | LRRK2 G2019S |
| T4.13Mut | LRRK2 G2019S |
| IM1Mut | LRRK2 G2019S |
| IM2Mut | LRRK2 G2019S |
| T4.6.10GC | LRRK2 gene correction |
| T4.6.43GC | LRRK2 gene correction |
| T4.13.10GC | LRRK2 gene correction |
| IM1GC | LRRK2 gene correction |
| IM2GC | LRRK2 gene correction |

Embryoid Bodies (EB) Protocol for Generation of Neural Cells.

Neuronal cells were differentiated from induced pluripotent stem cells (iPSCs), following the procedures and modified from Brennand et al. 2011 ("Modeling schizophrenia using human induced pluripotent stem cells," *Nature*, 2011 May 12; 473(7346):221-5). In brief, iPSC colonies were dissociated using 1 mg/mL Collagenase IV (Life Technologies, 17104-019), resuspended in N2 GlutaMAX medium (DMEM GlutaMAX™, Life Technologies, 10565-042; N2, Life Technologies, 17502-048) supplemented with 100 nM LDN (Stemgent, 04-0074-02), and plated on low attachment 6 well plates (Corning, 3471) to initiate suspension culture of embryoid bodies. On DIV7 the embryoid bodies were replated for rosette formation onto 6 well plates (Corning, 353046) coated with poly-L-ornithine (PLO, 15% in PBS, Sigma, P4957) and mouse laminin (1 µg/mL in DMEM/F-12, Sigma, L2020) in the presence of N2 medium supplemented with 1 µg/mL laminin. On DIV 14, rosettes were cut manually and passaged onto new PLO-laminin coated plates for expansion in DMEM/F12 media supplemented with N2, B-27 (Life Technologies, 17504-044), 2 µg/mL human recombinant bFGF (Life Technologies, 13256-029) and 1 µg/mL laminin. The final neural differentiation phase was started by rosettes dissociation on DIV 21. Rosettes were dissociated using Accutase® (Millipore, SCR005) and plated onto PLO-laminin coated 6 well plates at a density of 300,000 cells per well in neural differentiation media containing DMEM/F12, N2 and B27 supplement, 1 mM dibutyry cyclic AMP (cAMP) (Enzo Life Sciences, BML-CN125-0100), 20 ng/mL BDNF (PreproTech, 450-02) and 200 µM Ascorbic acid (Sigma, A4034) (Neural Differentiation media). Cells were harvested on DIV 35 by dissociation using Accutase® for phenotypic assays.

Generation of Ventral Midbrain Dopaminergic Neurons.

Midbrain dopaminergic neuron differentiation was initiated following previously published protocols by Cooper et al., 2010 ("Differentiation of human ES and Parkinson's disease iPS cells into ventral midbrain dopaminergic neurons requires a high activity form of SHH, FGF8a and specific regionalization by retinoic acid," *Molecular and Cellular Neuroscience* 45, 258-266) and Sunberg et al., 2013 ("Improved Cell Therapy Protocols for Parkinson's disease based on differentiation efficiency and safety of hESC-, hiPSC-, and non-human primate iPSC-derived dopaminergic neurons," *Stem Cells*. 2013 August; 31(8):1548-62).

LRRK2-Specific Anti-Sense Oligonucleotide Treatment.

LRRK2 G2019S exon 41 anti-sense oligonucleotide sequence 5'-AGACAGACCTGATCACCTACCTGGT-3' (SEQ ID NO: 2) and a non-sense control oligo sequence 5'-CCTCTTACCTCAGTTACAATTTATA-3' (SEQ ID NO: 5) were administered to the neuronal culture at DIV 37 and 41. Each time neurons were treated with 10 µM LRRK2 ASOs using Endo-Porter delivery method according to the manufacturer's protocol (Gene Tools, 4 µl per ml). Depending on the experimental set up, ASOs with a carboxyflourescein tag were used when the visualization of the ASO in the cell was desired, emitting green-fluorescence at 524.5 nm.

Calcium Imaging

Total Intracellular Calcium Imaging Using Fura2.

iPS-derived neurons were grown on cover slips coated with 15% poly-L-ornithine/laminin in 24 well plates at 50,000 cells/well. Cell cultures were treated with ASOs at DIV 37 and DIV41 as described above. Cells were treated with 0 nM THP or 10 nM THP and imaged 24 hours later (either 7 days post-plating for 0 nM or 8 days post-plating for 10 nM treatment). iPS-neurons were incubated with 5 µM Fura2-AM (Molecular Probes, F1221) in differentiation medium for 30 minutes at room temperature (RT). Cells were imaged at RT in standard external solution (SES, Boston BioProducts, C-3030; 145 mM NaCl, 5 nM KCl, 2 nM CaCl2, 1 mM MgCl2, 10 mM Glucose, 10 mM HEPES, pH 7.4±0.15), using a Nikon Elipse Ti microscope with a Q-Imaging® CCD camera, at a 10× magnification (Plan Fluo objective, NA 0.30). To measure calcium regulation, influx was elicited with application of 50 mM KCl, according to the protocol described in Table 2.

TABLE 2

Live cell calcium imaging KCl application protocol

| Time | Solution applied |
|---|---|
| 0-1 minute | standard external solution (SES) |
| 1-1 minute 15 seconds | 50 mM KCl |
| 1 minute 15 seconds-5 minutes | SES |
| 5-11 minutes | 50 mM KCl |
| 11-13 minutes | SES |

Intracellular calcium levels were measured by taking the ratio of the Fura-2 emission wavelengths; 340 nm and 380 nm, with an exposure time of 600 ms and 300 ms respectively, acquiring images every 3 seconds. To identify ASO positive cells, one image in the first second was acquired at 525 nm (Tetramethylrhodamine; TRITC), with an exposure time of second. NIS Elements AR 3.2 imaging software (Nikon) was used to analyze the acquired images, outlining visually defined cells as regions of interest. The Fura-2 340 nm/380 nm ratio fluorescence was measured over time in the designated regions. The change in fluorescence was normalized to the baseline fluorescence prior to the first KCl stimulation. Cells with a minimum of 7% change from baseline during stimulation were considered active cells, and consequently included in further analyses. Two characteristics of calcium homeostasis were measured. Firstly, by analyzing the peak amplitude of intracellular calcium with the first and second KCl stimulation, representing immediate calcium influx through calcium channels and cytoplasmic calcium release from organelles such as the ER. Secondly, the area under the curve during prolonged depolarization, the second KCl application, was measured. During this state, unbound calcium is cleared by calcium-binding protein and ER calcium reuptake, allowing calcium levels reach an equilibrium. Buffering capacity is dependent on inactivation of calcium channels and reuptake of calcium by the ER and mitochondria.

ER-calcium imaging using the CEPIA-ER calcium indicator. To measure calcium levels specifically in the ER, a calcium-measuring organelle-entrapped protein indicator (CEPIA) was used (Suzuki et al. 2014, "Imaging intraorganellar Ca2+ at subcellular resolution using CEPIA," *Nature Communications,* 5:4153). This genetically encoded calcium indicator (GECI) contains an ER specific retention sequence, and has a binding affinity compatible with the sub-millimolar calcium levels detected in the ER with an emission wavelength of 511 nm. IPS-derived neurons were infected with the lentivirus encoding for CEPIA-ER-GFP under the synapsin promotor 24 hours post-plating, at an MOI of 20. Vehicle treated and 10 nM THP treated neurons where imaged at DIV 43 post-plating, 24 hours after the incubation with the vehicle/toxin. Images were acquired at 525 nm, with an exposure time of 800 milliseconds for mixed culture iPS-neurons and 1 second for midbrain iPS-neurons, with a second acquisition interval. To measure background bleaching, decay in GFP emission was measured in a non-stimulated trace, for every cell line. Change in fluorescence was corrected for bleaching by dividing the raw measurement point by the average fluorescence of non-stimulated cells for every individual acquired time point. ImageJ software was used to analyze the acquired images, where regions were determined and measured as stated earlier. Baseline ER levels were calculated based on the mean average of the GFP fluorescence levels between the first 15 and 55 seconds of imaging prior to the KCl. Only active neurons with a minimum of 2% change from baseline during KCl stimulation were considered active cells, and consequently included in the analyses.

Neurite Outgrowth.

After differentiation (DIV 35) EB iPS-derived neurons were replated into 96 well plates at 15,000 cells per well for live cell phase imaging of neurite outgrowth. If needed, on day 2 and day 5 post-plating, neurons were treated with 10 µM exon 41 ASO (SEQ ID NO:02) or non-target ASO (SEQ ID NO:05) conjugated to carboxyflourescein. Seven days post plating, on DIV 42, neurons were exposed to thapsigargin (THP) toxicity at 0 nM, 1 nM, 10 nM, and 100 nM concentration and the live cell imaging was started immediately using the IncuCyte® Zoom live imaging system (Essen BioScience) (see FIG. 7). Neurite length per cell body cluster was measured using the IncuCyte® imaging system. To evaluate the exon 41 ASO induced rescue on neurite length, the IncuCyte® ZOOM images were exported as tiff files and neurites from ASO-carboxyflourescein positive neurons were manually traced in Fiji ImageJ NeuronJ plugin. Total neurite length was then corrected for the number of the ASO+ neurons in each image. Images were randomized and blinded to the investigator.

Statistical Analysis.

Statistical significance was tested using Graphpad Prism 6 software (Graphpad software). 1-way, 2-way ANOVA and student T-test were used depending on the dataset. Statistical analysis was specified for each experiment in the figure legend.

Other Phenotypic Assays:

Mitochondrial Dysfunction Assays.

It was previously shown that human LRRK2 G2019S iPSC-derived neurons and human fibroblasts exhibit increased vulnerability to PD associated cell stressors and modified mitochondrial dynamics, which can be rescued by LRRK2 inhibitors (Cooper et al., 2012, "Pharmacological Rescue of Mitochondrial Deficits in iPSC-Derived Neural Cells from Patients with Familial Parkinson's Disease" *Sci Transl Med.* 2012, 4; 4(141):141ra90; Smidt et al., "Fibroblast Biomarkers of sporadic parkinson's disease and LRRK2 kinase inhibition," *Mol Neurobiol.* 2016 October; 53(8):5161-77).

Nitric Oxide and Super Oxide Live Cell Imaging.

DAF-FM is a cell permeant molecule, which upon reaction with nitric oxide (NO) forms a fluorescent benzotriazole, emitting green fluorescence at 515 nm (Molecular Probes). On DIV 43, 24 hours post valinomycin treatment at 0 µM (vehicle control), 2 µM, and 10 µM valinomycin (Sigma, v0627) dissolved in DMSO (Sigma, D2650-5X5ML), EB neurons were labeled with DAF-FM fluorescent probe (Molecular Probes, D-23844) at 5 µM in HBSS containing calcium and magnesium (Life Technologies, 14025-092) according to the manufacturer's protocol. The cells were immediately imaged using the IncuCyte® Zoom live imaging system and DAF-FM green fluorescence intensity was quantified.

MitoSOX™ is a molecule targeting mitochondria through triphenylphosphonium (Molecular Probes). MitoSOX™ is oxidized by super oxide, consequently emitting red fluorescence at 580 nm. 24 hours post valinomycin treatment EB neurons were labeled with the MitoSOX™ (Molecular Probes, M36008) fluorescent probe at 7.5 µM in HBSS for 30 minutes at 37° C. After three washes with HBSS, the cells were immediately imaged using the IncuCyte® Zoom live imaging system and MitoSox red fluorescence was quantified.

Mitochondrial Labeling with MitoTracker®.

At DIV 42 mitochondria of EB neurons were labeled with MitoTracker® Red (Molecular Probes, M-22425) at 250 nM concentration for 45 minutes at 37° C. Cells were then washed with fresh neural differentiation media and immediately imaged using the IncuCyte® Zoom live imaging system. Phase contrast as well as red fluorescence images were acquired every 3 hours for 4 days, starting 2 hours before the valinomycin treatment.

Mitophagy Assay.

ATP3-Rosella plasmid was acquired from and previously characterized by Rosado et al., 2008, ("Rosella: A fluorescent pH-biosensor for reporting vacuolar turnover of cytosol and organelles in yeast." *Autophagy* 4, 205-213). The ATP3-Rosella sequence was inserted into a lentivirus backbone with a CMV promotor. HEK 293T cells were transfected with 0.4 µg of the lenti-Rosella plasmid DNA using polyethylenimine (PEI). 48 hours post transfection cells were treated with 1 µM rotenone and 20 nM rapamycin and imaged every 3 hours for 3 days using the IncuCyte® Zoom live imaging system. Phase contrast, green fluorescence, and red fluorescence images were acquired.

Neurons differentiated using the EB protocol were infected with the lentivirus expressing the rosella bioprobe at MOI 10 on DIV 36. Valinomycin (2 µM) and Rotenone (1 µM) toxicities were applied to neurons on DIV 42, after which cells were imaged every 3 hours for 3 days using the IncuCyte® Zoom live imaging system. Phase contrast, green fluorescence, and red fluorescence images were acquired. The ratio of green/red fluorescence intensity was quantified.

Fibroblasts from healthy subject and Parkinson disease patients were infected with lentivirus expressing the rosella bioprobe at MOI 75 4h post-plating into 12 well plates with 60,000 cells per well. Two days later, cells were replated into 96 well plates with 2,000 cells per well. On the following day, DIV4, fibroblasts were transfected with ASOs targeting exon 41 (SEQ ID NO:02), exon 31 (SEQ ID NO:01), exon 2 (SEQ ID NO:07), and control non-target ASO (SEQ ID NO:05). Two days later, live cell imaging of the mitophagic flux was performed using the IncuCyte® Zoom live imaging system. Phase contrast, green fluorescence, and red fluorescence images were acquired. The ratio of green/red fluorescence intensity was quantified.

Endoplasmic Reticulum Stress Response.

Figure 13A:
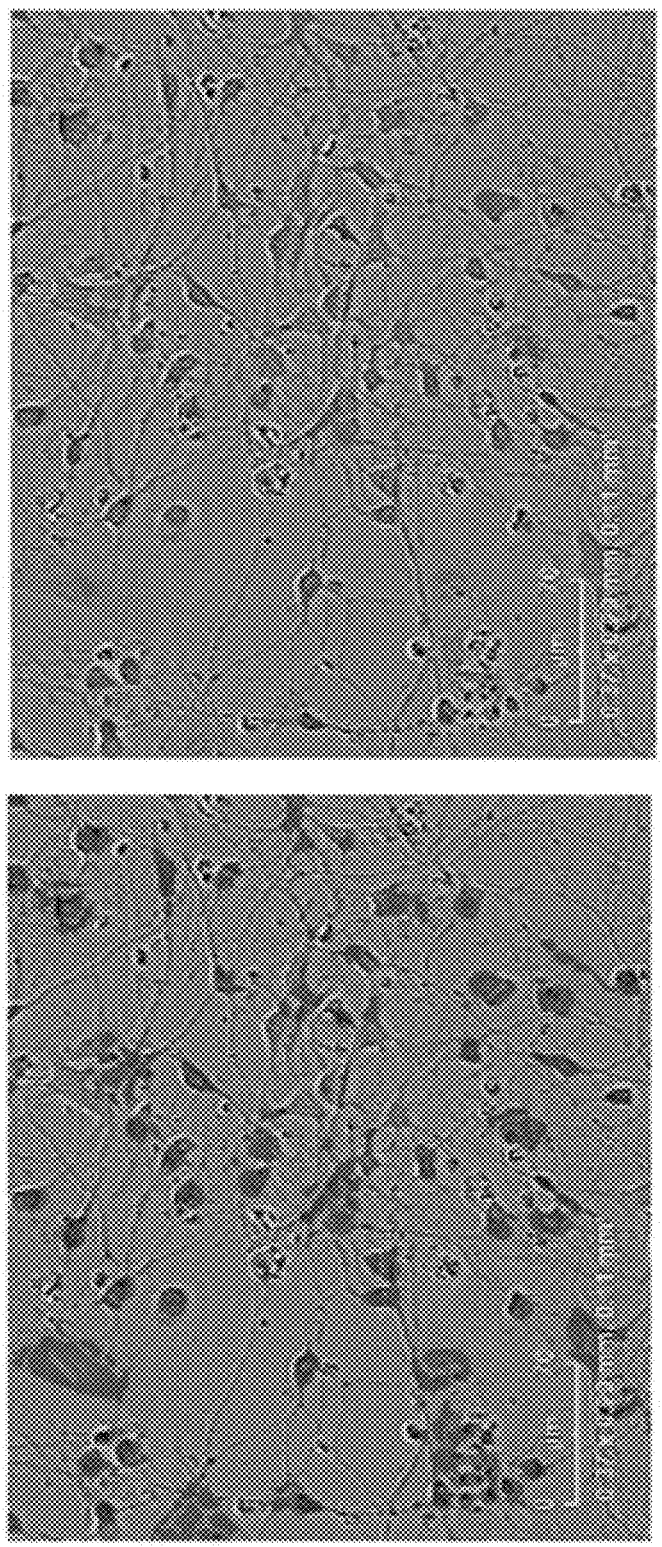
FIG. 13A shows the intracellular MitoTracker® distribution in iPS LRRK2 G2019S neuron cells.
Figure 13D:
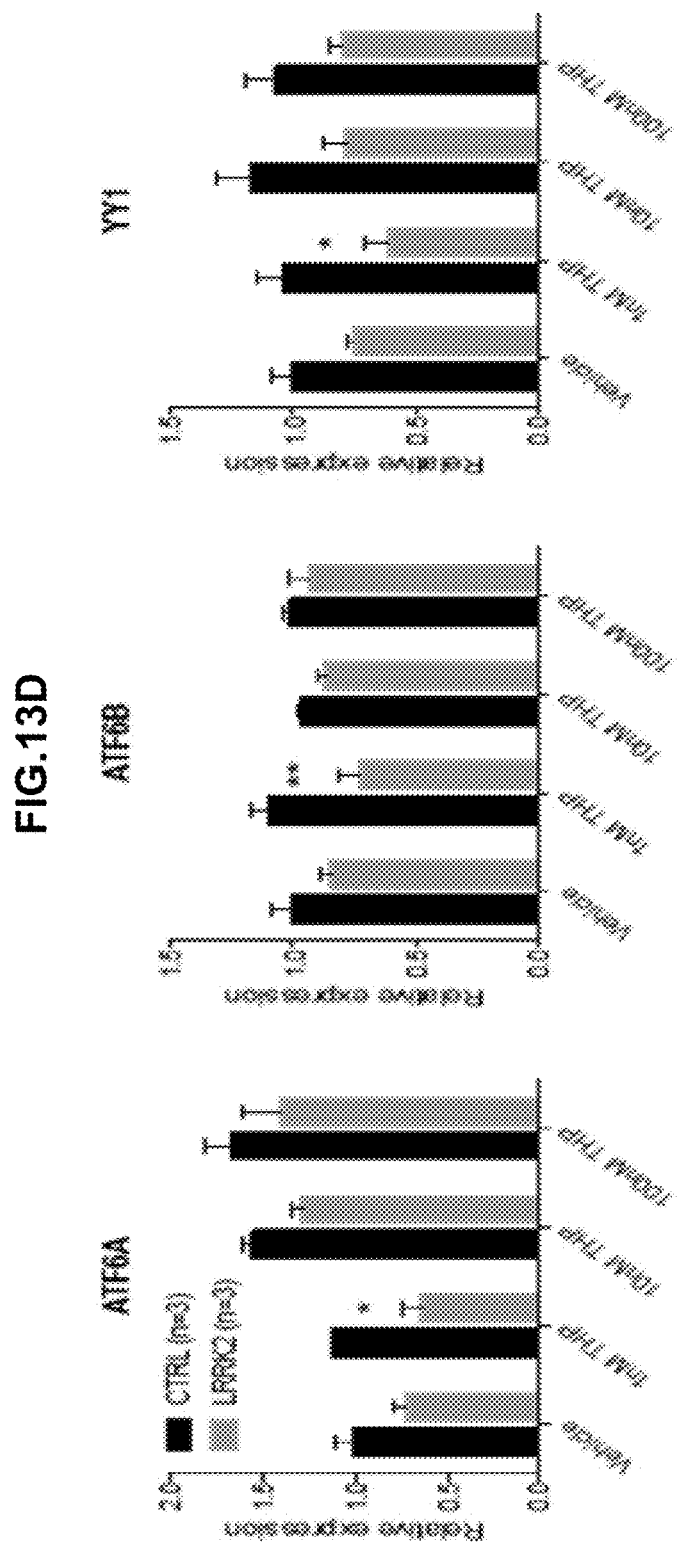
FIG. 13D shows gene expression levels of UPR activators. 2-way ANOVA indicates genotype significance for all comparisons. Results demonstrate that the ER stress response has lower activation threshold in LRRK2 G2019S human neurons compared to healthy subject neurons after calcium store depletion induced by thapsigargin (THP).
Figure 14A:
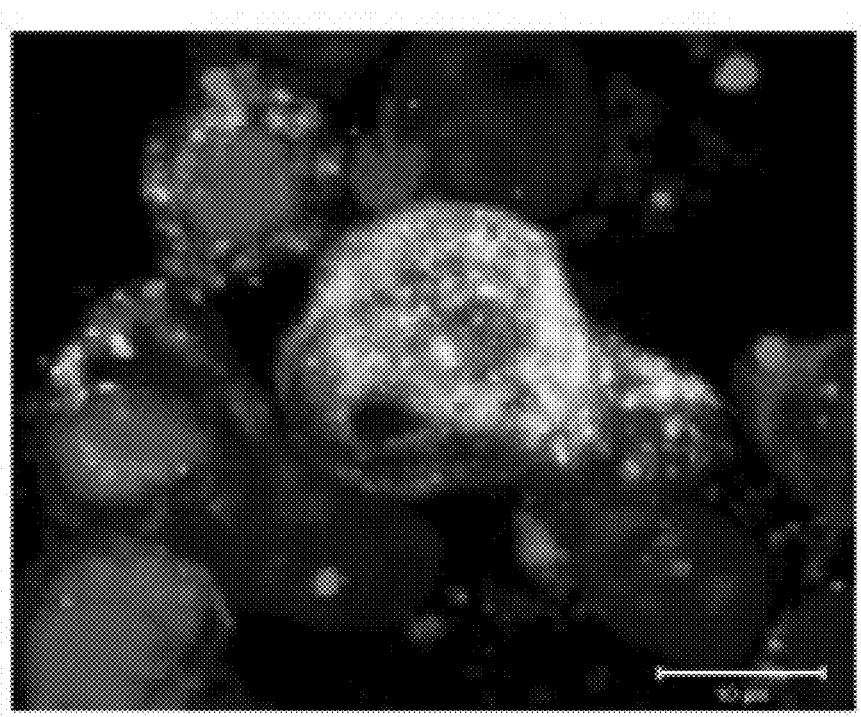
FIG. 14A shows an image of Mitophagy Rosella bioprobe intracellular localization in the 293T Hek cells transfected with the LV-CMV-ATP3 Rosella bioprobe. In addition to the red and green expression of the Rosella bioprobe, cells were co-stained with Tom20 for mitochondrial detection (Purple) and Hoechst (Blue) for nuclear identification.
Figure 14B:
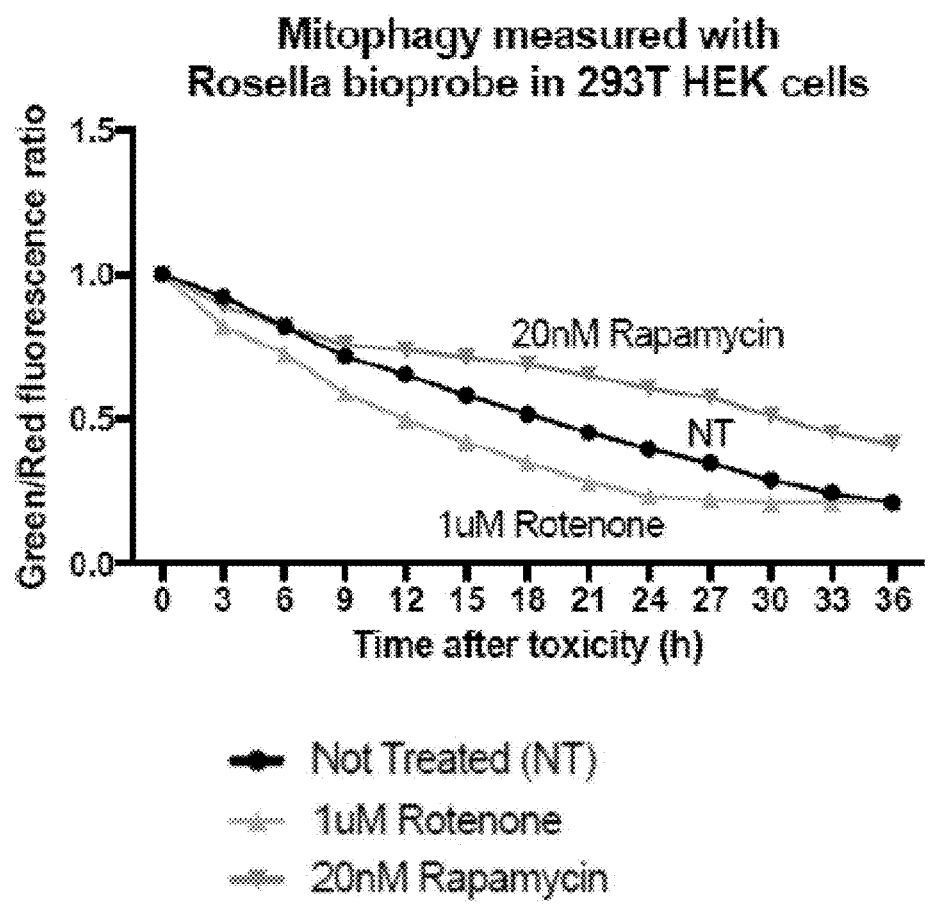
FIG. 14B shows mitophagy measured with live cell imaging of the Rosella bioprobe in 293T HEK cells. Results demonstrate that the Rosella bioprobe can successfully indicate mitophagy in 293T cells, shown by lower levels of the Green/Red fluorescent ratio, after 1 μM rotenone treatment of cells.
Figure 16:
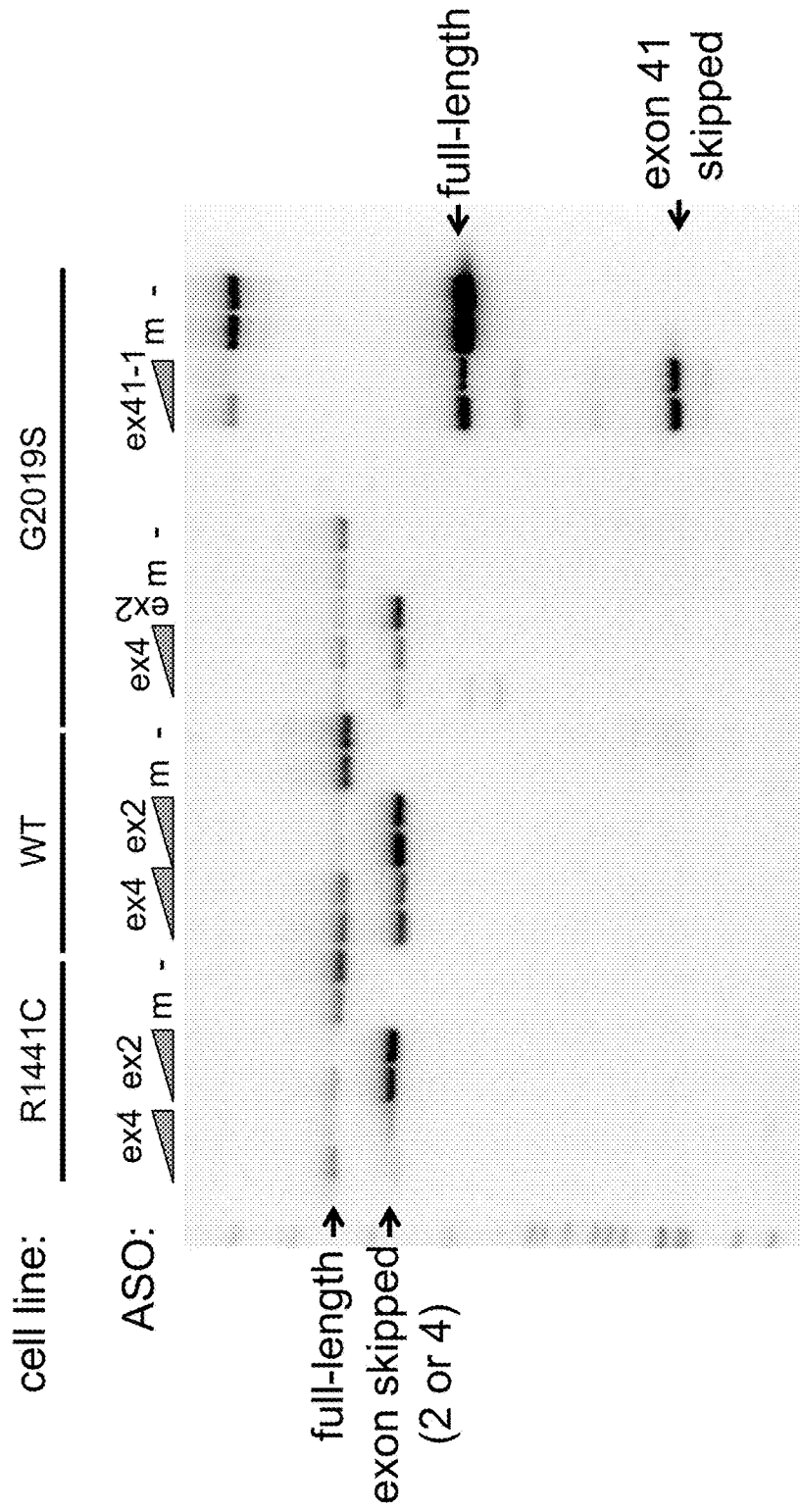
FIG. 16 demonstrates that antisense oligonucleotides (ASOs: ex4, exon 4 ASO, ATACACATATTACCTGAAGT-TAGGA (SEQ ID NO:06); ex2, exon 2 ASO, AGT-GAAAACAATGCCTTTACCTGCT (SEQ ID NO:07); and ex41-1, exon 41 ASO, AGACAGACCTGATCACCTAC-CTGGT (SEQ ID NO:02)) successfully induces skipping of LRRK2 exon 2, exon 4, and exon 41 containing either the R1441C mutation or the G2019S mutation in fibroblast cell lines derived from human patients carrying either the LRRK2 R1441C mutation or the LRRK2 G2019S mutation.
Figure 17A:
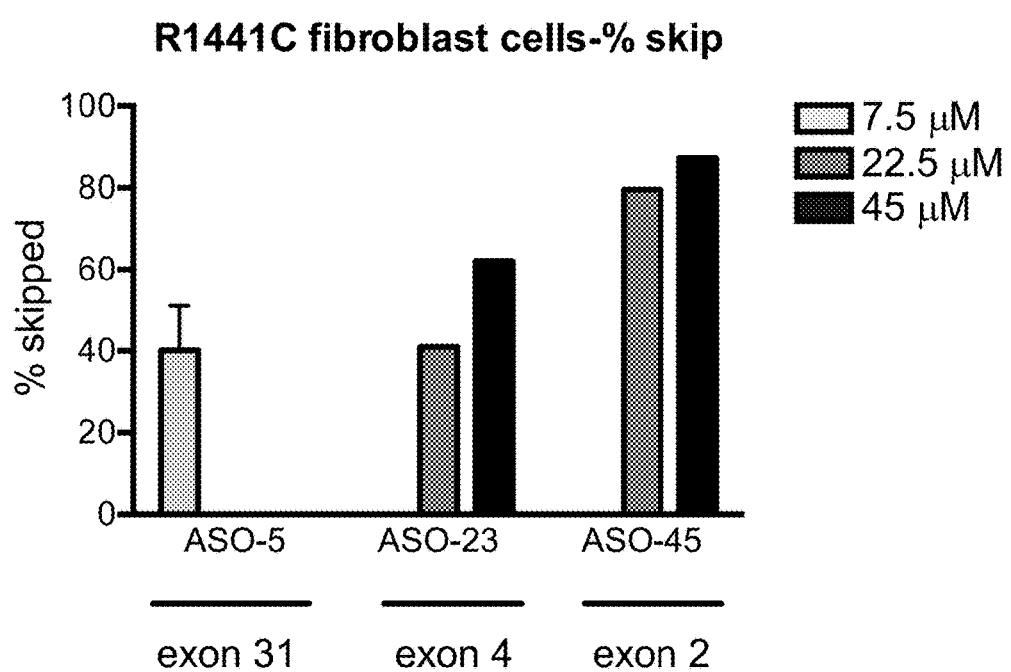
FIG. 17A shows quantification of the percentage of exon 31, exon 4, and exon 2 skipped when compared to the amount of the full length LRRK2 RNA product per treatment condition. Fibroblast cells isolated from a patient having a LRRK2 R1441C mutation were treated with 7.5 μM, 22.5 μM or 45 μM of each ASO. ASO-5 (CTACCA-GCCTACCATGTTACCTTGA; SEQ ID NO:01, targeting exon 31), ASO-23 (ATACACATATTACCTGAAGTTAG-GA; SEQ ID NO:06, targeting exon 4), and ASO-45 (AGT-GAAAACAATGCCTTTACCTGCT; SEQ ID NO:07, targeting exon 2).
Figure 17B:
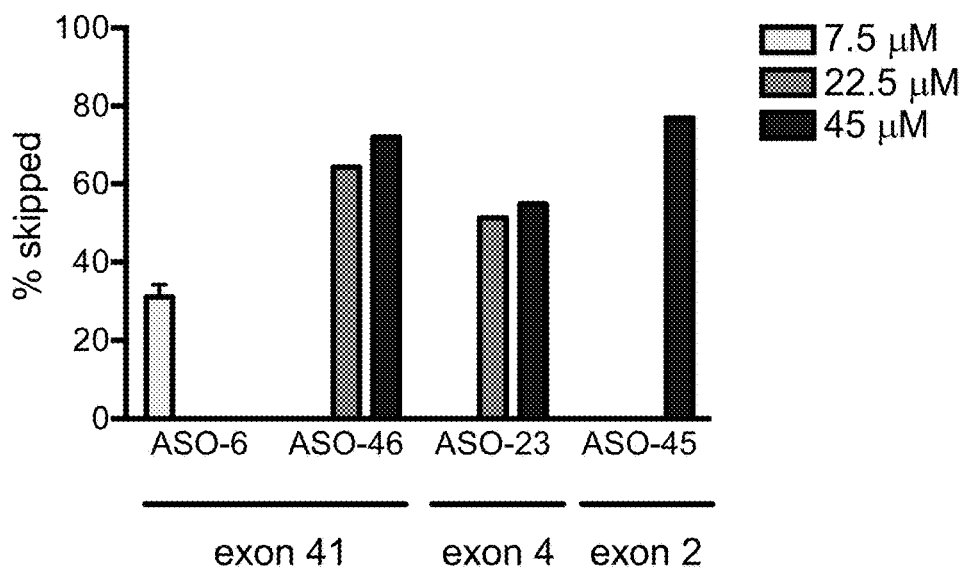
FIG. 17B shows quantification of the percentage of exon 41, exon 4, and exon 2 skipped when compared to the amount of the full length LRRK2 RNA product per treatment condition. Fibroblast cells isolated from a patient having a LRRK2 G2019S mutation were treated with 7.5 μM, 22.5 μM or 45 μM of each ASO. ASO-6 (AGACA-GACCTGATCACCTACCTGGT; SEQ ID NO:02, targeting exon 41), ASO-46 (GGTATCTGCCAGAAAATGCACA-GGA; SEQ ID NO:08, targeting exon 41), ASO-23 (ATA-CACATATTACCTGAAGTTAGGA; SEQ ID NO:06, targeting exon 4), and ASO-45 (AGTGAAAACAATGC-CTTTACCTGCT; SEQ ID NO:07, targeting exon 2).
Figure 19:
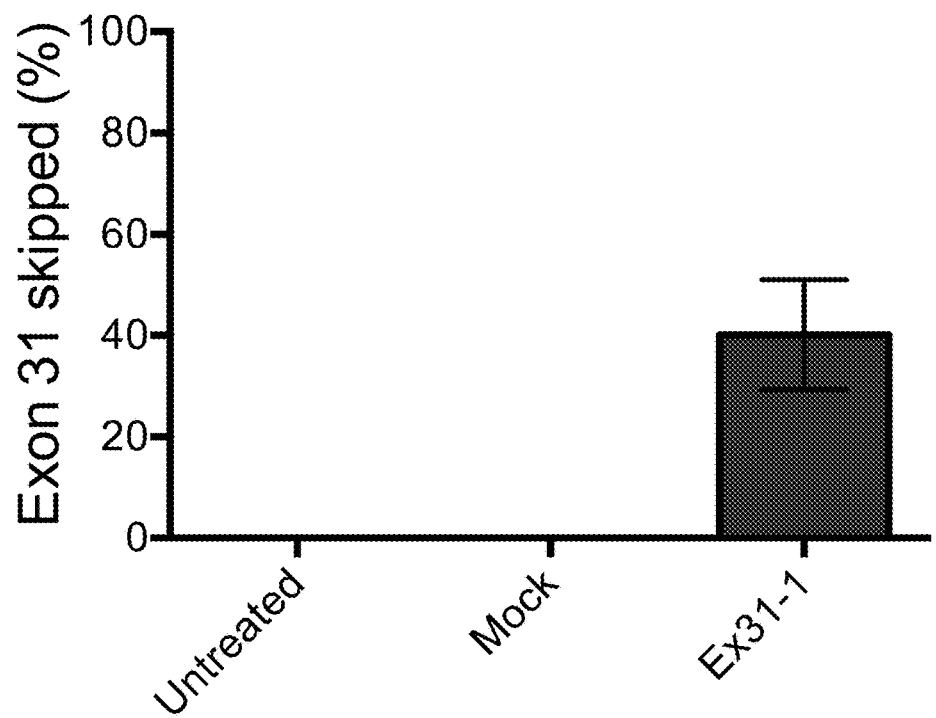
FIG. 19 shows that an ASO directed to exon 31 induces exon skipping in fibroblast cells isolated from a patient having a LRRK2 R1441C mutation. Cells were treated with 22.5 μM of ASO-31-1 (CTACCAGCCTACCATGTTACCT-TGA; SEQ ID NO:01).
Figure 20A:
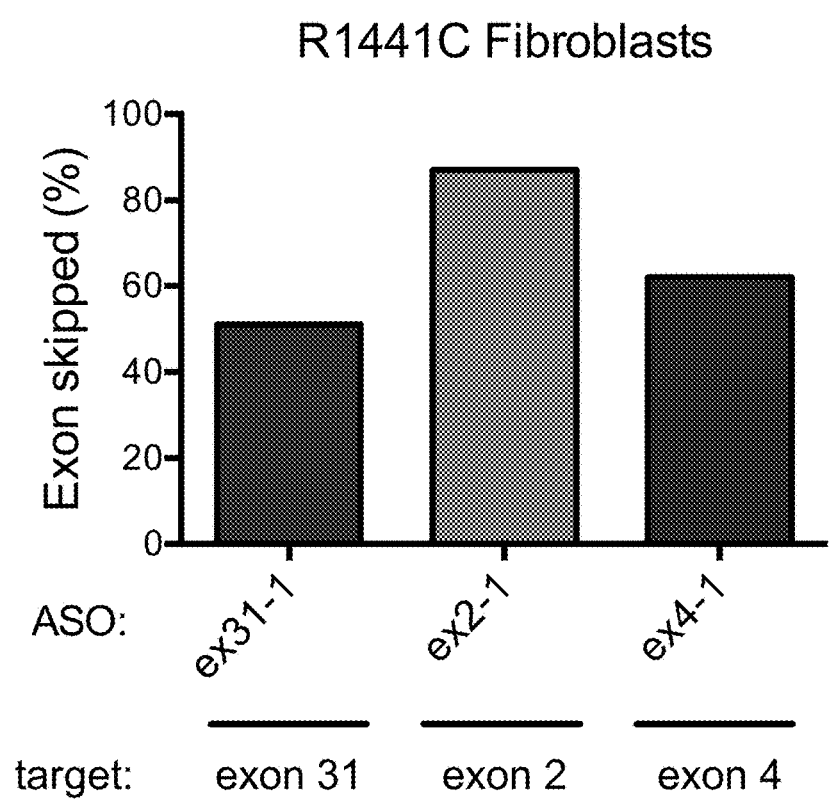
FIG. 20A shows quantification of the percentage of exon 31, exon 4, and exon 2 skipped when compared to the amount of the full length LRRK2 RNA product per treatment condition. Fibroblast cells isolated from a patient having a LRRK2 R1441C mutation were treated with 45 μM of each ASO: ASO-31-1 (CTACCAGCCTACCATGTTAC-CTTGA; SEQ ID NO:01), ASO-4-1 (ATACACATATTAC-CTGAAGTTAGGA; SEQ ID NO:06), and ASO-2-1 (AGT-GAAAACAATGCCTTTACCTGCT; SEQ ID NO:07).
Figure 20B:
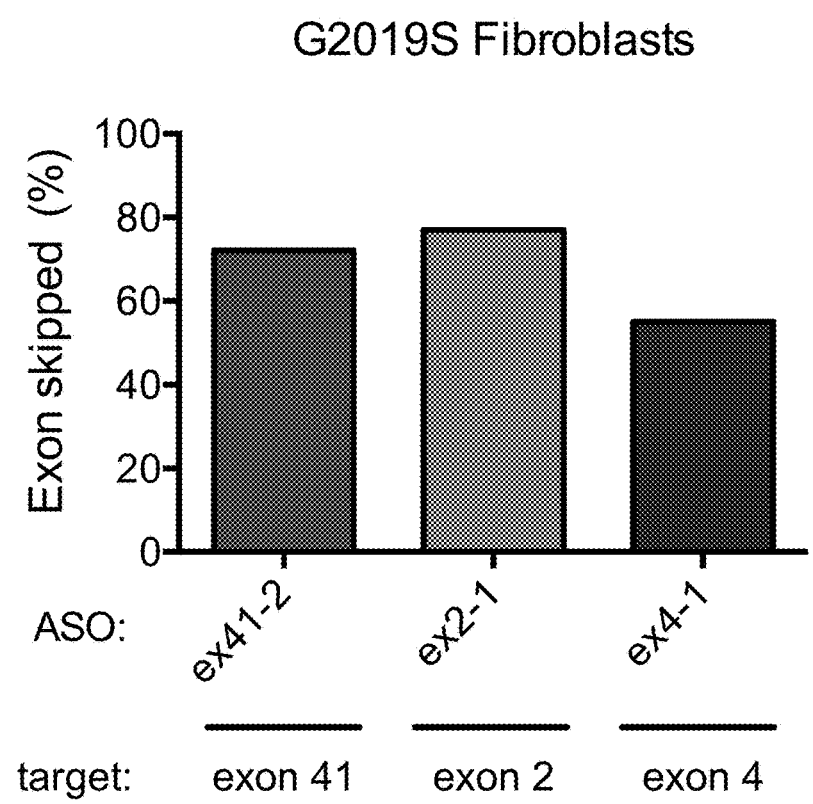
FIG. 20B shows quantification of the percentage of exon 41, exon 4, and exon 2 skipped when compared to the amount of the full length LRRK2 RNA product per treatment condition. Fibroblast cells isolated from a patient having a LRRK2 G2019S mutation were treated with 45 μM of each ASO: ASO-41-2 (GGTATCTGCCAGAAAATG-CACAGGA; SEQ ID NO:08), ASO-4-1 (ATACACATAT-TACCTGAAGTTAGGA; SEQ ID NO:06), and ASO-2-1 (AGTGAAAACAATGCCTTTACCTGCT; SEQ ID NO: 07).
Figure 22A:
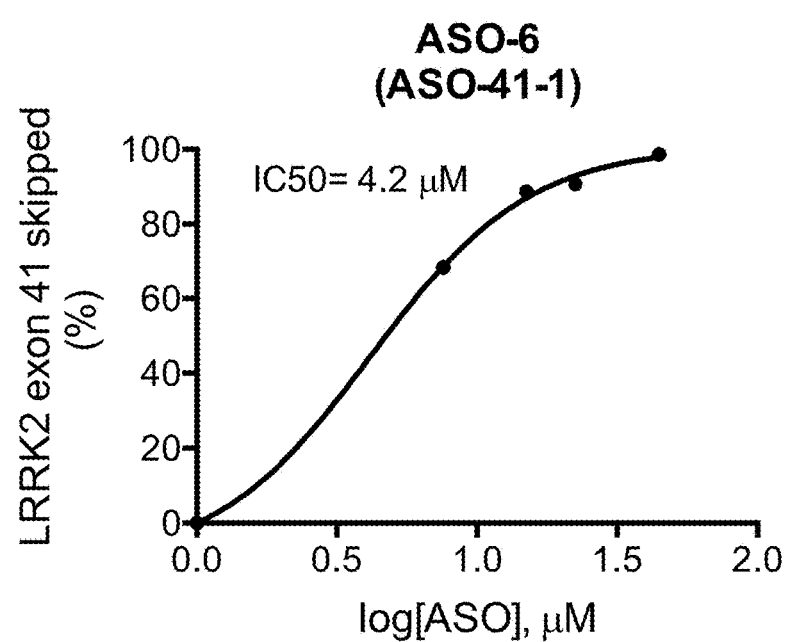
FIG. 22A shows a concentration curve for an ASO specific to exon 41. ASO-6 (AGACAGACCTGATCACCTACCTGGT; SEQ ID NO:02).
Figure 22B:
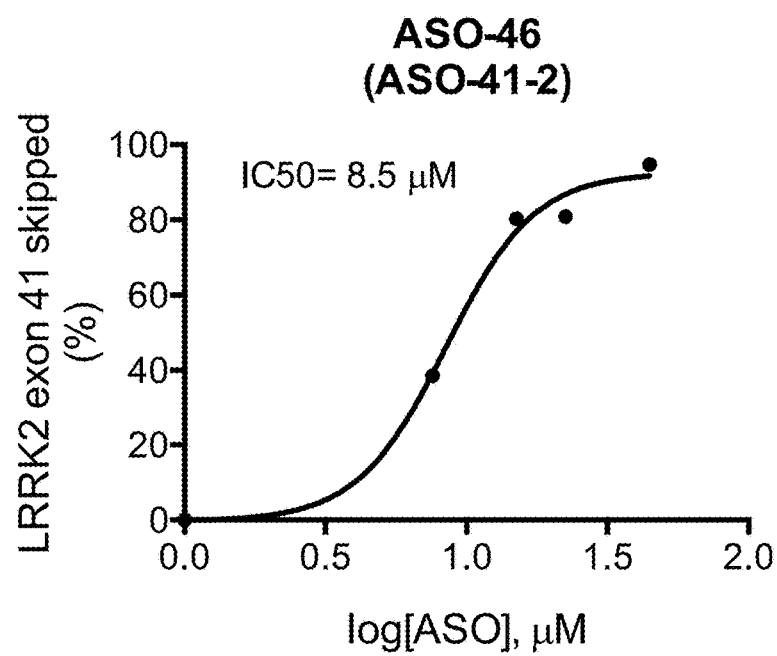
FIG. 22B shows a concentration curve for an ASO specific to exon 41. ASO-46 (GGTATCTGCCAGAAAATGCACAGGA; SEQ ID NO:08).
Figure 23A:
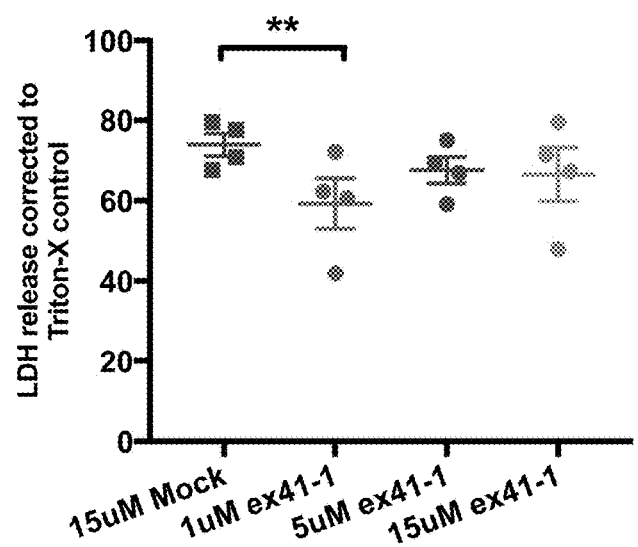
FIG. 23A shows that an ASO (ASO 41-1) targeting exon 41 (at 1 µM dose) in PD patient fibroblasts having the LRRK2 G2019S mutation decreases fibroblast cellular vulnerability to mitochondrial stress induced by membrane depolarization (valinomycin toxicity). One way repeated ANOVA with Dunnett's multiple testing correction; *p<0.05.
Figure 23B:
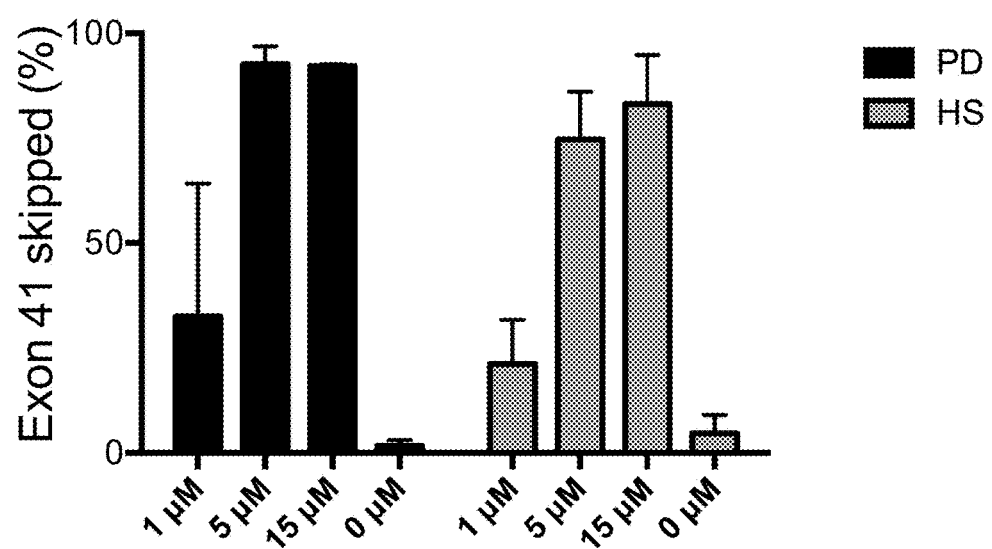
FIG. 23B shows quantification of the percentage of LRRK2 exon 41 skipped by ASO-41-1 in cells from healthy subjects (HS cells) and cells from PD patients carrying the LRRK2 G2019S mutation (PD cells).
Figure 24:
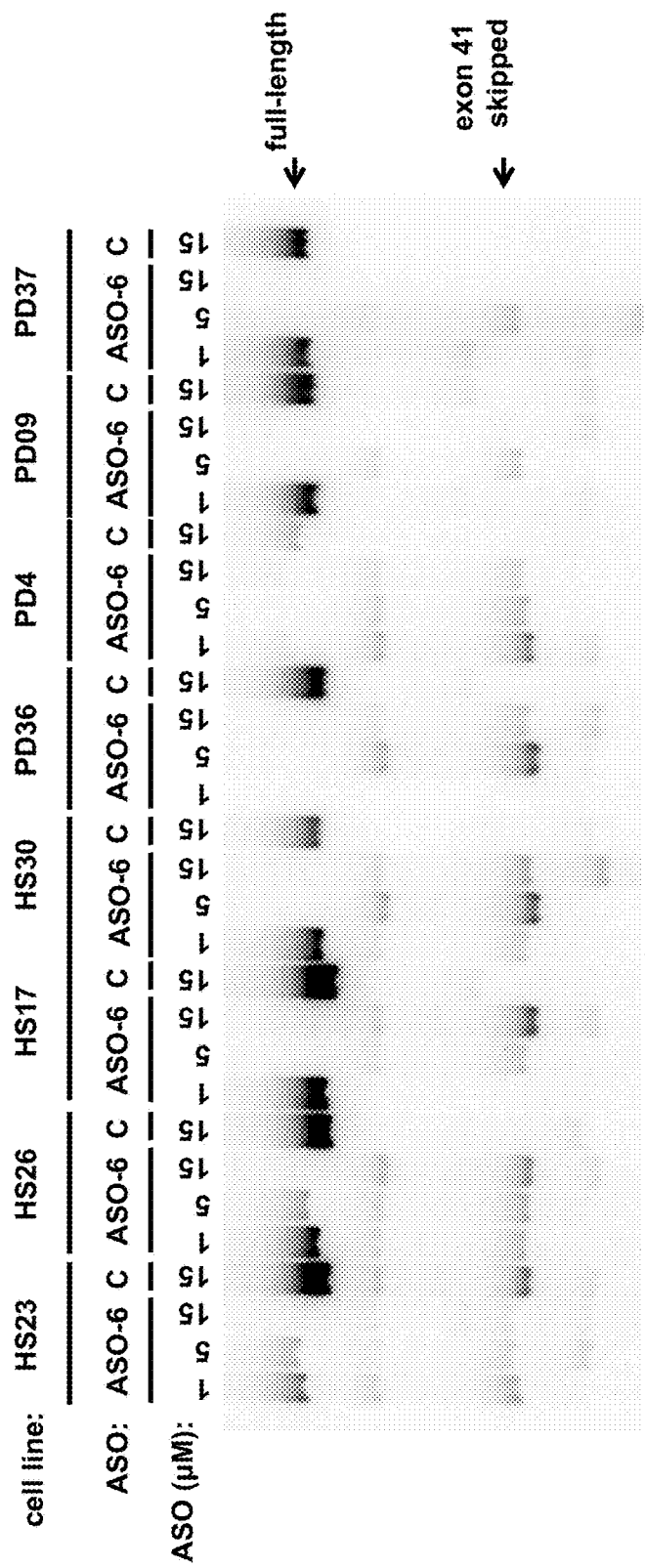
FIG. 24 shows that an ASO (ASO-6 (AGACAGACCTGATCACCTACCTGGT SEQ ID NO:02) directed to exon 41 induces dose responsive exon 41 skipping in various human fibroblast cell lines. Cells were treated with 1 µM, 5 µM, or 15 µM of ASO-6. HS23 cells are healthy subject cells from donor 23; HS26 cells are healthy subject cells from donor 26; HS17 cells are healthy subject cells from donor 17; HS30 cells are healthy subject cells from donor 30; PD36 cells are Parkinson disease patient cells from donor 36 carrying the LRRK2 G2019S mutation; PD4 cells are Parkinson disease patient cells from donor 4 carrying the LRRK2 G2019S mutation; PD09 cells are Parkinson disease patient cells from donor 09 carrying the LRRK2 G2019S mutation; PD37 cells are Parkinson disease patient cells from donor 37 carrying the LRRK2 G2019S mutation.
Figure 25:
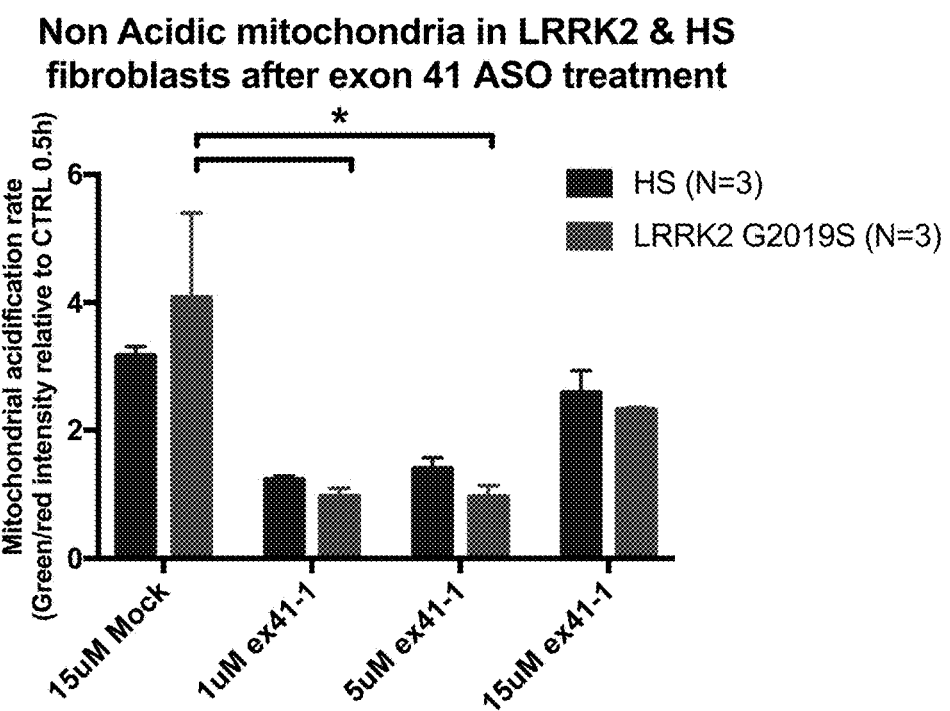
FIG. 25 shows that LRRK2 exon 41 skipping increases the number of lysed mitochondria in human fibroblasts. Fibroblast cell lines isolated from patients carrying a LRRK2 G2019S mutation (LRRK2 G2019S) and healthy subject controls (HS) cells were treated with 1 µM, 5 µM, or 15 µM of ASO-41-1.
Figure 26A:
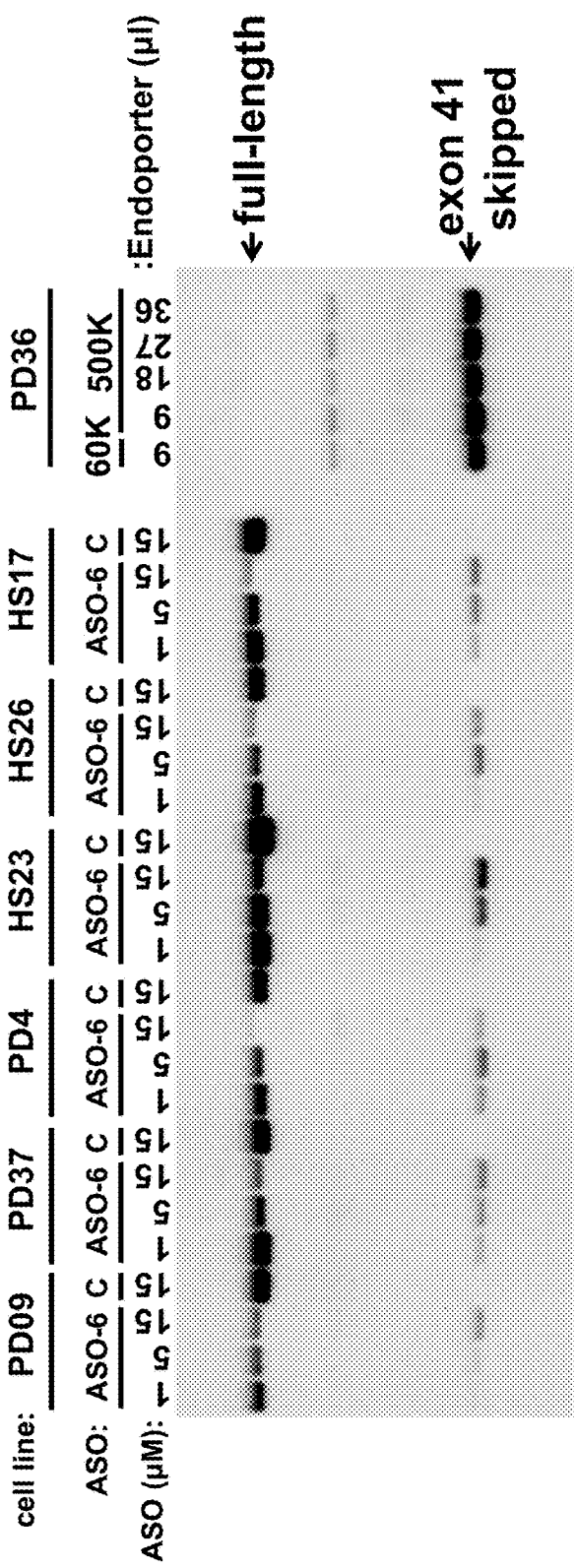
FIG. 26A shows that an ASO (ASO-6) directed to exon 41 induces dose responsive exon 41 skipping in various cell lines. Cells were treated with 1 µM, 5 µM, or 15 µM of ASO-6. HS23 cells are healthy subject cells from donor 23; HS26 cells are healthy subject cells from donor 26; HS17 cells are healthy subject cells from donor 17; PD36 cells are Parkinson disease patient cells from donor 36 carrying the LRRK2 G2019S mutation; PD4 cells are Parkinson disease patient cells from donor 4 carrying the LRRK2 G2019S mutation; PD09 cells are Parkinson disease patient cells from donor 09 carrying the LRRK2 G2019S mutation; PD37 cells are Parkinson disease patient cells from donor 37 carrying the LRRK2 G2019S mutation.
Figure 26B:
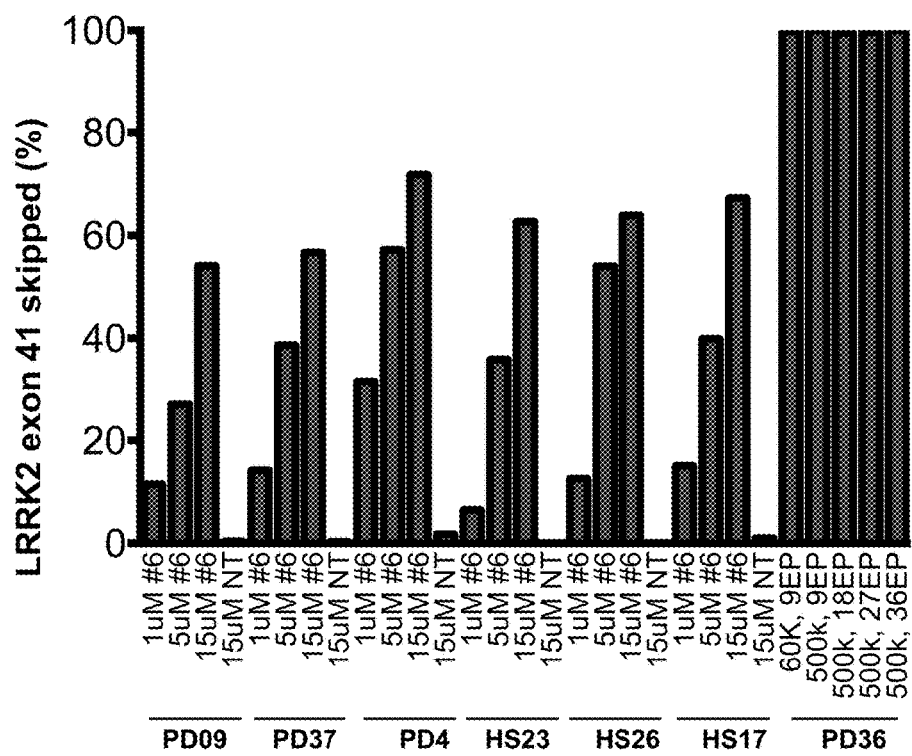
FIG. 26B shows quantification of the percentage of LRRK2 exon 41 skipped induced by ASO-6 in the HS cells and PD cells.
Figure 27A:
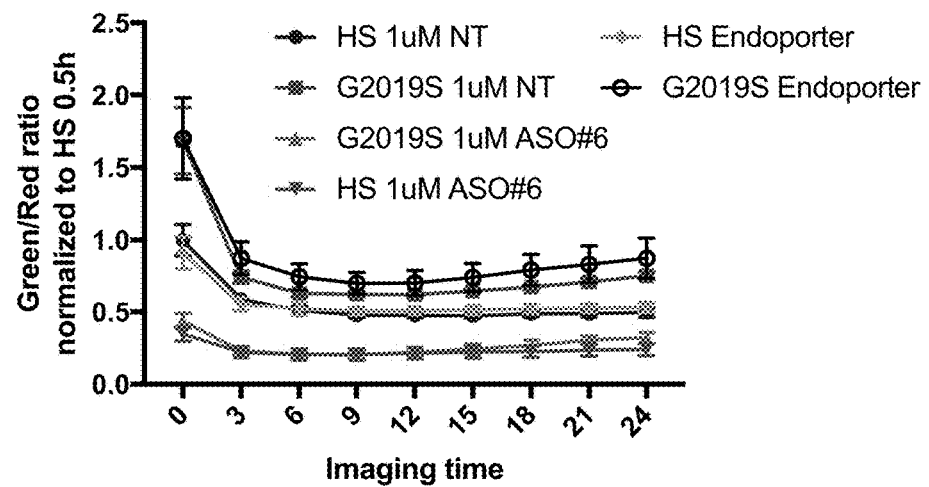
FIG. 27A shows mitochondrial acidification (an indication of rescue of mitophagic flux) in PD patient derived fibroblasts carrying the LRRK2 G2019S mutation upon exon 41 skipping induced by treatment with 1 µM of ASO#6.
Figure 27B:
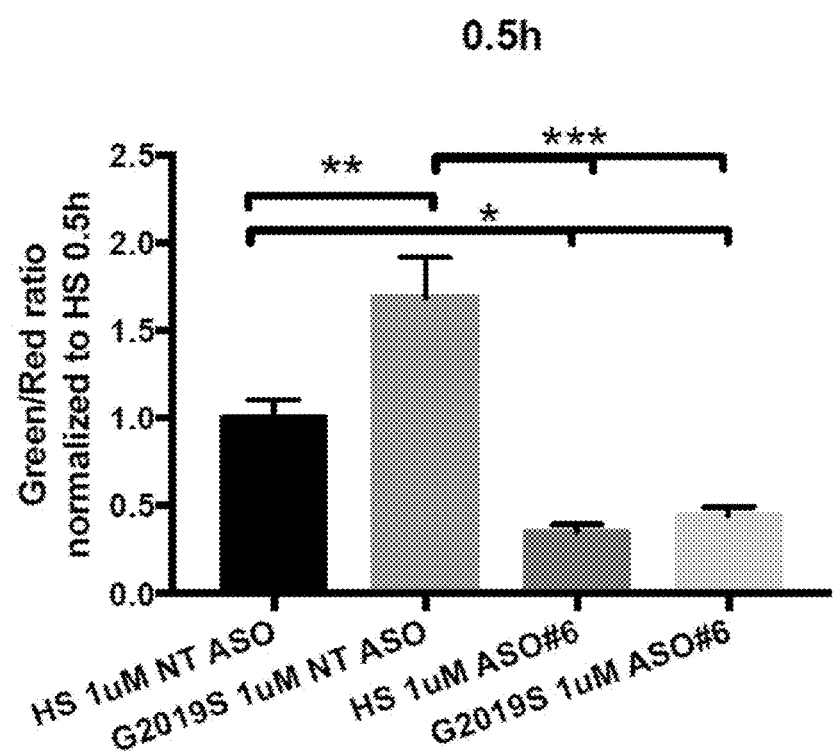
FIG. 27B shows mitochondrial acidification (an indication of rescue of mitophagic flux) in PD patient derived fibroblasts carrying the LRRK2 G2019S mutation upon exon 41 skipping induced by treatment with 1 µM of ASO#6 imaged at 0.5 hours. One way ANOVA with Tukey's multiple testing correction; *p<0.05, p<0.01, *p<0.001.
Figure 27C:
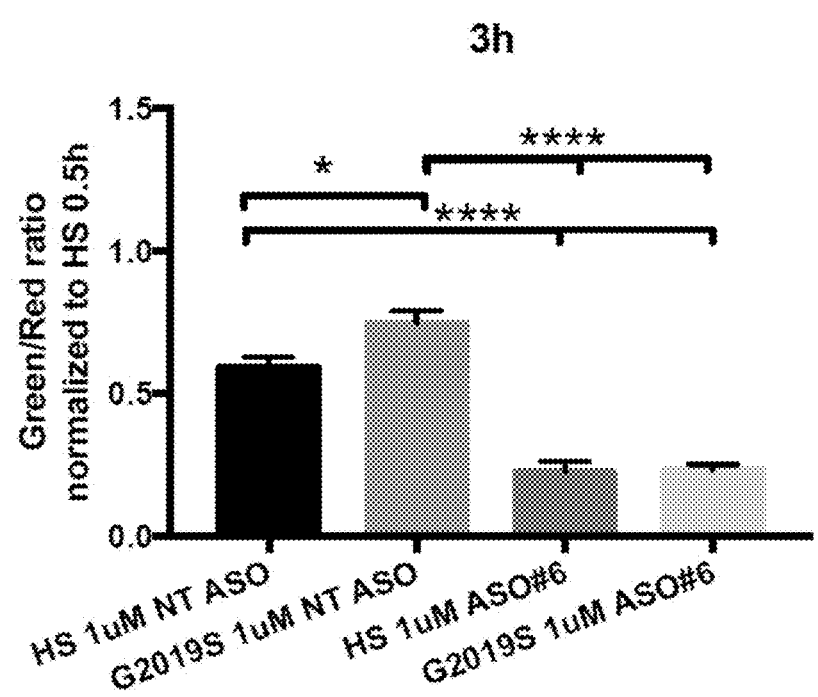
FIG. 27C shows mitochondrial acidification (an indication of rescue of mitophagic flux) in PD patient derived fibroblasts carrying the LRRK2 G2019S mutation upon exon 41 skipping induced by treatment with 1 µM of ASO#6 imaged at 3 hours. One way ANOVA with Tukey's multiple testing correction; *p<0.05, ****p<0.0001.
Figure 27D:
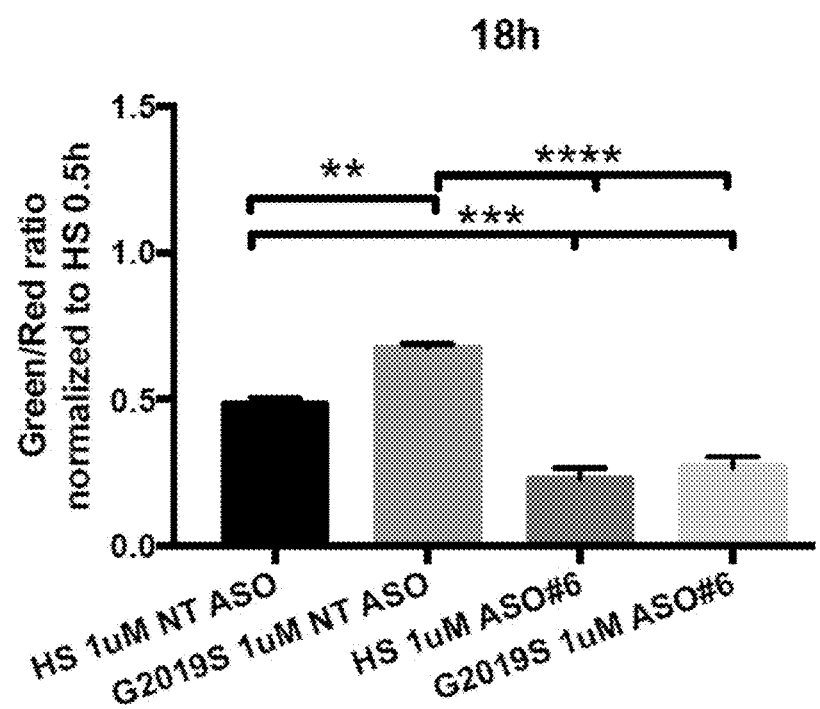
FIG. 27D shows mitochondrial acidification (an indication of rescue of mitophagic flux) in PD patient derived fibroblasts carrying the LRRK2 G2019S mutation upon exon 41 skipping induced by treatment with 1 µM of ASO#6 imaged at 18 hours. One way ANOVA with Tukey's multiple testing correction; p<0.01, *p<0.001, ****p<0.0001.
Figure 28A:
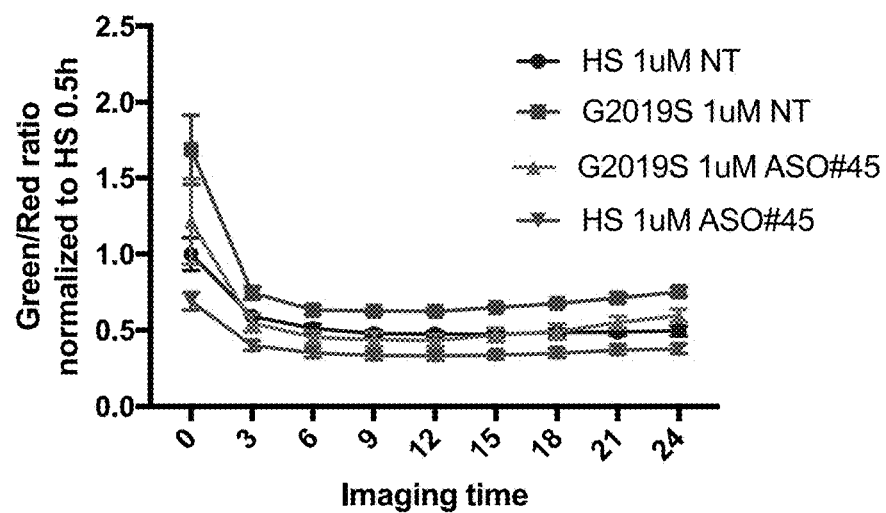
FIG. 28A shows mitochondrial acidification (an indication of rescue of mitophagic flux) in PD patient derived fibroblasts carrying the LRRK2 G2019S mutation upon exon 2 skipping induced by treatment with 1 µM of ASO#45.
Figure 28B:
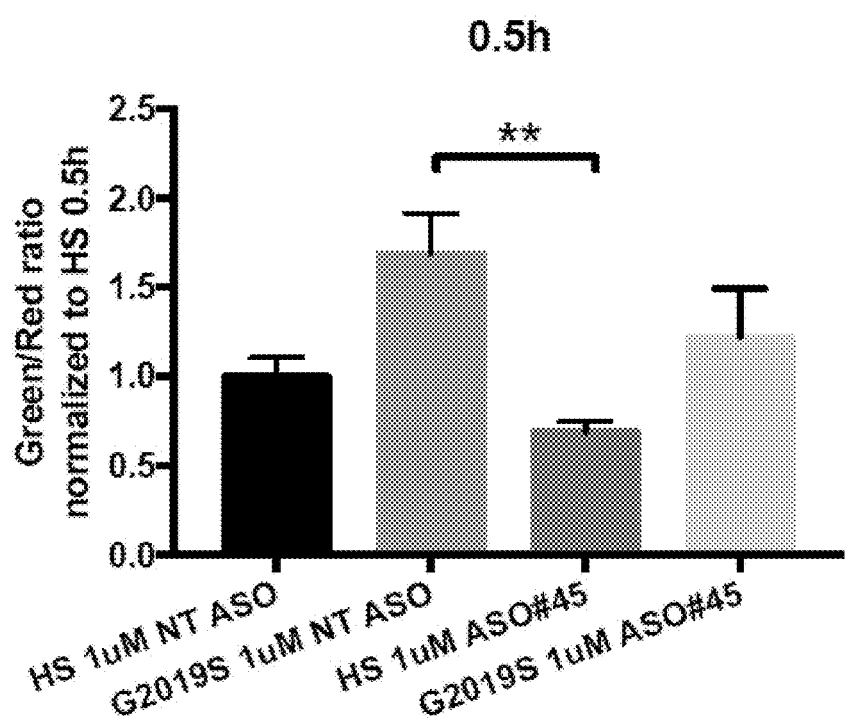
FIG. 28B shows mitochondrial acidification (an indication of rescue of mitophagic flux) in PD patient derived fibroblasts carrying the LRRK2 G2019S mutation upon exon 2 skipping induced by treatment with 1 µM of ASO#45 imaged at 0.5 hours. One way ANOVA with Tukey's multiple testing correction; **p<0.01.
Figure 28C:
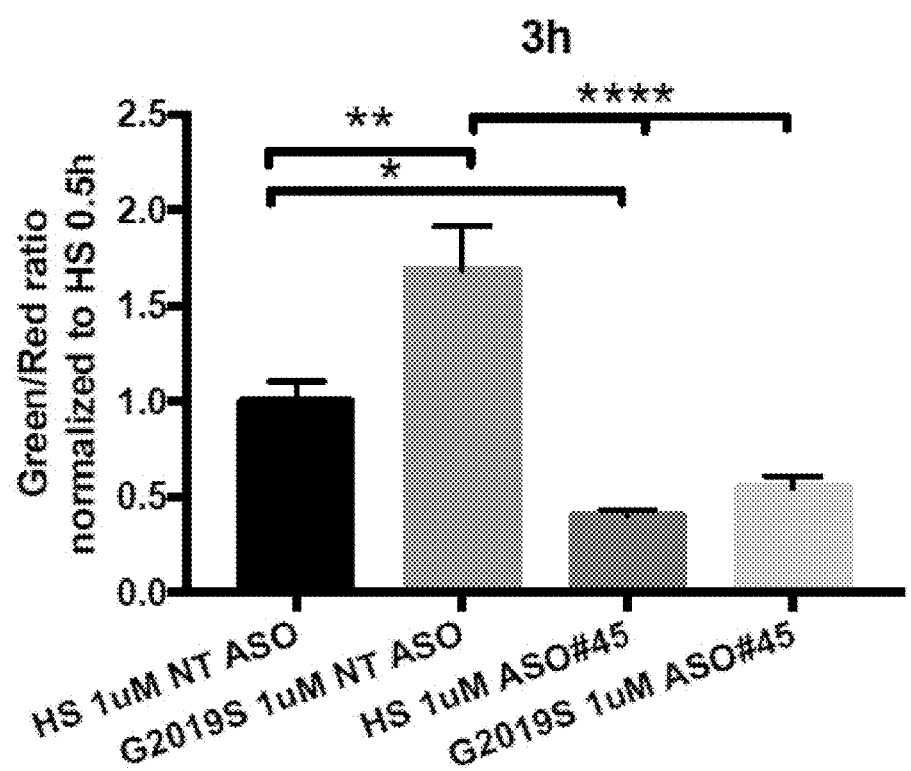
FIG. 28C shows mitochondrial acidification (an indication of rescue of mitophagic flux) in PD patient derived fibroblasts carrying the LRRK2 G2019S mutation upon exon 2 skipping induced by treatment with 1 µM of ASO#45 imaged at 3 hours. One way ANOVA with Tukey's multiple testing correction; *p<0.05, p<0.01, **p<0.0001.
Figure 28D:
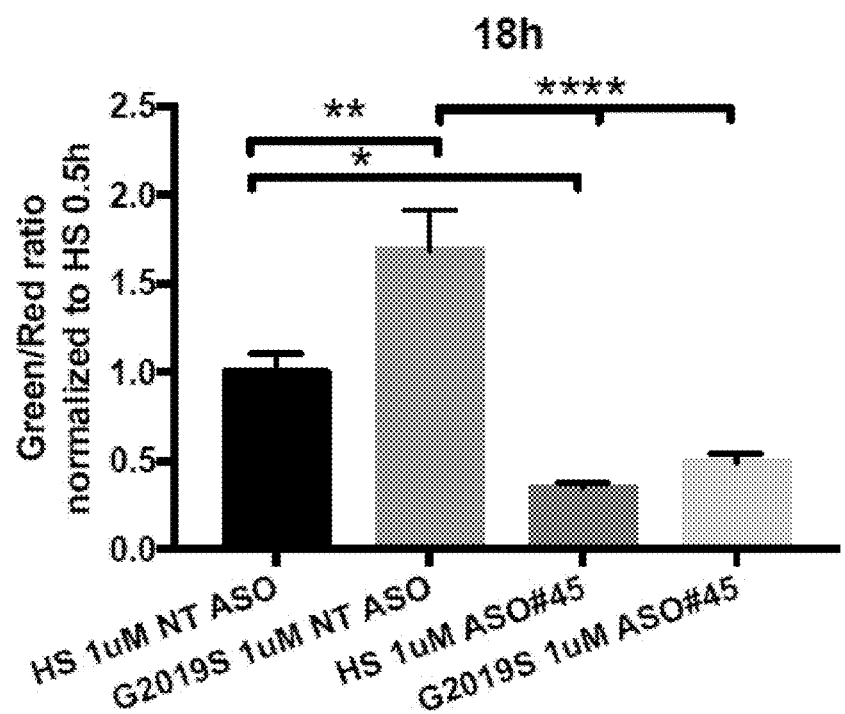
FIG. 28D shows mitochondrial acidification (an indication of rescue of mitophagic flux) in PD patient derived fibroblasts carrying the LRRK2 G2019S mutation upon exon 2 skipping induced by treatment with 1 µM of ASO#45 imaged at 18 hours. One way ANOVA with Tukey's multiple testing correction; *p<0.05, p<0.01, **p<0.0001.
Figure 29A:
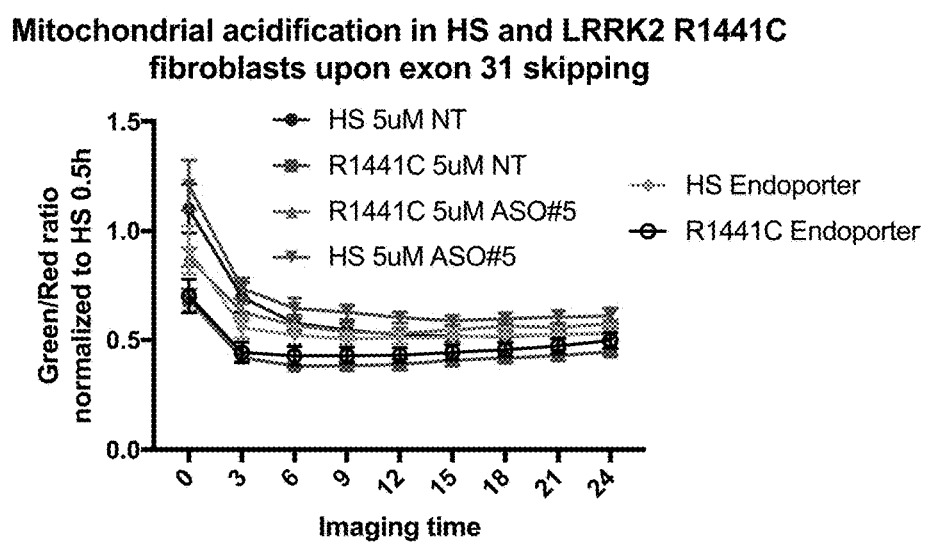
FIG. 29A shows mitochondrial acidification (an indication of rescue of mitophagic flux) in PD patient derived fibroblasts carrying the LRRK2 R1441C mutation upon exon 31 skipping induced by treatment with 5 µM of ASO#5.
Figure 29B:
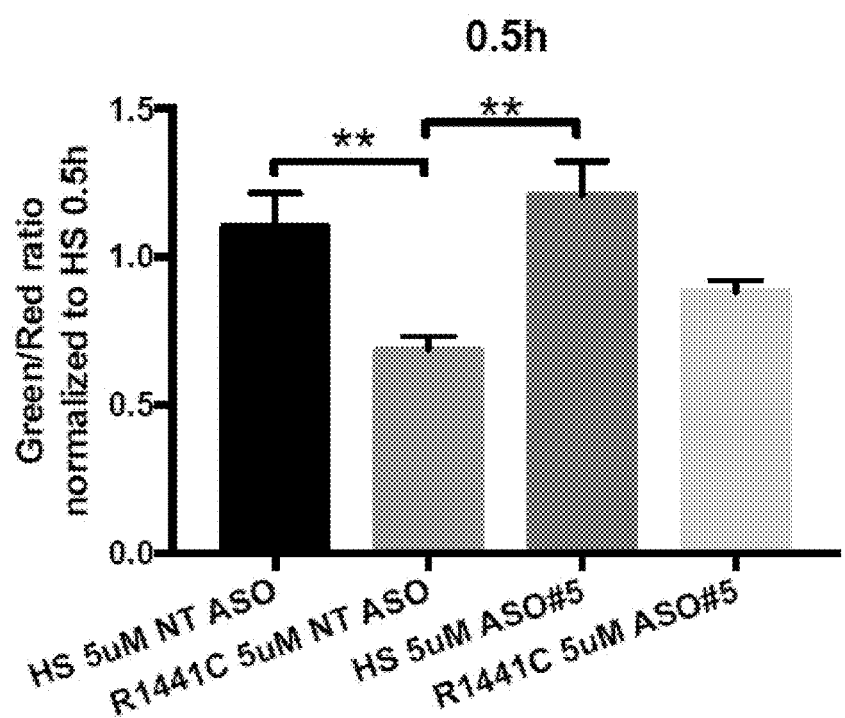
FIG. 29B shows mitochondrial acidification (an indication of rescue of mitophagic flux) in PD patient derived fibroblasts carrying the LRRK2 R1441C mutation upon exon 31 skipping induced by treatment with 5 µM of ASO#5 imaged at 0.5 hours. One way ANOVA with Tukey's multiple testing correction; **p<0.01.
Figure 29C:
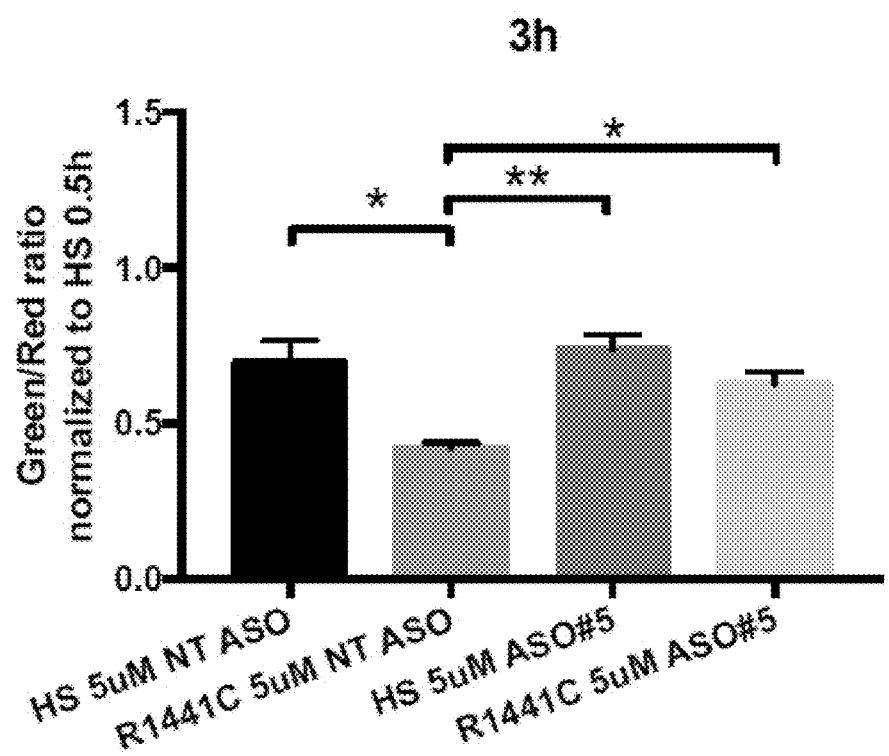
FIG. 29C shows mitochondrial acidification (an indication of rescue of mitophagic flux) in PD patient derived fibroblasts carrying the LRRK2 R1441C mutation upon exon 31 skipping induced by treatment with 5 µM of ASO#5 imaged at 3 hours. One way ANOVA with Tukey's multiple testing correction; *p<0.05, **p<0.01.
Figure 29D:
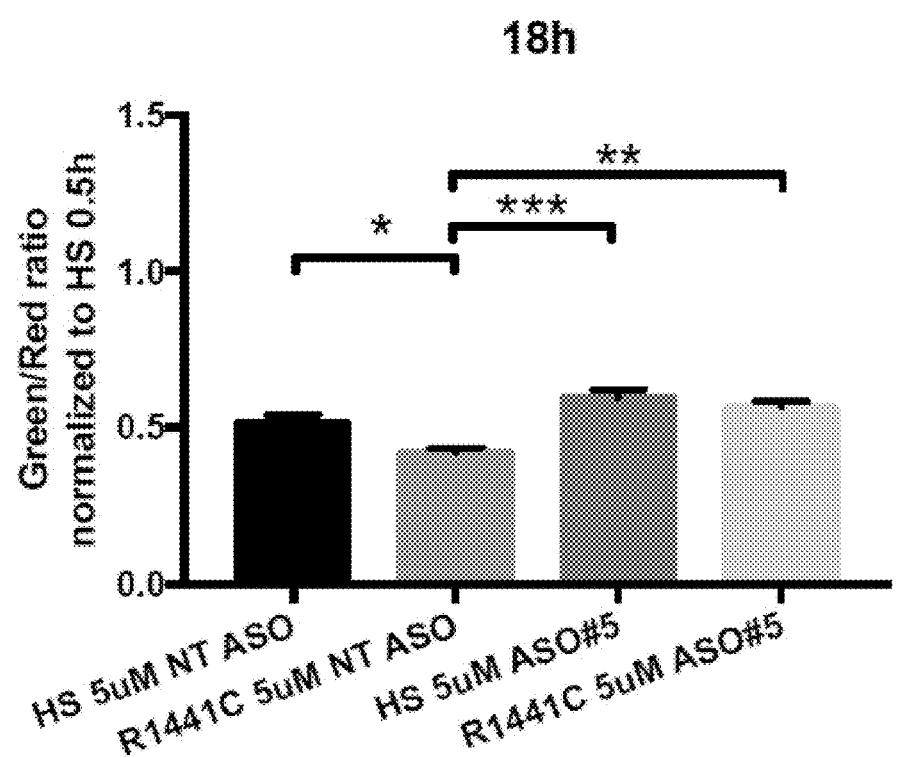
FIG. 29D shows mitochondrial acidification (an indication of rescue of mitophagic flux) in PD patient derived fibroblasts carrying the LRRK2 R1441C mutation upon exon 31 skipping induced by treatment with 5 µM of ASO#5 imaged at 18 hours. One way ANOVA with Tukey's multiple testing correction; *p<0.05, p<0.0, *p<0.001.
Figure 30A:
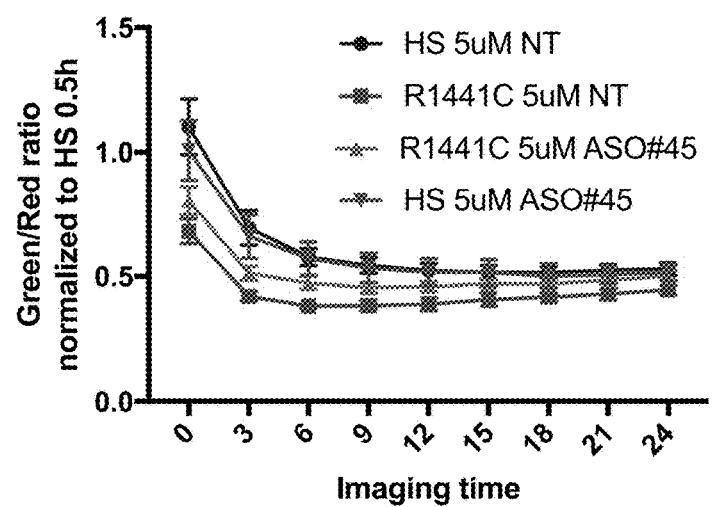
FIG. 30A shows mitochondrial acidification (an indication of rescue of mitophagic flux) in PD patient derived fibroblasts carrying the LRRK2 R1441C mutation upon exon 2 skipping induced by treatment with 5 µM of ASO#45.
Figure 30B:
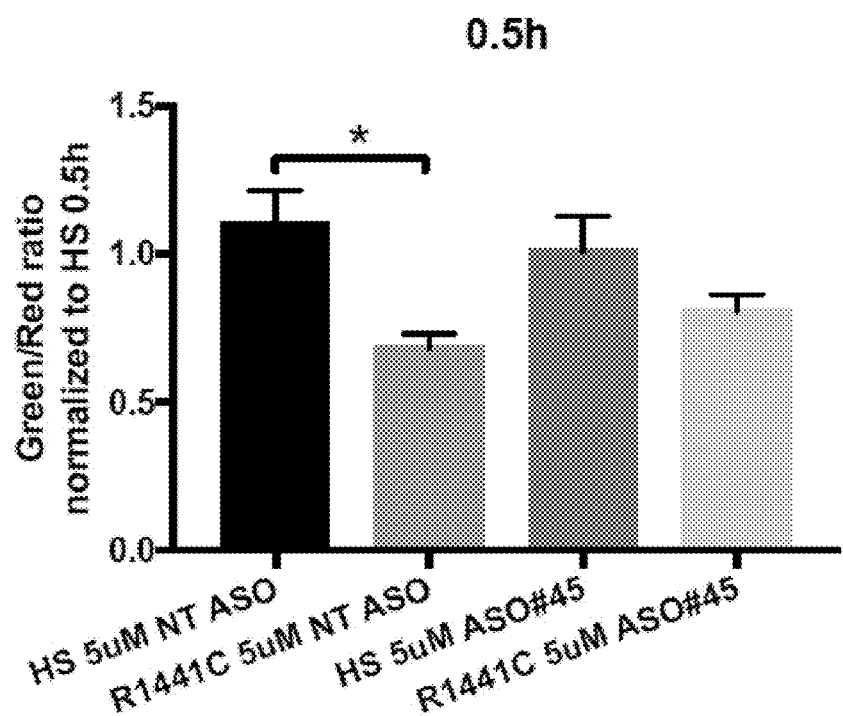
FIG. 30B shows mitochondrial acidification (an indication of rescue of mitophagic flux) in PD patient derived fibroblasts carrying the LRRK2 R1441C mutation upon exon 2 skipping induced by treatment with 5 µM of ASO#45 imaged at 0.5 hours. One way ANOVA with Tukey's multiple testing correction; *p<0.05.
Figure 30C:
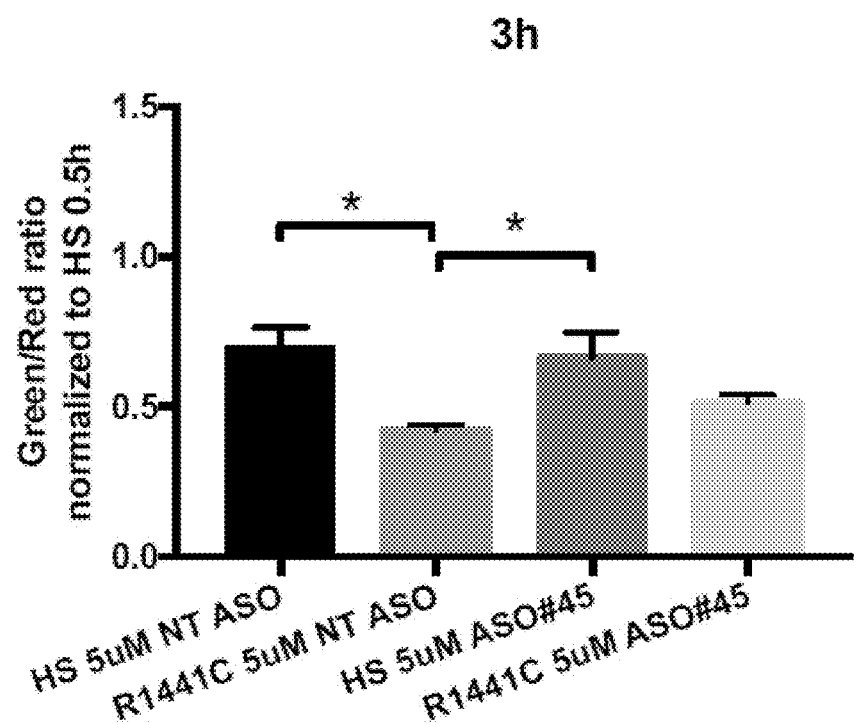
FIG. 30C shows mitochondrial acidification (an indication of rescue of mitophagic flux) in PD patient derived fibroblasts carrying the LRRK2 R1441C mutation upon exon 2 skipping induced by treatment with 5 μM of ASO#45 imaged at 3 hours. One way ANOVA with Tukey's multiple testing correction; *p<0.05.
Figure 31:
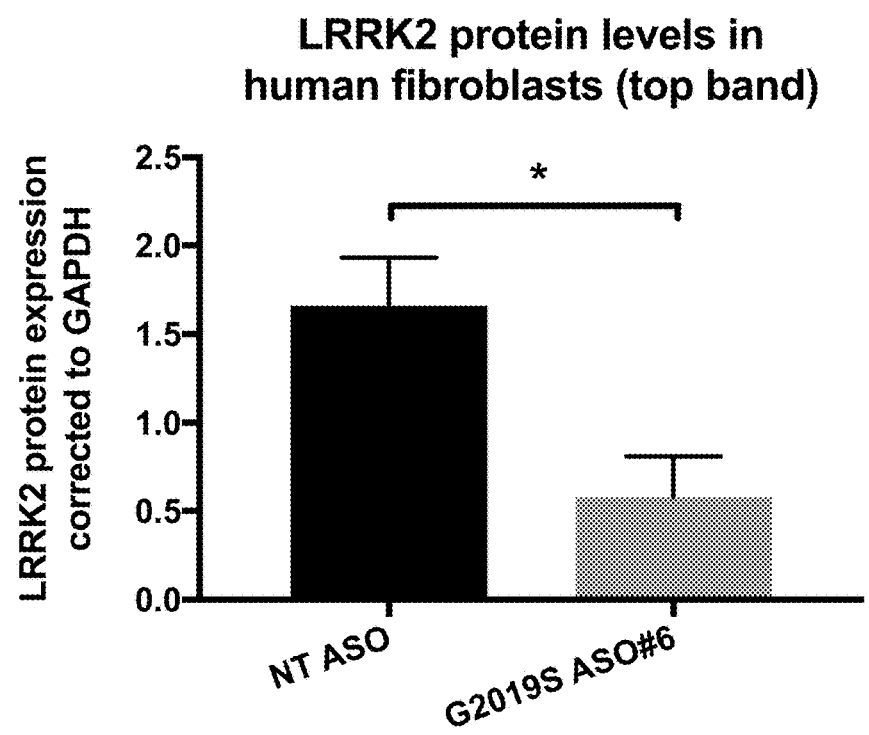
FIG. 31 shows a decrease in LRRK2 protein expression in PD patient derived fibroblasts carrying the LRRK2 G2019S mutation when treated with an ASO targeting exon 41. Treatment with 15 μM of ASO#6 results in a decrease in LRRK2 protein levels. Paired t-test, *p<0.05
Figure 32B:
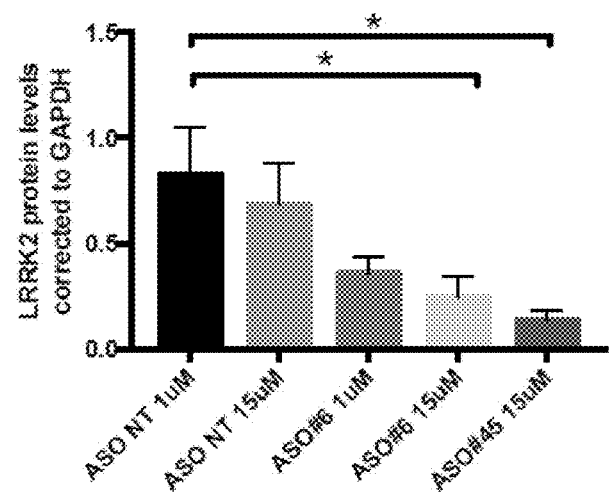
FIG. 32B shows a decrease in LRRK2 protein expression in HS fibroblasts and PD patient derived fibroblasts carrying the LRRK2 G2019S mutation when treated with ASOs targeting exon 41 or exon 2. Treatment with 1 μM or 15 μM of ASO#6, or 15 μM of ASO#45 results in a decrease in LRRK2 protein levels. One way ANOVA with Dunnett's multiple testing correction; *p<0.05.
Figure 34A:
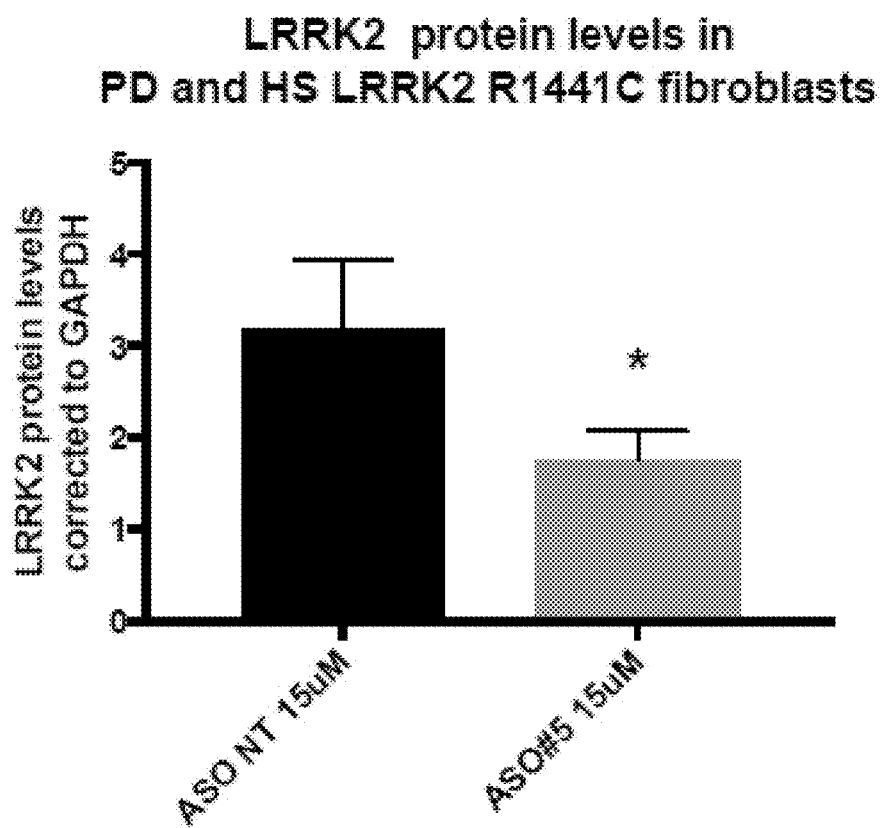
FIG. 34A shows a decrease in LRRK2 protein expression in HS fibroblasts and PD patient derived fibroblasts carrying the LRRK2 R1441C mutation when treated with an ASO targeting exon 31. Treatment with 15 μM of ASO#5 results in a decrease in LRRK2 protein levels. Paired t-test, *p<0.05.
Figure 34B:
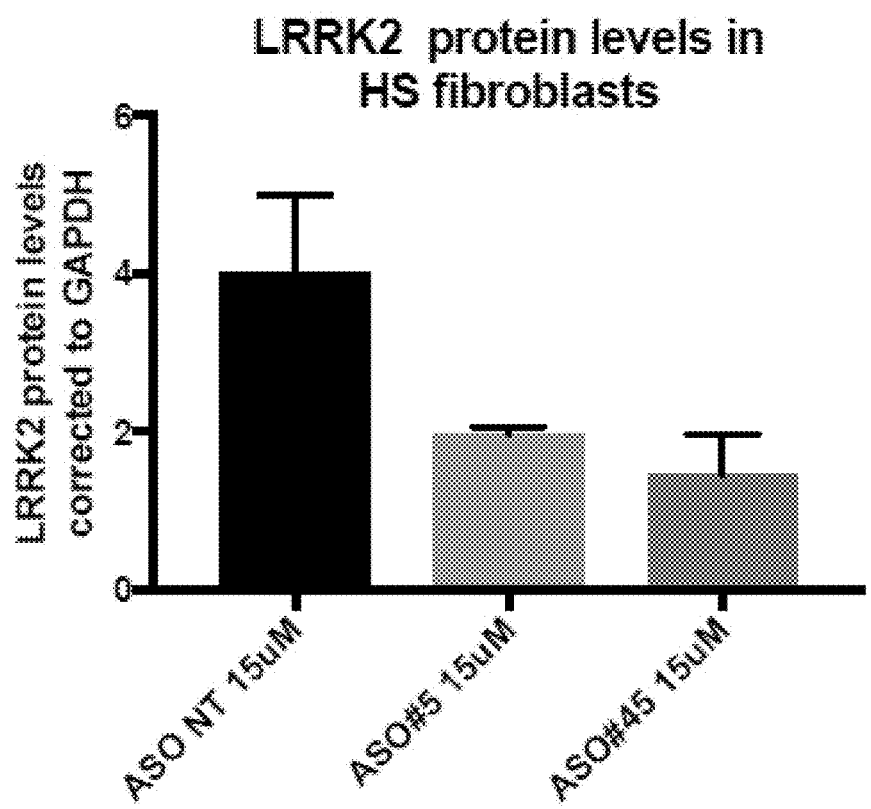
FIG. 34B shows a decrease in LRRK2 protein expression in PD patient derived fibroblasts carrying the LRRK2 R1441C mutation when treated with ASOs targeting exon 31. Treatment with 15 μM of ASO#5 or 15 μM of ASO#45 results in a decrease in LRRK2 protein levels.
Figure 34C:
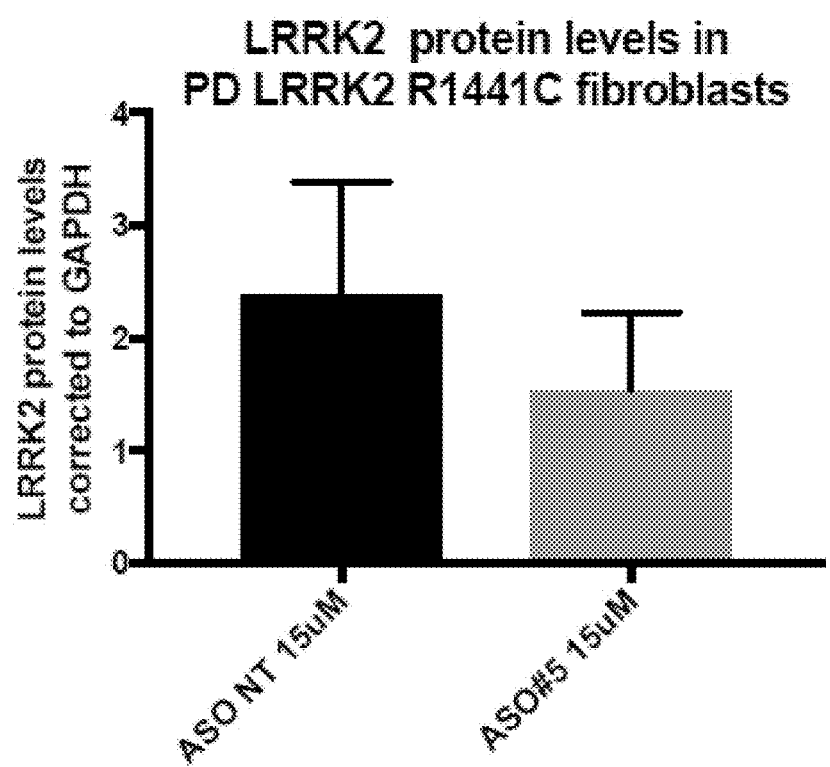
FIG. 34C shows a decrease in LRRK2 protein expression in PD patient derived fibroblasts carrying the LRRK2 R1441C mutation when treated with an ASO targeting exon 31. Treatment with 15 μM of ASO#5 results in a trend of decrease in LRRK2 protein levels.
Figure 34D:
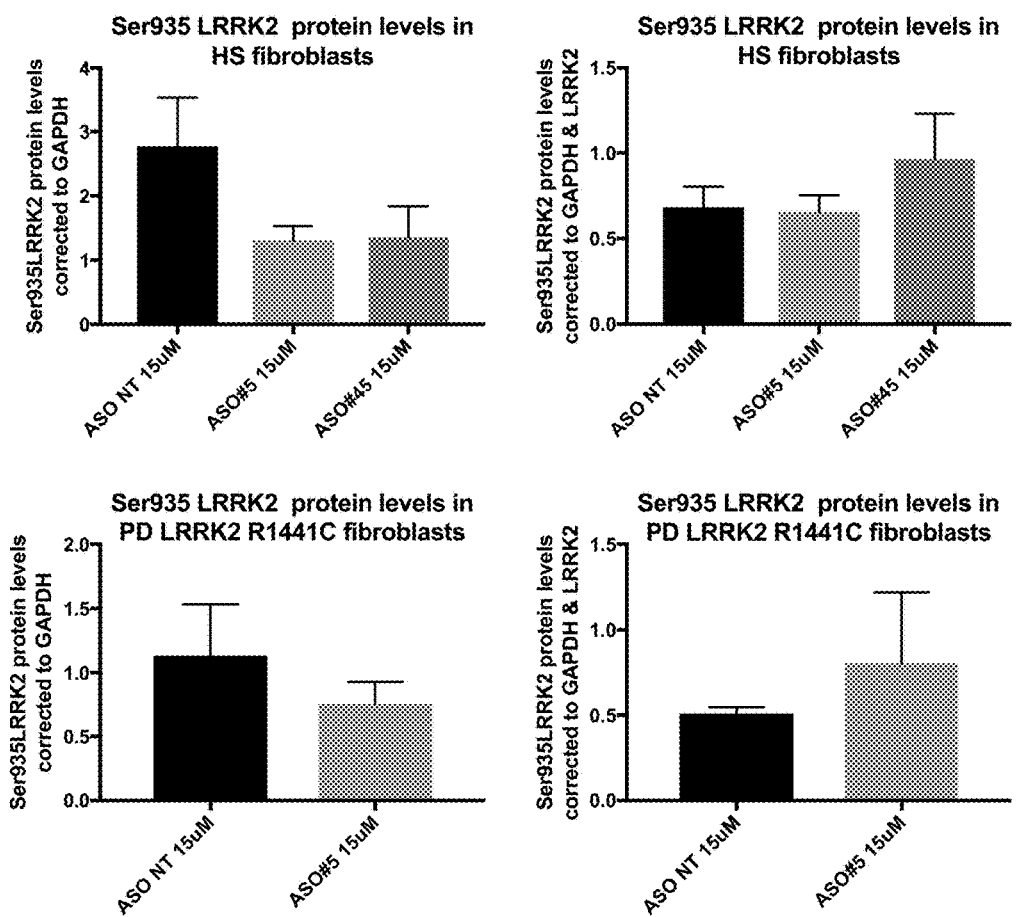
FIG. 34D shows changes in phosphorylated LRRK2 protein levels (phosphorylation at Serine 935) in HS cells and PD patient derived fibroblasts carrying the LRRK2 R1441C mutation when treated with ASOs targeting exon 31 (treatment with 15 μM of ASO#5 or 15 of ASO#45).
Figure 35:
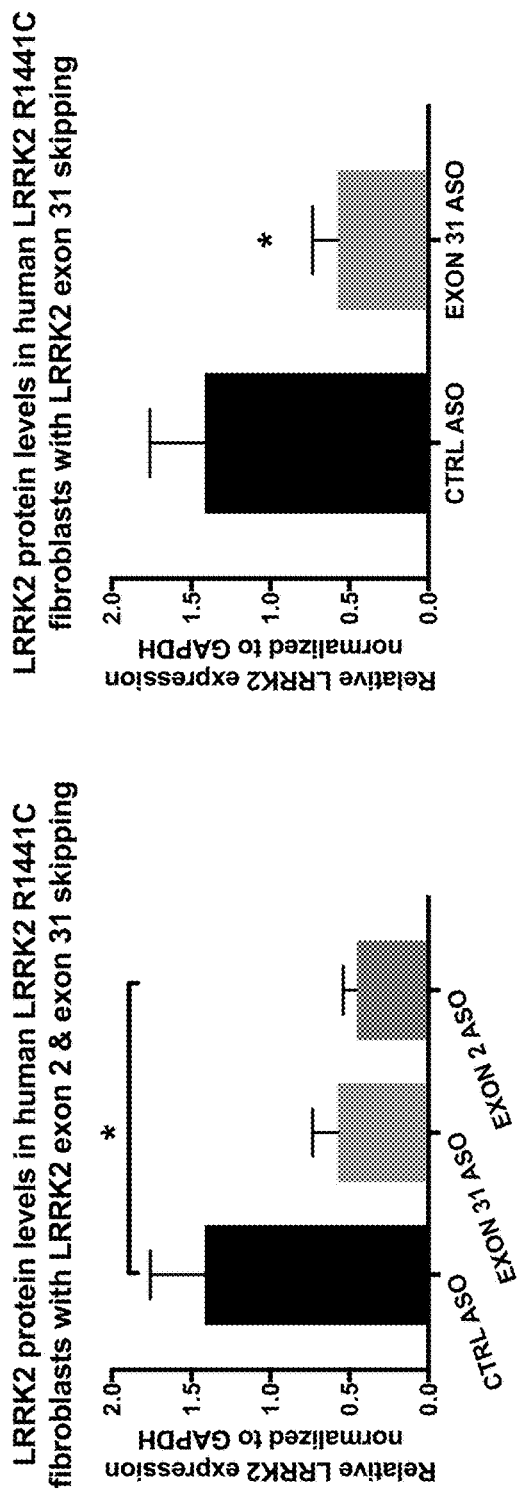
FIG. 35 shows a decrease in LRRK2 protein expression in PD patient derived fibroblasts carrying the LRRK2 R1441C mutation when treated with ASOs targeting exon 31 and exon 2. Treatment with 5 μM of ASO#5 or ASO#45 results in a decrease in LRRK2 protein levels. One way ANOVA with Dunnett's multiple testing correction & Paired T-test; *p<0.05.
Figure 37:
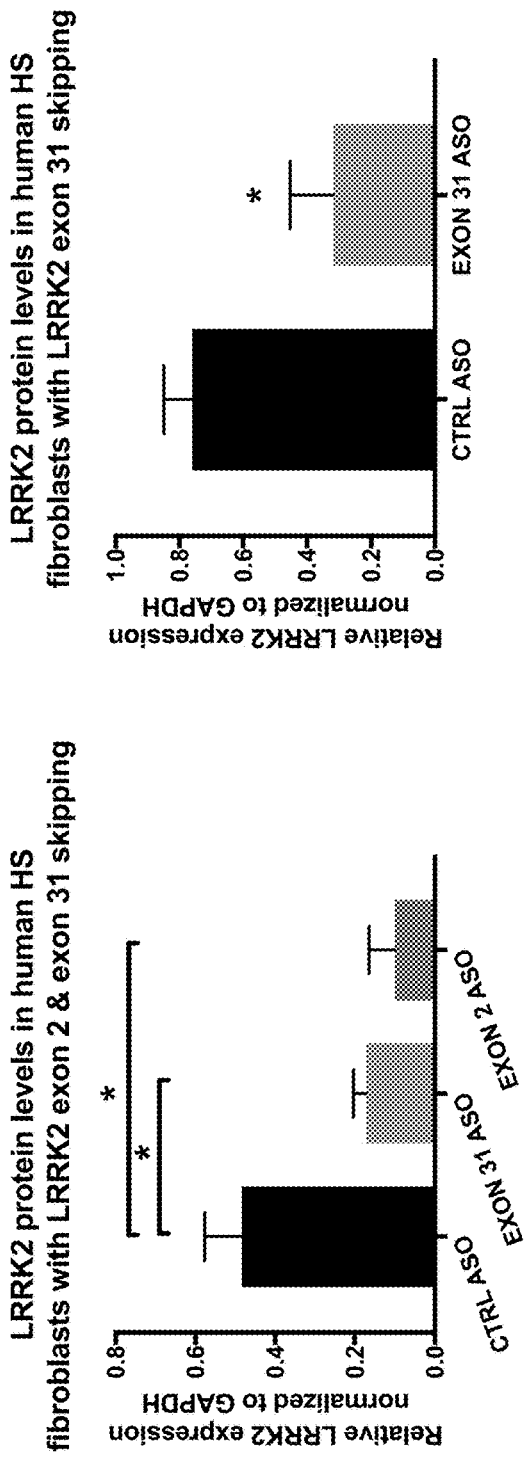
FIG. 37 shows a decrease in LRRK2 protein expression in human HS fibroblasts treated with ASOs targeting exon 31 and exon 2. Treatment with 5 μM of ASO#5 or ASO#45 results in a decrease in LRRK2 protein levels. One way ANOVA with Tukey's multiple testing correction & Paired T-test; *p<0.05.

After differentiation (DIV 35) EB iPSC-derived neurons were replated into 96 well plates at 15,000 cells per well. Five days post plating at DIV40, neurons were infected with ER stress Cignal™ Lenti Reporter Assay ERSE and ATF6 (CLS-9032L-8, CLS-6031L-8, Qiagen), at MOHO. Seven days post plating, on DIV 42, neurons were exposed to 24 hours incubation with thapsigargin (THP) at 0 nM, 1 nM, 10 nM, and 100 nM concentration. One day later luciferase activity was measured using the Dual-Glo® Luciferase Assay System (E2940, Promega) (see FIG. 13B and FIG. 13C).

For gene expression analysis, RNA was isolated from neurons cultured in a 96 well plates seeded at a density of 15,000 cells/well at DIV43 24 hours post THP treatment, using the QIAshredder™ spin columns and the RNeasy® spin column method (Qiagen, 74104). cDNA synthesis was performed according to the QuantiTect® Reverse Transcription procedure (Qiagen, 205311); QuanTitect® primer assays were used for detection of the ATF6A, ATF6B and YY1 genes (QT00083370, QT00009380, QT00052738, Qiagen), using SybrGreen detection method (Applied Biosystems, 4367659) and StepOnePlus Real-Time PCR system (Applied Biosystems) according to the manufacturer protocol. Gene expression levels were normalized to GAPDH (IDT) expression.

Cell Viability Assay:

In vitro toxicity was determined by lactate dehydrogenase (LDH) assay (Roche) to measure the conversion of a tetrazolium substrate by LDH enzyme released through the cell plasma membrane during cell death. Fibroblasts were placed in a clear, flat-bottomed 96-well plate at a density of 2,000 cells per well. One day post-plating, cells were transfected with exon 41 ASO (SEQ ID NO:02) at 1 µM, 5 µM and 15 µM and non-target ASO (SEQ ID NO:05) at 15 µM. Forty-eight hours later, cells were incubated at 37° C. with 40 µM valinomycin for 24 hours. The substrate and catalyst were applied according to the manufacturer's instructions. The LDH-based colorimetric change was analyzed according to the manufacturer's instructions using the Spectra Max Plus 384 spectrophotometer and Soft Max Pro 5.4.4 software. The optical density of each line was subtracted from a lysed control for that same line and samples were run in three technical replicates.

LRRK2 Protein Analysis in Human Fibroblasts:

Healthy subject and Parkinson's disease patient fibroblasts were plated at 500,000 cells into 24 well plate. One day post plating, fibroblasts were transfected with exon 41 (SEQ ID NO:02), exon 31 (SEQ ID NO:01), exon 2 (SEQ ID NO:07), and non-target ASO (SEQ ID NO:05) with Endo-Porter as described above. Two days later, at DIV4, cells were lysed using ice-cold RIPA lysis buffer (Thermo Fisher Scientific, PI-89900) containing Halt Protease & Phosphatase Inhibitor Cocktail (1:100, Thermo Fisher Scientific, 1861284) and 0.5M EDTA Solution (1:100, Thermo Fisher Scientific, 1861283). Samples were sonicated and protein content was quantified using the BCA Protein Assay Kit (BCA Assay, Thermo Scientific, 23227). Samples were prepared to a concentration of 40 µg in distilled water and Pierce™ Lane Marker Reducing Sample Buffer (Thermo Fisher Scientific, 39000) and boiled for 5 minutes at 100° C. Protein samples were then separated in 4-20% Tris-HCL (345-0032) Criterion precast gels (Bio-rad) and transferred onto Trans-Blot® Turbo™ 0.2 µm PVDF membranes (Bio-rad, 170-4157) by applying an electrical charge of 21 V and 2.5 A for 7 minutes. Membranes were incubated in blocking buffer (TBS, 0.1% (v/v) Tween-20 (Fisher, BP337-500) and 5% blotting grade blocker (Bio-rad, 1706404)) for 1 hour at room-temperature. Membranes were then cut and incubated with Ser935 LRRK2 UDD2 antibody (1:250, Abcam) overnight on a shaker at 4° C. The next day, blots were incubated with a goat-anti-rabbit (1:5000, Bio-rad, 170-6515) conjugated secondary antibody for 1 hour at room-temperature. Blots were developed using the Advansta WesternBright Sirius kit (Advansta, Cat. # K-12043-D10) and imaged using ChemiDoc™ XRS+ system (Bio-rad). After imaging, blots were stripped with stripping buffer, block in 5% milk-TBST solution and incubated with LRRK2 (100-500) UDD3 antibody (1:250, MRC, University of Dundee, Monoclonal Rabbit 30-12) or anti-GAPDH antibody (1:10,000 AB2302, Millipore) in blocking buffer over the weekend on a shaker at 4° C. Next, blots were incubated with a goat-anti-rabbit (1:5000, Bio-rad, 170-6515) or anti-chicken IgY HRP (1:5000, G135A, Promega) conjugated secondary antibodies for 1 hour at room-temperature. Blots were developed using the Advansta WesternBright Sirius kit (Advansta, Cat. # K-12043-D10) and imaged using ChemiDoc™ XRS+ system (Bio-rad). Blot analysis was performed using Image Lab™ analysis software.

LRRK2 Protein Analysis in Human iPSC-Derived Neurons:

Post differentiation at DIV 35, iPSC-derived neurons were plated onto 12 well plates at 500,000 cells per well. Neurons were treated 2× with exon 41 (SEQ ID NO:02), exon 31 (SEQ ID NO:01), and non-target ASOs (SEQ ID NO:05) at 10 µM concentration with Endo-Porter as described above. On day 7 post-plating, neurons were lysed using ice-cold RIPA lysis buffer (Thermo Fisher Scientific, PI-89900) containing Halt Protease & Phosphatase Inhibitor Cocktail (1:100, Thermo Fisher Scientific, 1861284) and 0.5M EDTA Solution, (1:100, Thermo Fisher Scientific, 1861283). Samples were sonicated and protein content was quantified using the BCA Protein Assay Kit (BCA Assay, Thermo Scientific, 23227). Samples were prepared to a concentration of 40 µg in distilled water and Pierce™ Lane Marker Reducing Sample Buffer (Thermo Fisher Scientific, 39000) and boiled for 5 minutes at 100° C. Protein samples were then separated in 4-20% Tris-HCL (345-0032) Criterion precast gels (Bio-rad) and transferred onto Trans-Blot® Turbo™ 0.2 µm PVDF membranes (Bio-rad, 170-4157) by applying an electrical charge of 21 V and 2.5 A for 7 minutes. Membranes were incubated in blocking buffer (TBS, 0.1% (v/v) Tween-20 (Fisher, BP337-500) and 5% blotting grade blocker (Bio-rad, 1706404)) for 1 hour at room-temperature. Membranes were then cut and incubated with LRRK2 (100-500) UDD3 antibody (1:250, MRC, University of Dundee, Monoclonal Rabbit 30-12) or anti-GAPDH antibody (1:10,000 AB2302, Millipore) in blocking buffer over the weekend on a shaker at 4° C. Next, blots were incubated with goat-anti-rabbit (1:5000, Bio-rad, 170-6515) or anti-chicken IgY HRP (1:5000, G135A, Promega) conjugated secondary antibodies for 1 hour at room-temperature. Blots were developed using the Advansta Western-Bright Sirius kit (Advansta, Cat. # K-12043-D10) and imaged using ChemiDoc™ XRS+ system (Bio-rad). Blot analysis was performed using Image Lab™ analysis software.

Figure 3B:
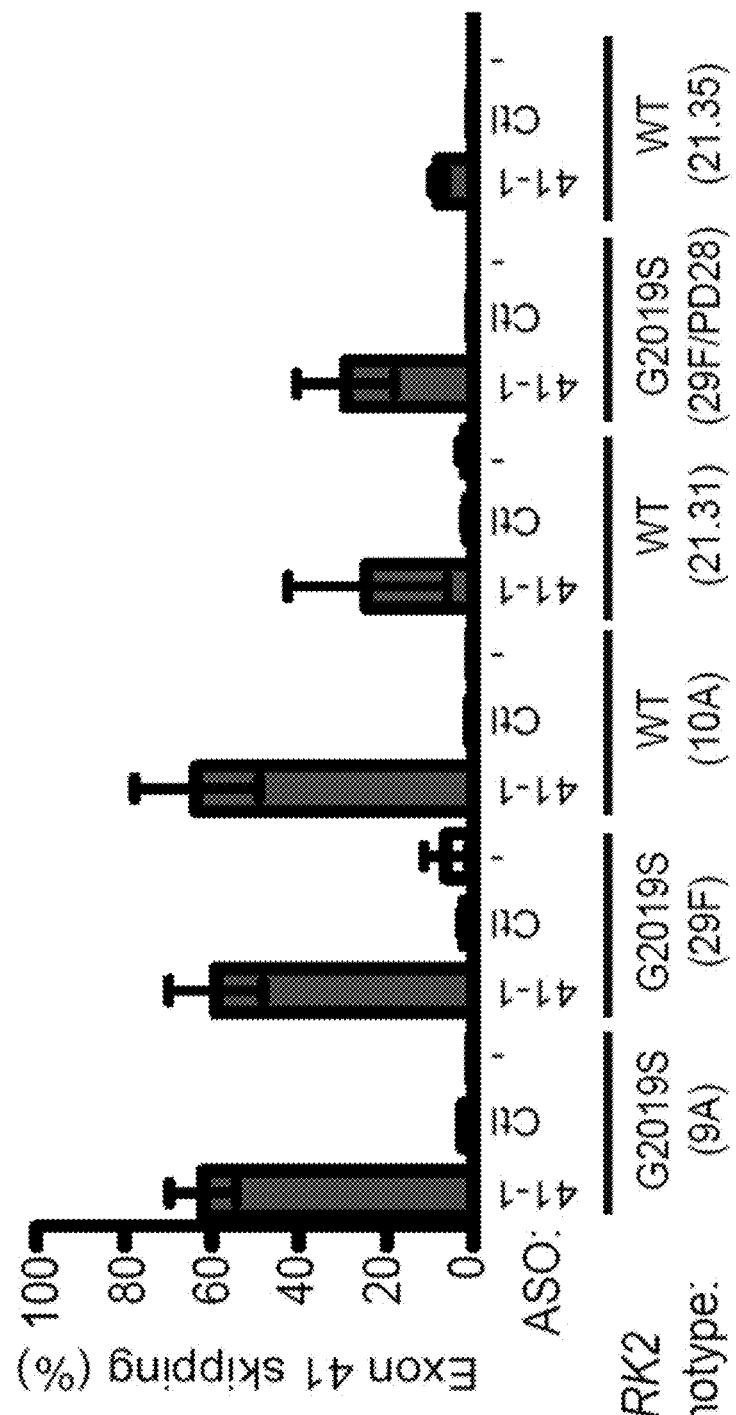
FIG. 3B demonstrates that antisense oligonucleotides (ASO-41-1) successfully induces skipping of LRRK2 exon 41 containing the G2019S mutation in neurons derived from human induced pluripotent stem cells.
Figure 38B:
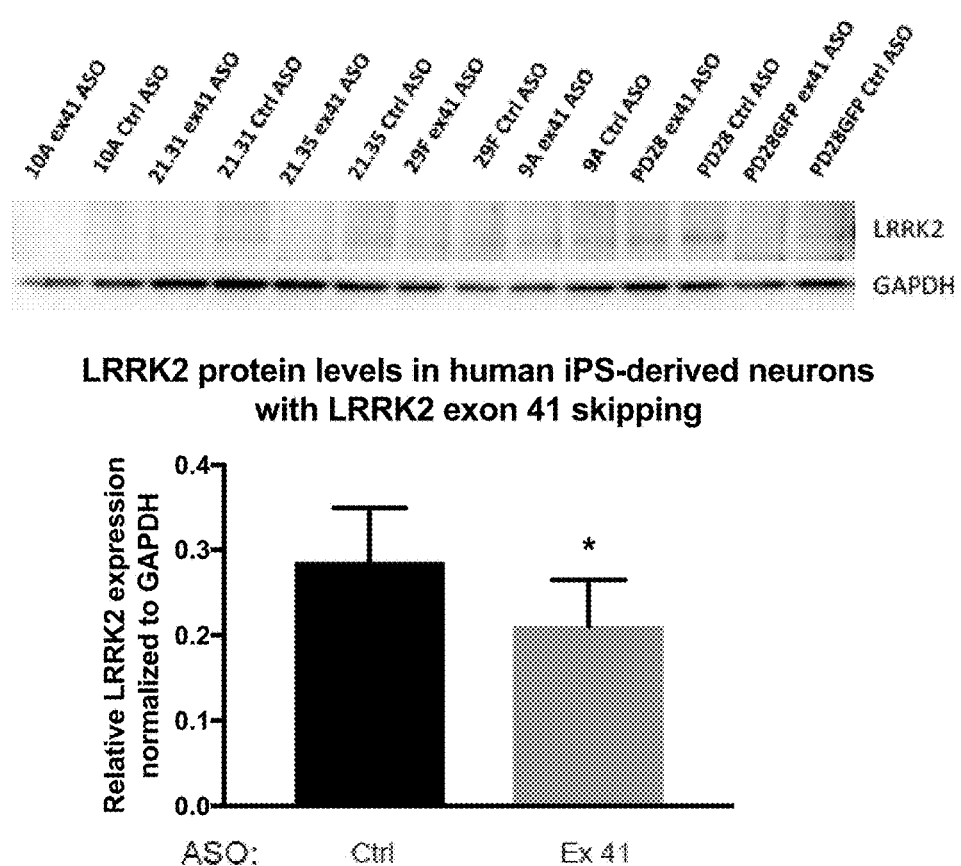
FIG. 38B shows a decrease in LRRK2 protein expression in iPS-derived neurons from healthy subject and PD patient neurons carrying the LRRK2 G2019S mutation treated with an ASO targeting exon 41 (Ex41) compared to non-target ASO (Ctrl). Treatment with 2×10 μM of ASO#6 results in a decrease in LRRK2 protein levels. Ratio Paired t-test, *p<0.05.
Figure 38C:
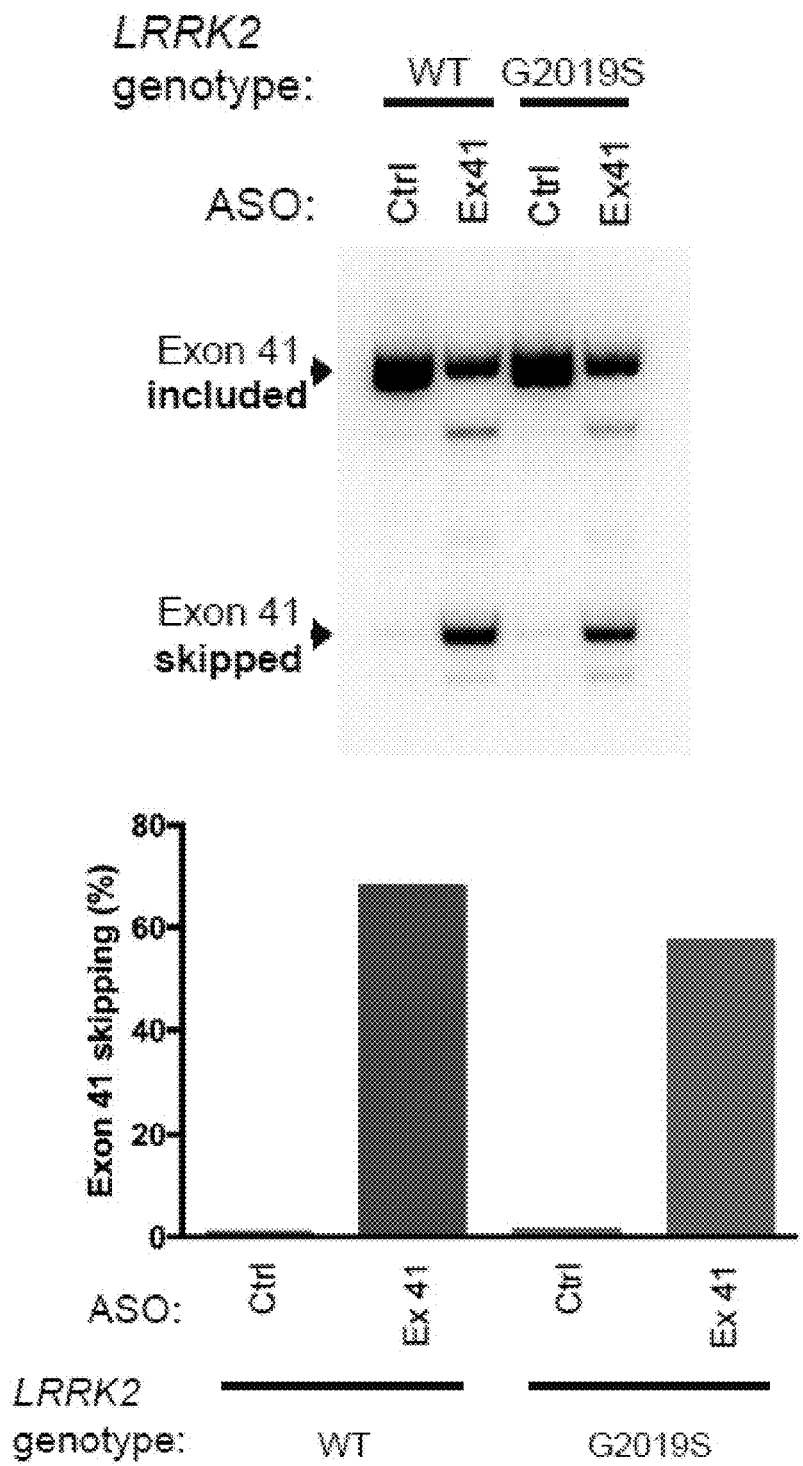
FIG. 38C shows that ASOs directed to exon 41 induce exon 41 skipping in iPS-derived midbrain neurons with WT LRRK2 or LRRK2 carrying the G2019S mutation. Cells were treated with 2×10 μM of an ASO specific to exon 41 (ASO#6; SEQ ID NO:02).

Example 1: Antisense Oligonucleotides Induce Skipping of Exon 41 and Exon 31 in Human LRRK2 Gene in Human iPS-Derived Neurons ASO 41-1 (see Table 3; SEQ ID NO:02) was tested in the human iPS-derived neural cell line. ASO 41-1 (10 µM final concentration, one treatment at DIV41) was transfected into cells using Endo-Porter (GeneTools) according to manufacturer's protocol. FIGS. 3A and 3B demonstrate that ASO 41-1 induces skipping of targeted exon 41 of LRRK2 with or without the G2019S mutation (also see FIG. 38A and FIG. 38C).

Figure 4A:
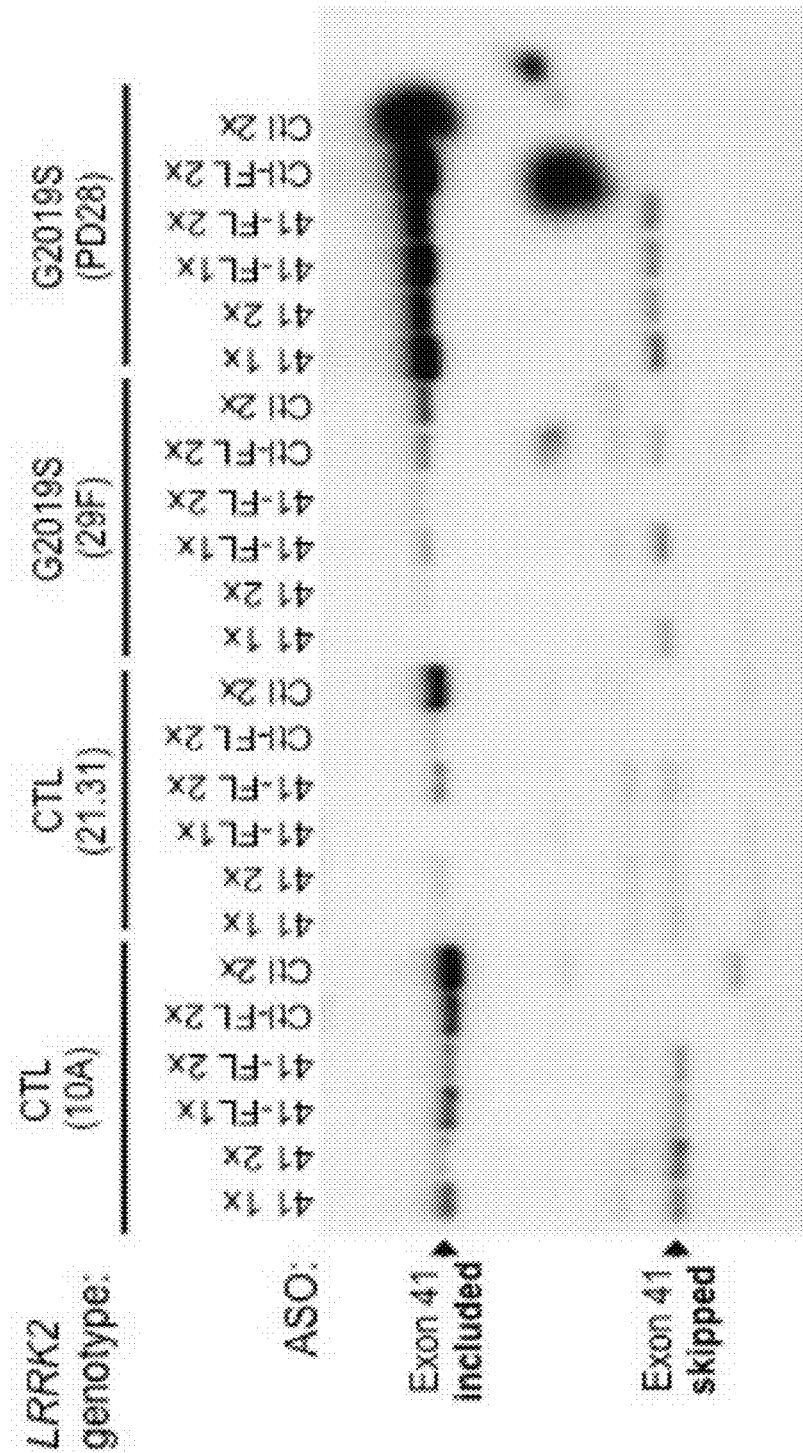
FIG. 4A shows an electrophoretic analysis of the full length LRRK2 RNA product containing exon 41 (top lane) and LRRK2 RNA product with exon 41 skipped (bottom lane) after ASO treatment. Treatment conditions: 41 1x-single treatment of cells with exon 41 ASO, 41 2x-double treatment of cells with exon 41 ASO, 41-FL 1x-single treatment of cells with exon 41 Fluorescent ASO, 41 2x-double treatment of cells with exon 41 Fluorescent ASO, Ctl-FL 2x-double treatment of cells with non-target Fluorescent ASO, Ctl 2x-double treatment of cells with non-target Fluorescent ASO. Results demonstrate that LRRK2 exon 41 skipping induced by antisense oligonucleotides (ASO) in iPS-derived neurons derived from healthy subject controls (CTRL 10A and 21.31) or PD patients carrying LRRK2 G2019S mutation (G2019S 29F and PD28).
Figure 5D:
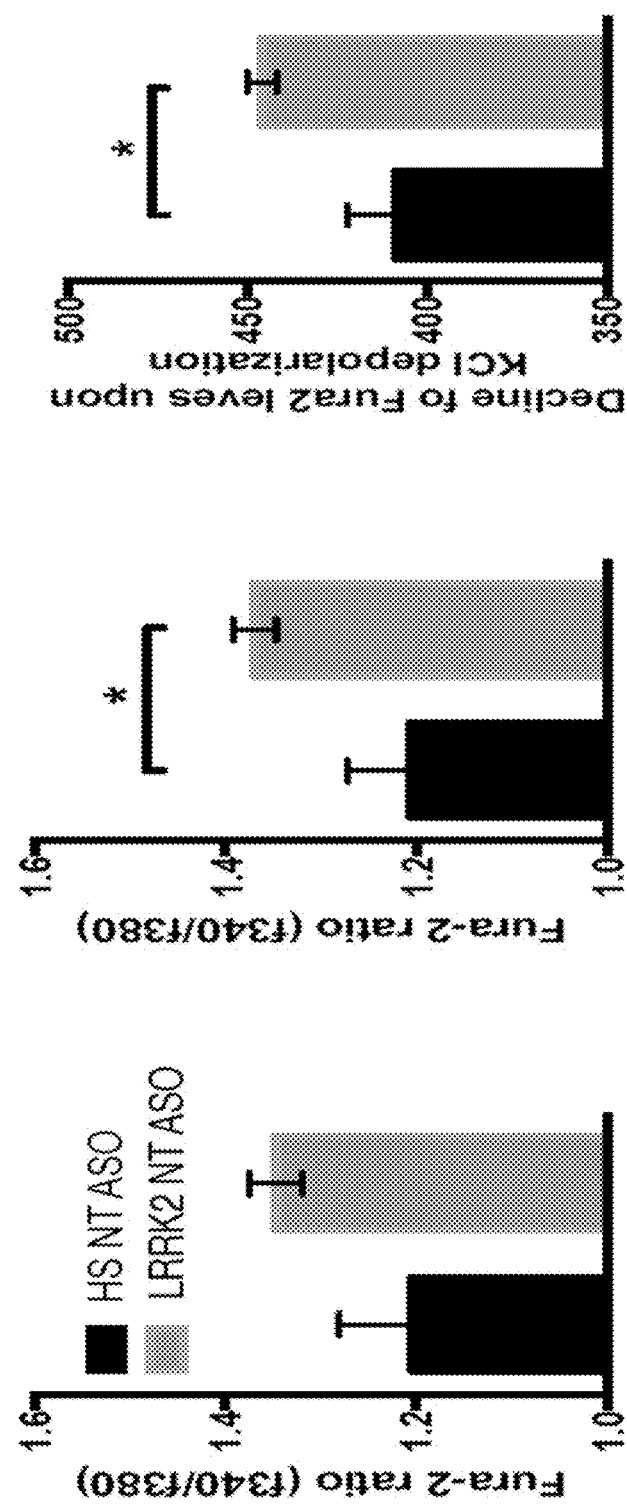
FIG. 5D shows that upon Serca inhibition with 10 nM thapsigargin (THP), intracellular calcium levels were significantly increased in human iPS neurons carrying LRRK2 G2019S mutation compared to HS control. Detailed analysis showed an increase in the 2nd calcium peak amplitude upon KCl depolarization and an increase in the unbound calcium levels indicating decreased calcium buffering. Results demonstrate iPS-derived neurons carrying LRRK2 G2019S mutation show altered calcium homeostasis after ER calcium pump Serca inhibition, which can be rescued by LRRK2 G2019S antisense oligonucleotide.
Figure 5E:
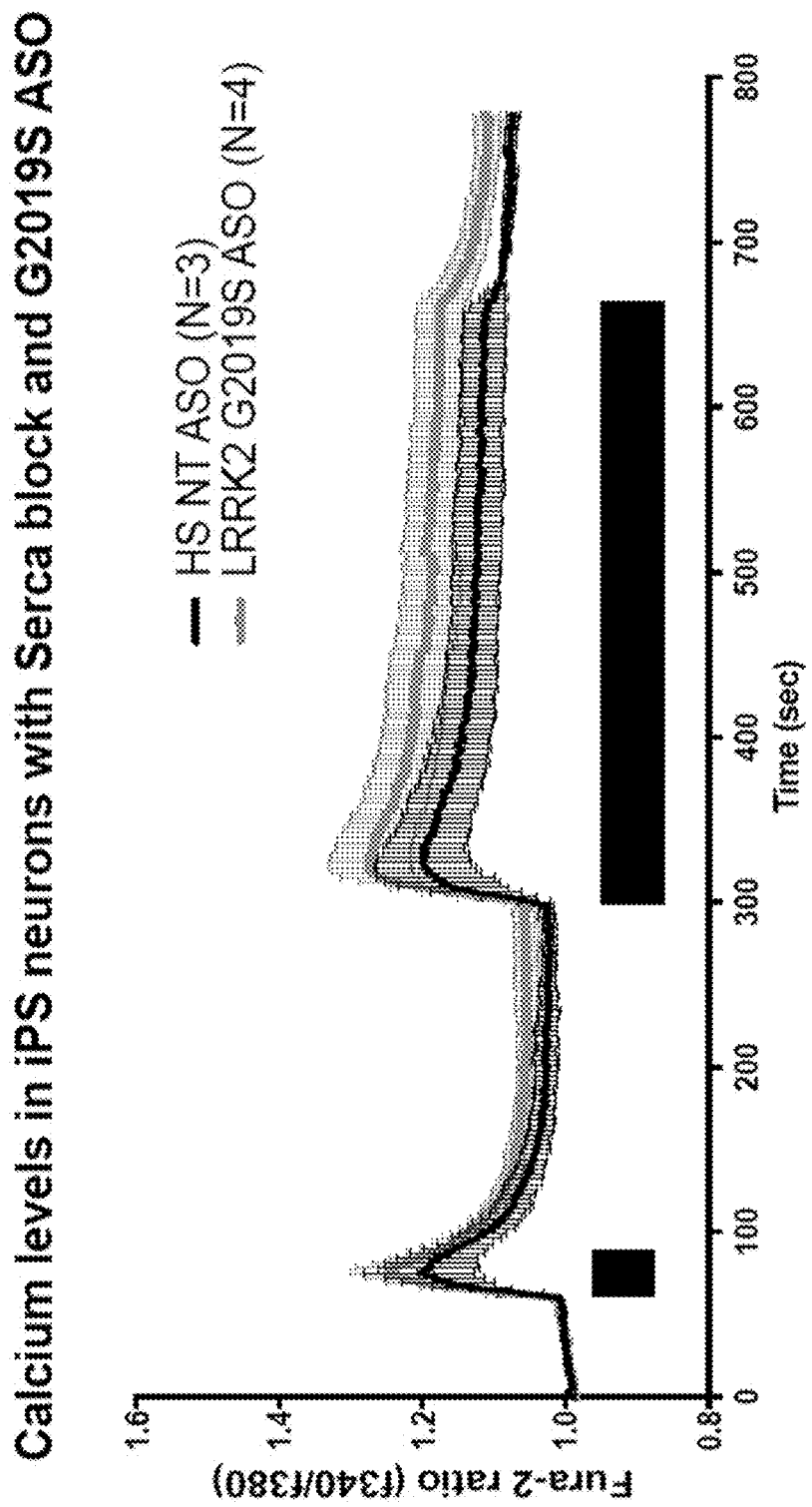
FIG. 5E shows LRRK2 exon 41 G2019S targeting antisense oligonucleotide (G2019S ASO) normalizes the intracellular calcium levels in Serca blocked iPS-derived neurons carrying LRRK2 G2019S mutation. Both the calcium amplitude during the 2nd KCl stimulation and the unbound calcium levels show equal levels when compared to the HS control neurons treated with non-target ASO (NT ASO). Data was collected from fluorescein positive ASO transfected 4 PD patient iPS-derived neuronal lines carrying LRRK2 G2019S mutation and 3 healthy subject control lines; each line represents a pool of 3 technical replicates per condition per line. Statistical analysis was performed using unpaired student T-test. *$p<0.05$.). Results demonstrate rescue of the LRRK2 G2019S induced pathology in iPS-derived neurons using LRRK2 exon 41 skipping antisense oligonucleotide strategy functional validation studies.
Figure 5F:
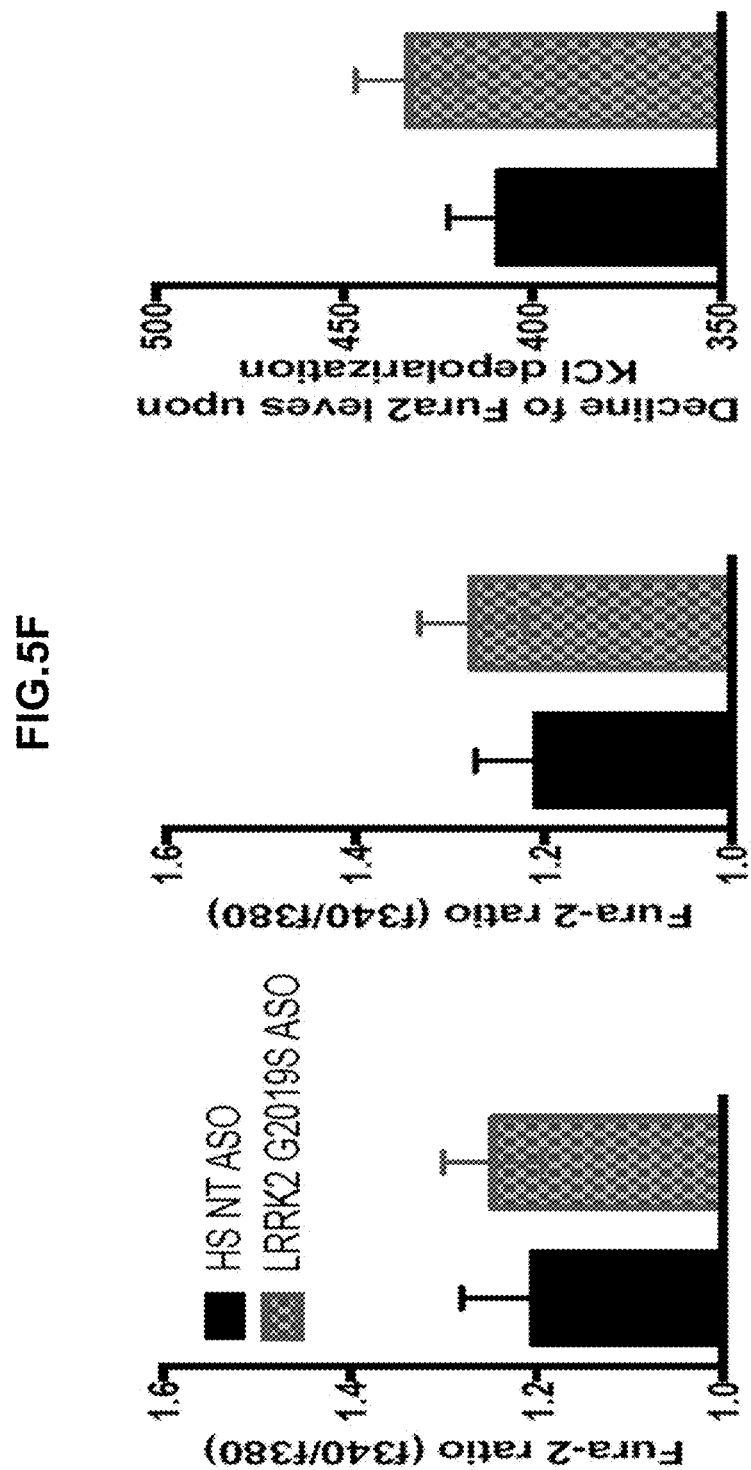
FIG. 5F shows LRRK2 exon 41 G2019S targeting antisense oligonucleotide (G2019S ASO) normalizes the intracellular calcium levels in Serca blocked iPS-derived neurons carrying LRRK2 G2019S mutation. Both the calcium amplitude during the 2nd KCl stimulation and the unbound calcium levels show equal levels when compared to the HS control neurons treated with non-target ASO (NT ASO). Data was collected from fluorescein positive ASO transfected 4 PD patient iPS-derived neuronal lines carrying LRRK2 G2019S mutation and 3 healthy subject control lines; each line represents a pool of 3 technical replicates per condition per line. Statistical analysis was performed using unpaired student T-test. *p<0.05.). Results demonstrate rescue of the LRRK2 G2019S induced pathology in iPS-derived neurons using LRRK2 exon 41 skipping antisense oligonucleotide strategy functional validation studies.
Figure 6C:
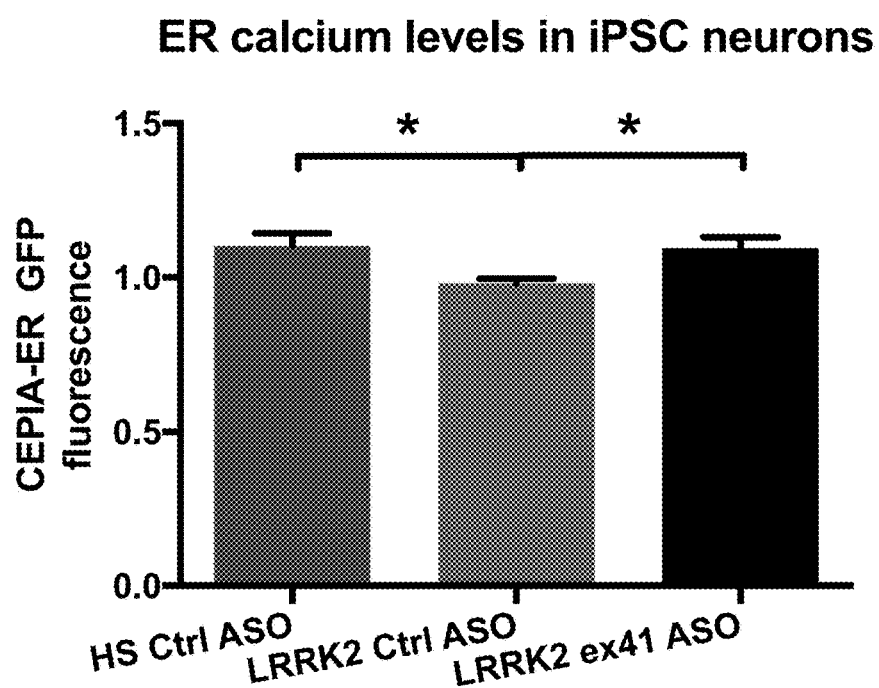
FIG. 6C shows ER-calcium levels in the control ASO (SEQ ID NO:05) and exon 41 ASO (SEQ ID NO:02) treated iPS neurons carrying LRRK2 G2019S mutation compared to the healthy subject (HS) control. ER calcium levels were measured by total CEPIA-ER-GFP expression emission. Results demonstrate that iPS-derived neurons carrying LRRK2 G2019S mutation show decreased ER-calcium levels, which can be successfully rescued by antisense oligonucleotide induced exon 41 skipping. Statistical analysis was performed using One way ANOVA with Holm-Sidak's multiple testing correction. *p<0.05.
Figure 7A:
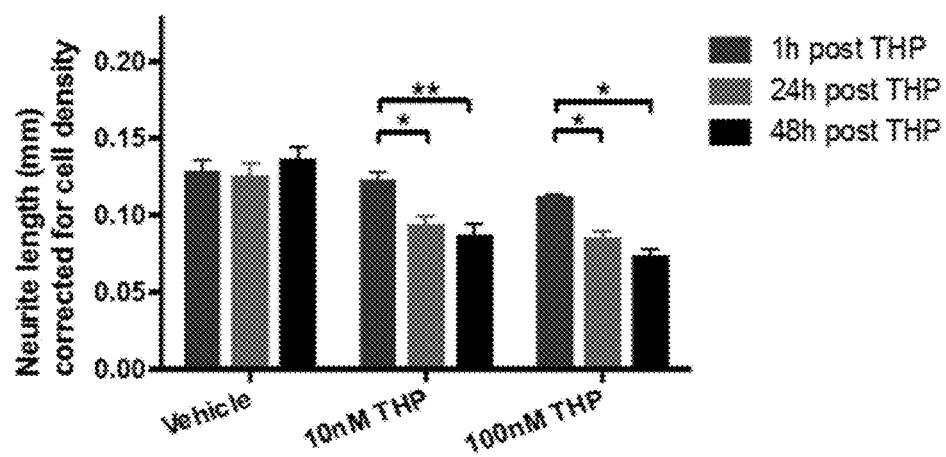
FIG. 7A shows that neurite length is shortened in LRRK2 G2019S neurons following treatment with ER calcium pump Serca inhibitor thapsigargin (THP) by 24 hours and 48 hours post 10 nM and 100 nM treatment (N=3). One way Repeated measure ANOVA with Dunnett's multiple testing correction, *p<0.05, **p<0.01.
Figure 7B:
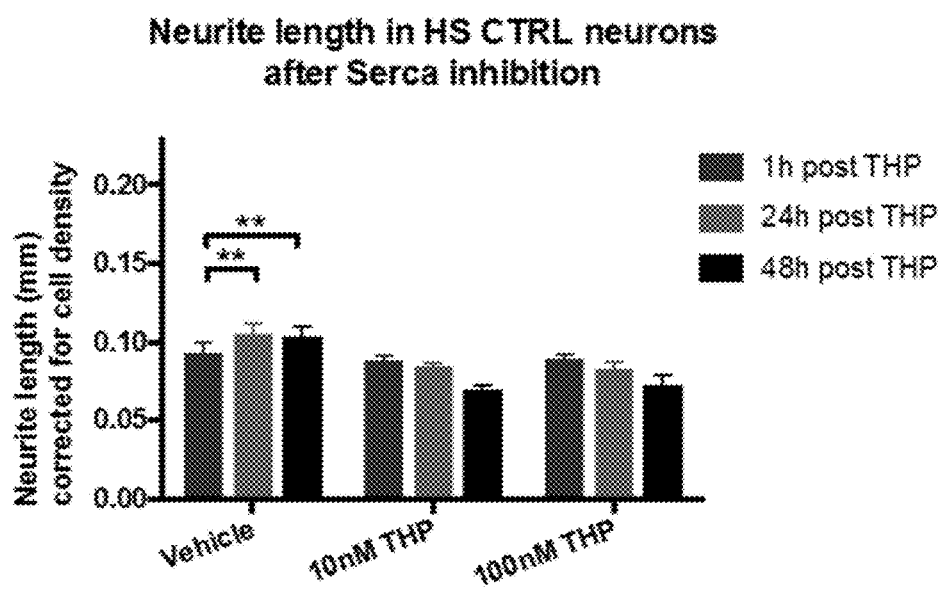
FIG. 7B shows that neurite length is unaffected in WT neurons (N=3) following treatment with a SERCA inhibitor, but rather, we observe an increase of the neurite length in the vehicle treated cells. One way Repeated measure ANOVA with Dunnett's multiple testing correction, **p<0.01.
Figure 7C:
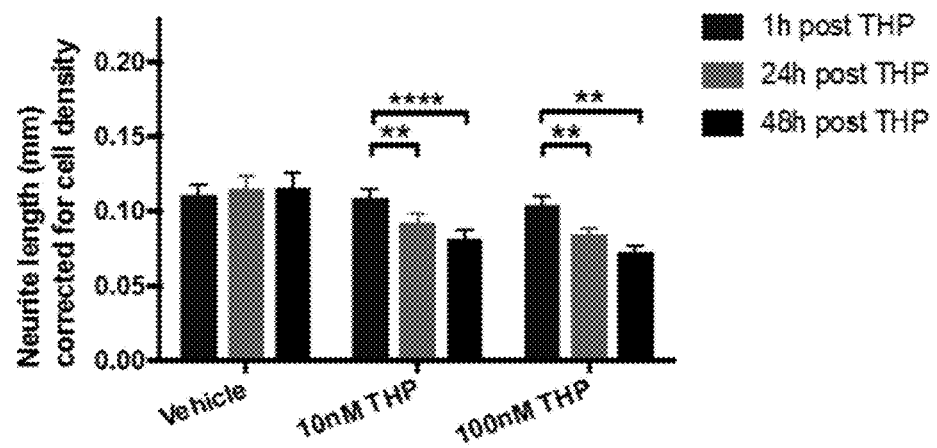
FIG. 7C shows that neurite length is shortened in LRRK2 G2019S neurons following treatment with a SERCA inhibitor in an independent Parkinson's disease patient iPSC-derived neuronal cohort (N=4). One way Repeated measure ANOVA with Dunnett's multiple testing correction, *p<0.05, **p<0.01.
Figure 7D:
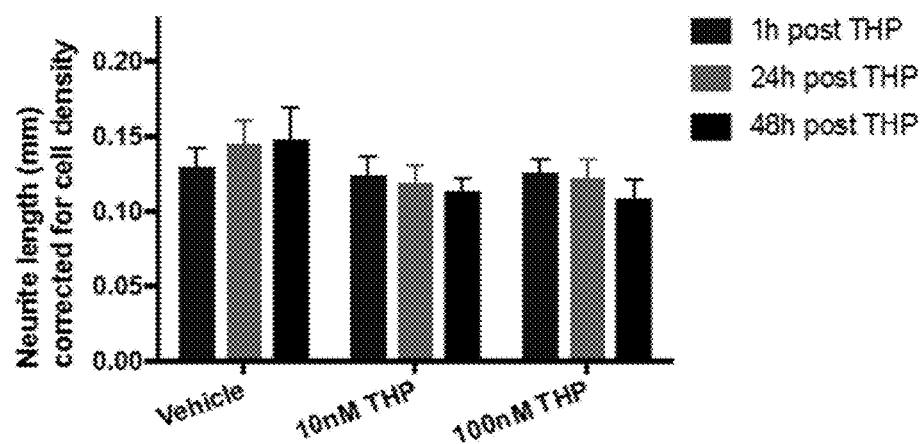
FIG. 7D shows that neurite length is unaffected in gene corrected neurons following treatment with a SERCA inhibitor. One way Repeated measure ANOVA with Dunnett's multiple testing correction.
Figure 7E:
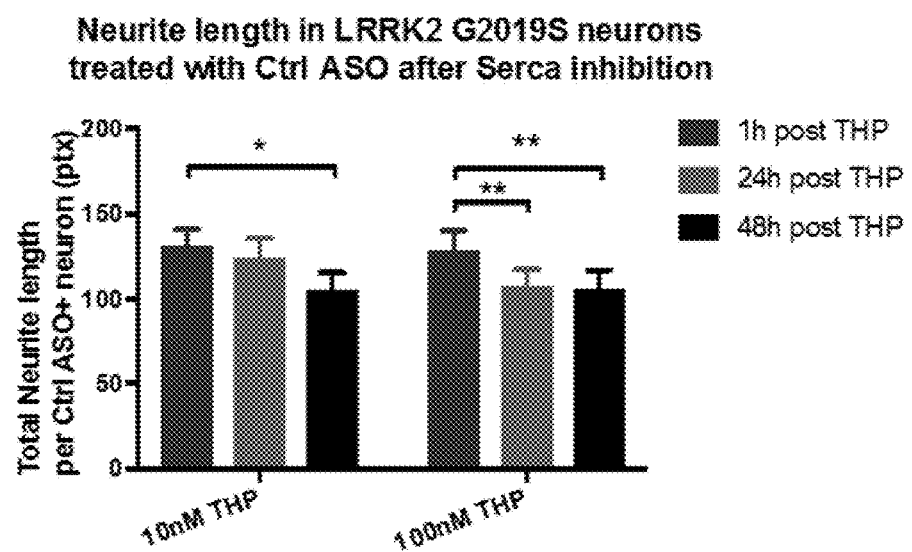
FIG. 7E shows that neurite length is shortened in LRRK2 G2019S neurons following treatment with a non-specific control ASO following treatment with a SERCA inhibitor. One way Repeated measure ANOVA with Dunnett's multiple testing correction. *p<0.05, **p<0.01.
Figure 7F:
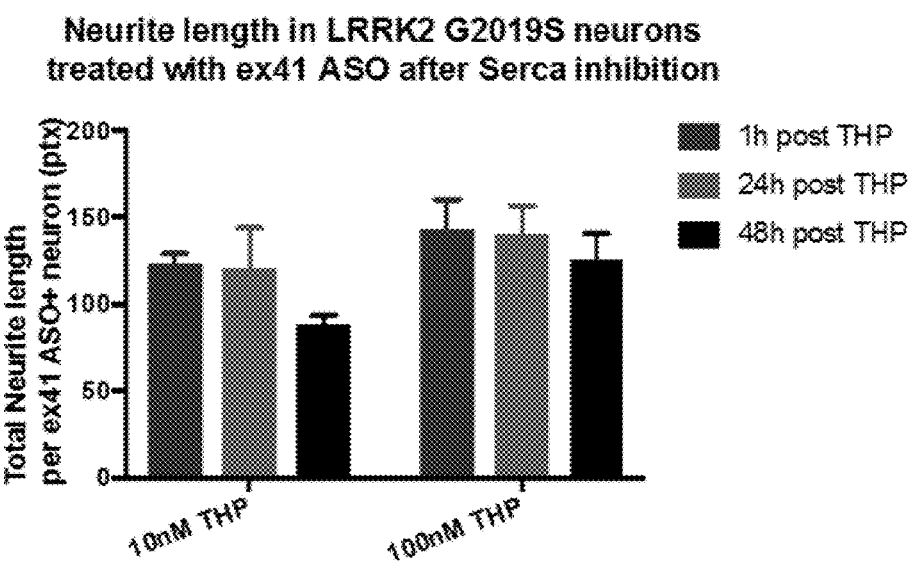
FIG. 7F shows that exon 41 LRRK2 ASO induced skipping rescues neurite outgrowth THP induced collapse in LRRK2 G2019S neurons. One way Repeated measure ANOVA with Dunnett's multiple testing correction.
Figure 40:
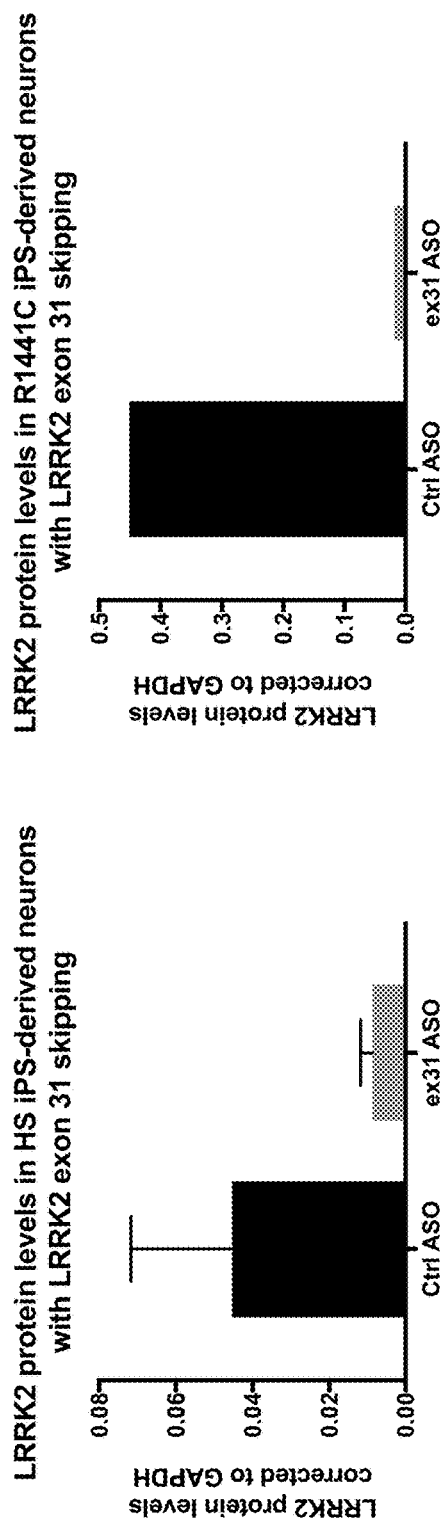
FIG. 40 shows LRRK2 protein levels after exon 31 ASO induced skipping in iPS-derived neurons. ASO#5 decreases LRRK2 protein levels in iPS-derived neurons expressing WT or R1441C mutant LRRK2.

ASO 41-1 and a non-sense control were tested in human iPS-derived neurons (ASO41-1 is 5'-AGACAGACCTGAT-CACCTACCTGGT-3'; SEQ ID NO: 2) and a non-sense control oligonucleotide sequence (Non-sense control is 5'-CCTCTTACCTCAGTTACAATTTATA-3'; SEQ ID NO: 5) either once (5 days post differentiation, DIV37) or two times (2 and 5 days post end of the differentiation (DIV37 and DIV41)). Each time neurons were treated with 10 µM LRRK2 ASOs using Endo-Porter delivery method according to the manufacturer's protocol (Gene Tools, 4 µl per 1 mL solution). Exon skipping efficiency was also assessed by comparing between the non-tag and the carboxyflourescein-3' tag ASO sequences. RNA was collected 48 hours post the second transfection (DIV43). LRRK2 exon 41 skipping was induced by ASO 41-1 in iPS-derived neurons derived from healthy subject controls (CTRL 10A and 21.31) or PD patients carrying LRRK2 G2019S mutation (G2019S 29F and PD28) (see FIG. 4A and FIG. 4B). FIG. 39 shows exon 31 skipping by ASO#5 (SEQ ID NO:01) in iPSC-derived human neurons either from a control healthy subject (N=3) or PD patient carrying the LRRK2 R1441C mutation (N=1). LRRK2 protein levels were also decreased in iPS-derived neurons by ASOs targeting either exon 41 or exon 31 (see FIG. 38B and FIG. 40)

TABLE 3

Antisense oligonucleotide targeting LRRK2 induce exon 41 skipping.

| Name | Target Exon | Sequence | % skipped | SEQ ID NO. |
|---|---|---|---|---|
| 41-1 | 41 | AGACAGACCTGATCACCTACCTGGT | 62 | SEQ ID NO. 2 |

* percent of the mRNA transcripts that skip out the targeted exon

Figure 2:
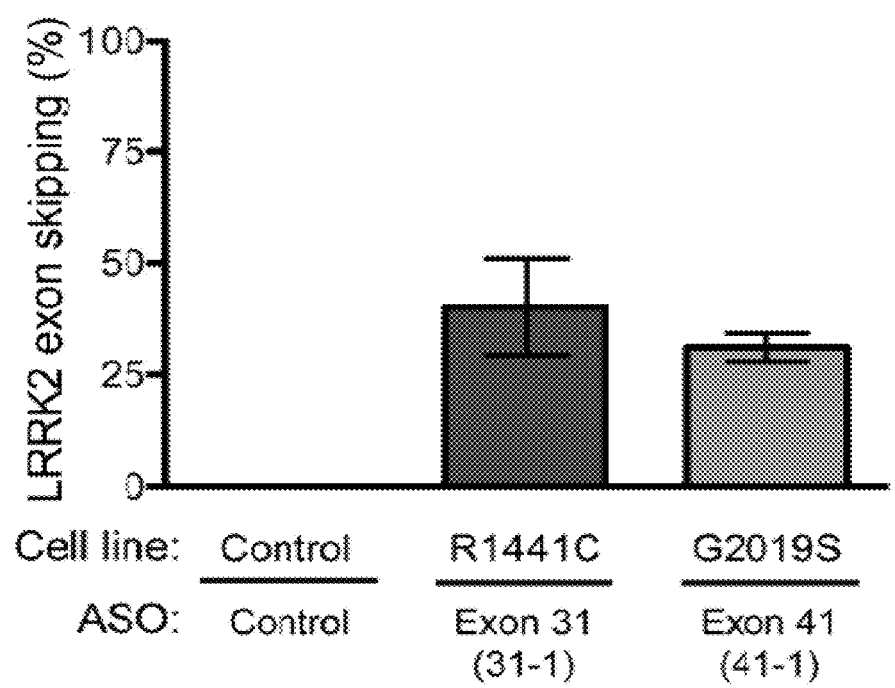
FIG. 2 demonstrates antisense oligonucleotides, ASO-31-1 (SEQ ID NO: 01) and ASO-41-1 (SEQ ID NO: 02) successfully reduce full-length LRRK2 expression by inducing skipping of LRRK2 exon 31 and 41 containing the R1441C and G2019S mutation, respectively, in fibroblast cells from Parkinson's patients.

Example 2: Antisense Oligonucleotides Successfully Reduce Full-Length LRRK2 Expression of LRRK2 Exon 31 and 41 in Fibroblast Cells from Parkinson's Patients Various ASOs (see Table 4; SEQ ID NOs: 1 and 2) were tested in human fibroblast cells from one healthy subject control and two patients with Parkinson's disease one carrying the R1441C mutation and one carrying the G2019S mutation. ASOs (7.5 µM final concentration of either ASO 31-1 or ASO 41-1) were transfected into cells using Endo-Porter (GeneTools) according to manufacturer's protocol. FIG. 2 demonstrates that ASOs 31-1 and 41-1 induce skipping of targeted exons 31 and 41 in human LRRK2, respectively.

TABLE 4

Antisense oligonucleotides targeting LRRK2 induce exon skipping

| Name | Target Exon | Sequence | % skipped | SEQ ID NO. |
|---|---|---|---|---|
| 31-1 | 31 | CTACCAGCCTACCATGTTACCTTGA | 40 | SEQ ID NO. 1 |
| 41-1 | 41 | AGACAGACCTGATCACCTACCTGGT | 31 | SEQ ID NO. 2 |

* percent of the mRNA transcripts that skip out the targeted exon

The results provided in the examples and figures above demonstrate that: 1) human neurons carrying LRRK2 G2019S mutation show a decreased level of the UPR response after ER calcium depletion indicating a lower capacity to adapt to the ER stress; 2) LRRK2 G2019S iPS-derived neurons have a decreased neurite integrity during ER stress; 3) intracellular calcium homeostasis is dysregulated in iPS-derived PD patient neurons carrying LRRK2 G2019S mutation during ER stress; and 4) ER calcium levels, intracellular calcium uptake (during ER stress) and neurite integrity (during ER stress) can be restored in LRRK2 G2019S neurons upon antisense oligonucleotide treatment targeting the G2019S mutation.

Example 3: Antisense Oligonucleotides Induced Exon Skipping in Fibroblast Cells from Parkinson's Patients Various ASOs (see Table 5) were tested in human fibroblast cells from one healthy subject control and two patients with Parkinson's disease one carrying the R1441C mutation and one carrying the G2019S mutation. ASOs (at concentrations of 1.0 µM, 5 µM, 7.5 µM, 15 µM, 22.5 µM, or 45 µM) were transfected into cells using Endo-Porter (GeneTools) according to manufacturer's protocol. FIGS. 16-26 and 38-39 demonstrate that the ASOs disclosed in Table 5 induce skipping of targeted exons in human LRRK2.

TABLE 5

Antisense oligonucleotides targeting LRRK2.

| ASO Name | Exon | Sequence (SEQ ID NO.) |
|---|---|---|
| ASO#23 or ASO 4-1 | exon 4 | ATACACATATTACCTGAAGTTAGGA (SEQ ID NO: 06) |
| ASO#45 or ASO 2-1 | exon 2 | AGTGAAAACAATGCCTTTACCTGCT (SEQ ID NO: 07) |
| ASO#46 41-2 | exon 41 | GGTATCTGCCAGAAAATGCACAGGA (SEQ ID NO: 08) |
| ASO#284 | exon 41 - G2019 mutant specific | AATGCtGTAGTCAGCAATCTTTGCA (SEQ ID NO: 09) |
| ASO#6 or ASO 41-1 | exon 41 | AGACAGACCTGATCACCTACCTGGT (SEQ ID NO: 02) |

TABLE 5-continued

Antisense oligonucleotides targeting LRRK2.

| ASO Name | Exon | Sequence (SEQ ID NO.) |
|---|---|---|
| ASO#5 or ASO 31-1 | exon 31 | CTACCAGCCTACCATGTTACCTTGA (SEQ ID NO: 01) |

Example 4: Antisense Oligonucleotides Successfully Reduce Full-Length LRRK2 Expression in Fibroblast Cells from Parkinson's Patients Various ASOs (see Table 5) were tested in human fibroblast cells from three healthy subject control and three patients with Parkinson's disease carrying either the R1441C mutation or the G2019S mutation. ASOs (at concentrations of 1.0 µM, 5 µM and 15 µM) were transfected into cells using Endo-Porter (GeneTools) according to manufacturer's protocol. FIGS. 31-37 demonstrate that the ASOs disclosed in Table 5 induce skipping of targeted exons in human LRRK2 and can reduce LRRK2 protein levels in the patient derived cells.

Example 5: Mutant LRRK2 Dependent Dysregulation of Mitophagy

Various ASOs (see Table 5) were tested in human fibroblast cells from five healthy subject control and five patients with Parkinson's disease either carrying the R1441C mutation or the G2019S mutation. ASOs (at concentrations of 1.0 µM, or 5 µM) were transfected into cells using Endo-Porter (GeneTools) according to manufacturer's protocol. FIGS. 25, and 27-30 demonstrate that the ASOs disclosed in Table 5 induce skipping of targeted exons in human LRRK2 and can successfully rescue of mitophagic flux in LRRK2 G2019C or LRRK2 R1441C fibroblasts upon LRRK2 exon skipping.

Example 6: Exon 41 LRRK2 ASO Skipping Rescues Neurite Outgrowth THP Induced Collapse in LRRK2 G2019S Neurons After differentiation iPS-derived neurons were replated for live cell phase imaging of neurite outgrowth. Seven days post plating, neurons were exposed to thapsigargin (THP) toxicity at 0 nM, 10 nM, and 100 nM concentrations and the live cell imaging was started immediately using the IncuCyte® Zoom live imaging system (Essen BioScience). Neurite length per cell body cluster was measured using the IncuCyte® imaging system or ImageJ software. FIG. 7 demonstrates that exon 41 LRRK2 ASO skipping rescues neurite outgrowth in LRRK2 G2019S neurons.

Figure 8A:
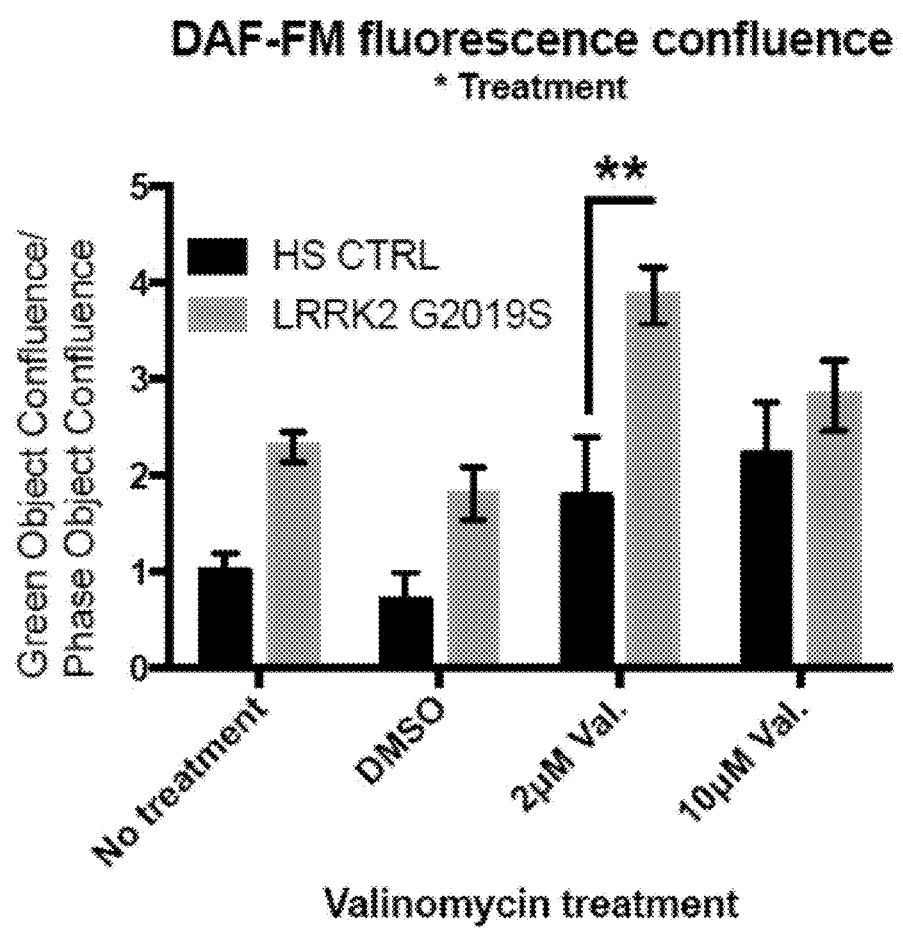
FIG. 8A shows the DAF-FM fluorescence confluence and the nitric oxide levels in LRRK2 G2019S iPS-derived neurons after valinomycin toxicity. Results demonstrate that an increase in RNS in LRRK2 G2019S neurons after mitochondrial depolarization induced through valinomycin toxicity.
Figure 8B:
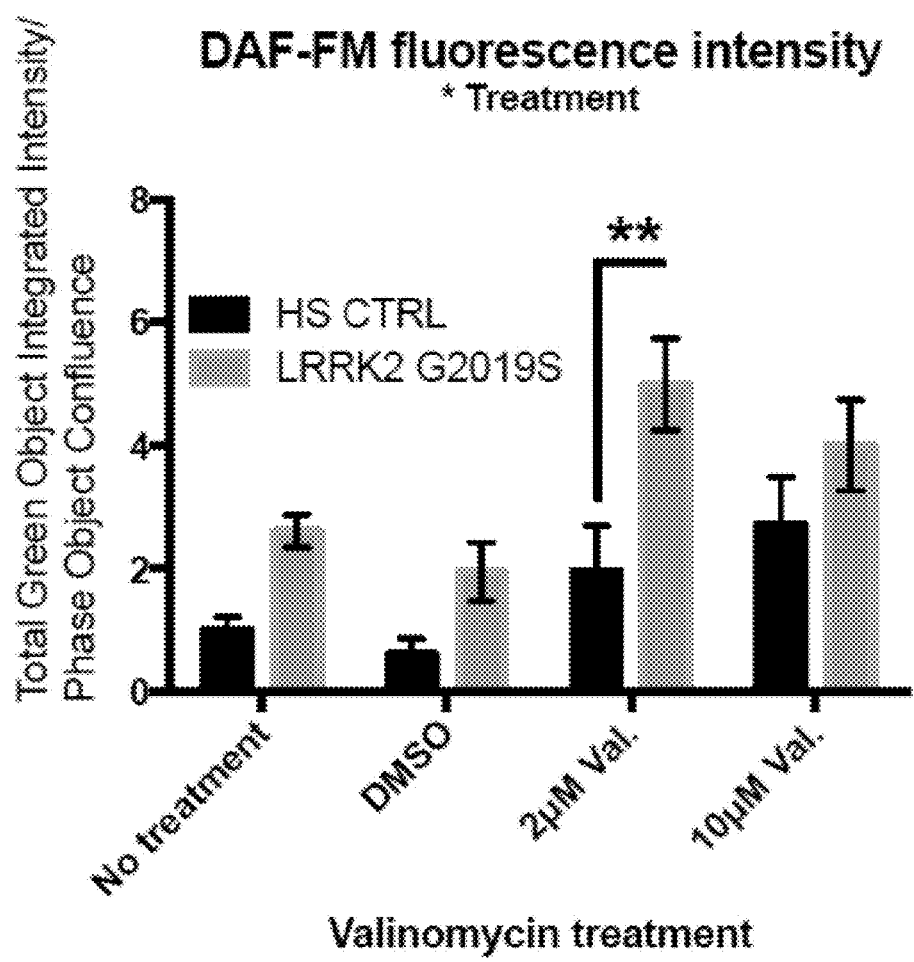
FIG. 8B shows the DAF-FM fluorescence intensity and the nitric oxide levels in LRRK2 G2019S iPS-derived neurons after valinomycin toxicity. Results demonstrate that an increase in RNS in LRRK2 G2019S neurons after mitochondrial depolarization induced through valinomycin toxicity.
Figure 10A:
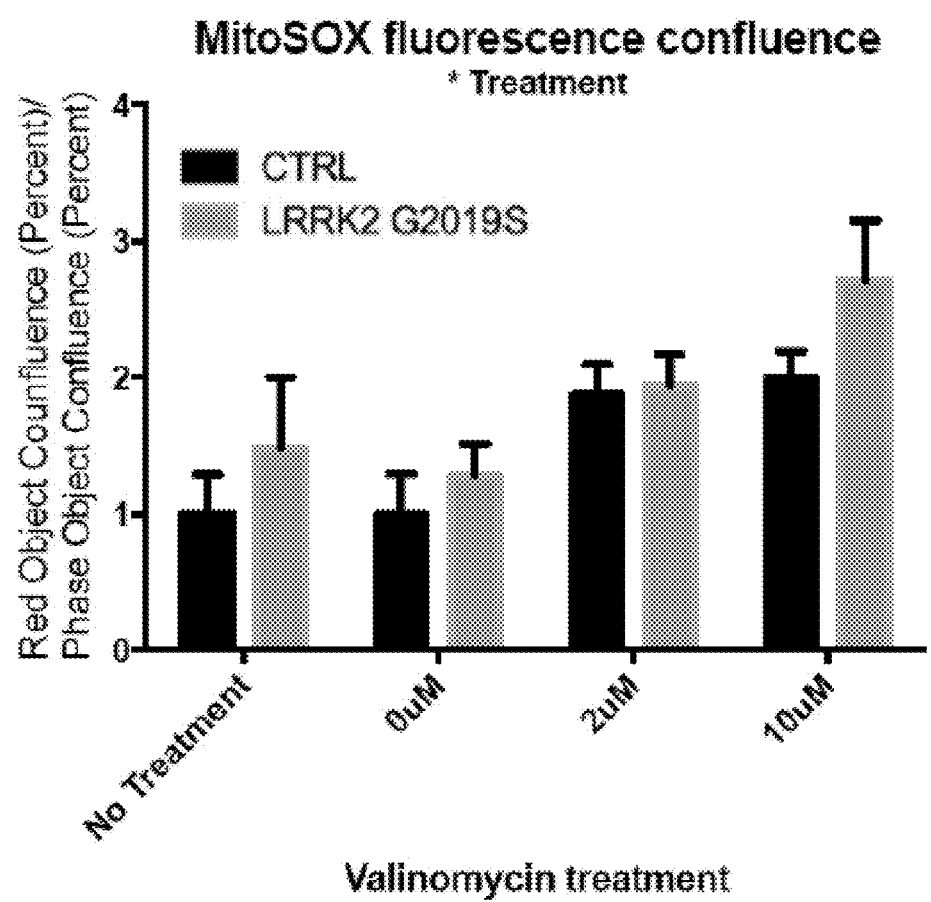
FIG. 10A shows the MitoSOX™ fluorescence confluence and that super oxide levels in LRRK2 G2019 iPS-derived neurons after valinomycin toxicity. Results demonstrate no difference in the ROS levels in LRRK2 G2019S neurons compared to the healthy subject neurons after mitochondrial depolarization induced through valinomycin toxicity.
Figure 10B:
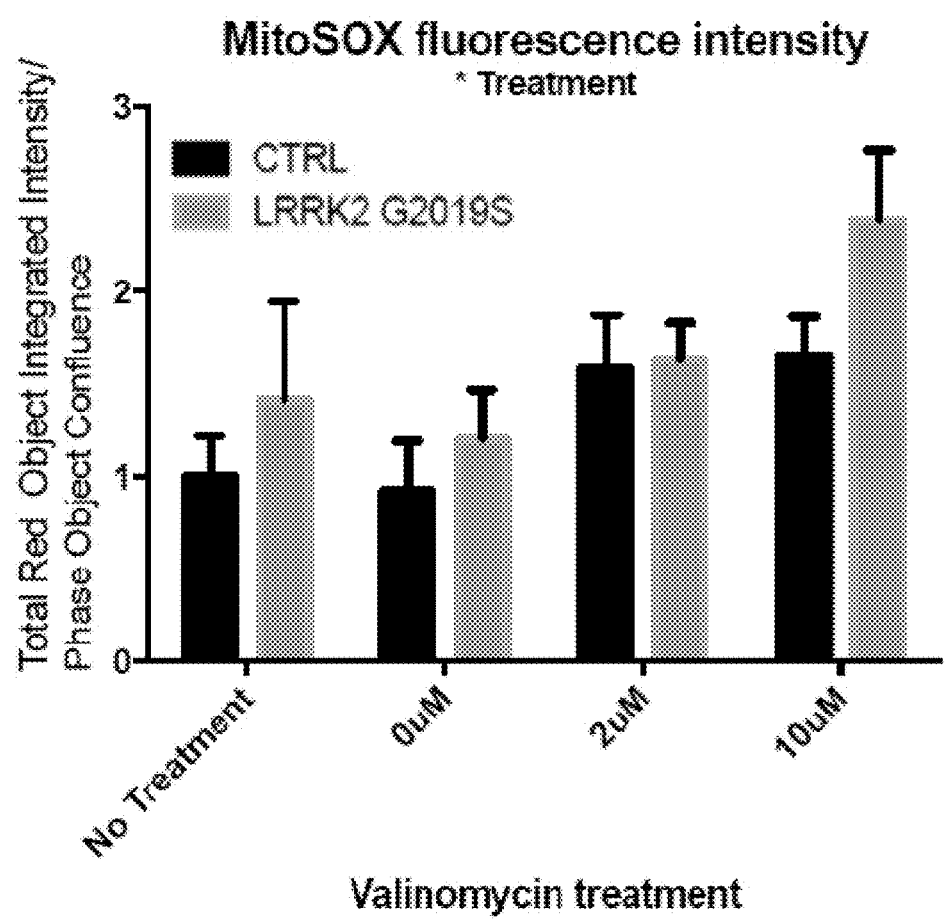
FIG. 10B shows the MitoSOX™ fluorescence intensity and that super oxide levels in LRRK2 G2019 iPS-derived neurons after valinomycin toxicity. Results demonstrate no difference in the ROS levels in LRRK2 G2019S neurons compared to the healthy subject neurons after mitochondrial depolarization induced through valinomycin toxicity.
Figure 11B:
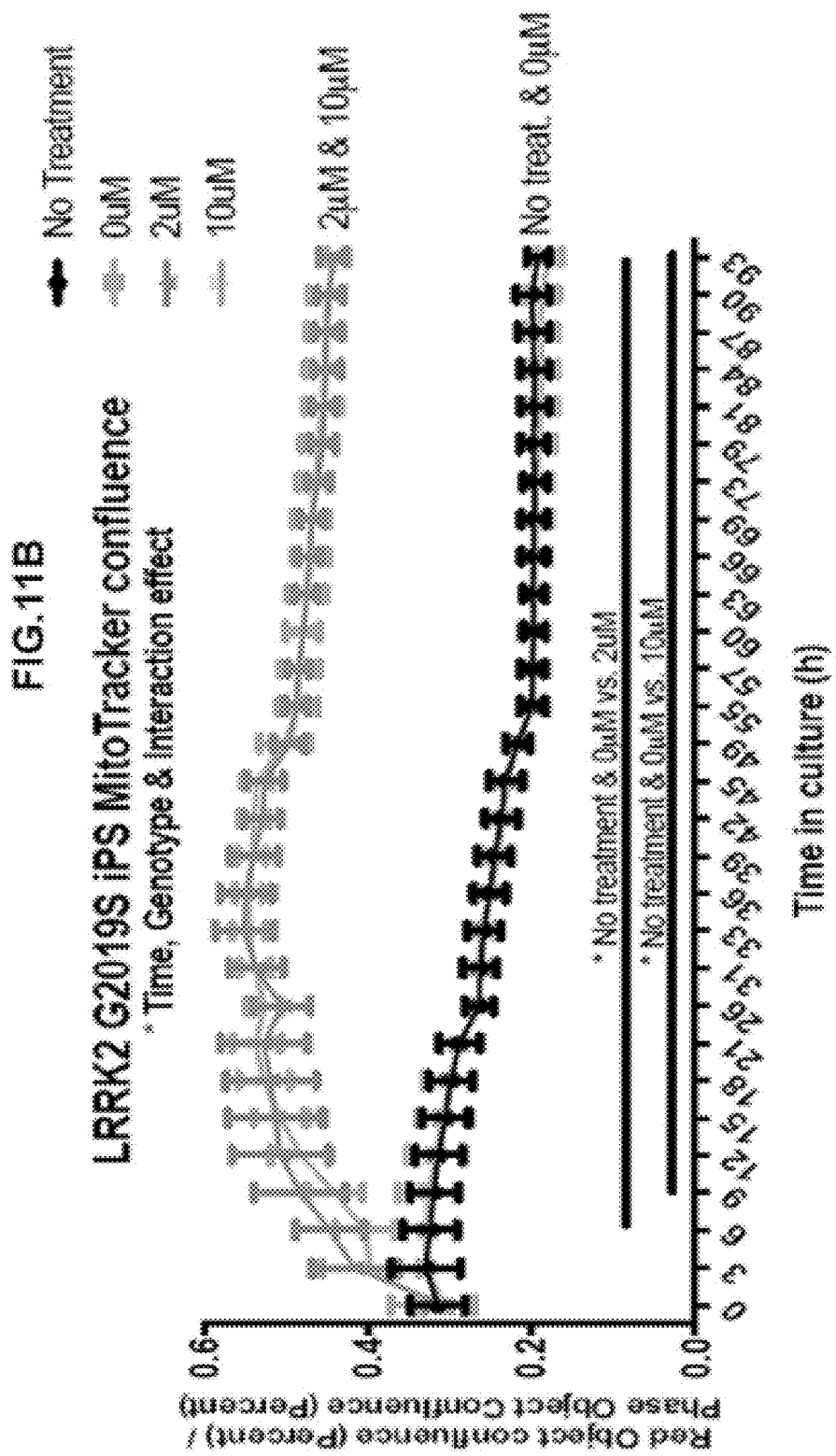
FIG. 11B shows the MitoTracker® confluence in iPS LRRK2 G2019S cells and that disruption of mitochondrial intracellular distribution in iPS-derived neurons after mitochondrial depolarization. Demonstrates altered mitochondrial intracellular distribution in LRRK2 G2019S iPS-derived neurons after mitochondrial depolarization.

Example 7: Exon 41 LRRK2 ASO Skipping and Nitric Oxide Levels in LRRK2 G2019S Neurons iPS-derived neurons carrying the LRRK2 G2019S mutation show a significant increase in nitric oxide levels after mitochondrial membrane depolarization induced by 24 hours low dose valinomycin treatment. FIG. 8C demonstrates that exon 41 LRRK2 ASO skipping appears to prevent an increase in nitric oxide levels in LRRK2 G2019S neurons following valinomycin treatment.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method of modulating splicing or expression of a LRRK2 transcript in a cell comprising contacting the cell with at least one compound comprising a modified oligonucleotide having 8 to 30 linked nucleosides and having a nucleobase sequence comprising a complementary region, wherein the complementary region comprises at least 8 contiguous nucleobases complementary to an equal-length portion of a target region of a Leucine-Rich-Repeat-Kinase (LRRK2) transcript, wherein the modified oligonucleotide has a nucleobase sequence as set forth in SEQ ID NO:1, SEQ ID NO:2, SEQ ID NO:6, SEQ ID NO:7, or SEQ ID NO:8.

2. The method of claim 1, wherein the cell is in vitro or in vivo.

3. The method of claim 1, wherein the cell is in vivo in an animal and the animal is a human.

4. The method of claim 3, wherein the modified oligonucleotide is administered to the human by intrathecal injection, intracerebroventricular injection, inhalation, parenteral injection or infusion, oral, subcutaneous or intramuscular injection, buccal, transdermal, transmucosal, or topical.

5. The method of claim 1, wherein the target region of the modified oligonucleotide comprises at least a portion of exon 2, exon 4, exon 31, or exon 41 of the LRRK2 transcript.

6. The method of claim 1, wherein the modified oligonucleotide comprises a nucleobase sequence having 20-30 linked nucleoside and having the nucleobase sequence as set forth in SEQ ID NO:9.

7. The method of claim 1, wherein the modified oligonucleotide comprises at least one modified nucleoside selected from a modified sugar moiety, a 2'-substituted sugar moiety, a 2'OME, a 2'F, a 2'-MOE, a bicyclic sugar moiety, a LNA, a cEt, a sugar surrogate, a morpholino, or a modified morpholino.

8. The method of claim 1, wherein the complementary region of the modified oligonucleotide comprises 10-25 contiguous nucleobases.

9. The method of claim 1, wherein the compound further comprises a pharmaceutically acceptable carrier or diluent.

10. The method of claim 4, wherein the modified oligonucleotide is administered by intrathecal injection or by intracerebroventricular injection.

11. The method of claim 1, wherein the modified oligonucleotide consists of the nucleobase sequence of SEQ ID NO:7.

12. The method of claim 7, wherein the modified nucleoside is a morpholino.

13. The method of claim 3, wherein the human has one or more symptoms associated with Parkinson's disease.

14. The method of claim 1, wherein the modified oligonucleotide consists of the nucleobase sequence of SEQ ID NO:6.

15. The method of claim 1, wherein the modified oligonucleotide consists of the nucleobase sequence of SEQ ID NO:8.

16. The method of claim 6, wherein the modified oligonucleotide consists of the nucleobase sequence of SEQ ID NO:9.

* * * * *

SEQUENCE LISTING

```
<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
ctaccagcct accatgttac cttga                                          25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
agacagacct gatcacctac ctggt                                          25

<210> SEQ ID NO 3
<211> LENGTH: 9239
<212> TYPE: DNA
<213> ORGANISM: Homo sapiens
```

<400> SEQUENCE: 3

```
gcgctggctg cgggcggtga gctgagctcg cccccgggga gctgtggccg gcgcccctgc    60
cggttccctg agcagcggac gttcatgctg ggagggcggc gggttggaag caggtgccac   120
catggctagt ggcagctgtc aggggtgcga agaggacgag gaaactctga agaagttgat   180
agtcaggctg aacaatgtcc aggaaggaaa acagatagaa acgctggtcc aaatcctgga   240
ggatctgctg gtgttcacgt actccgagca cgcctccaag ttatttcaag caaaaatat   300
ccatgtgcct ctgttgatcg tcttggactc ctatatgaga gtcgcgagtg tgcagcaggt   360
gggttggtca cttctgtgca aattaataga agtctgtcca ggtacaatgc aaagcttaat   420
gggaccccag gatgttggaa atgattggga agtccttggt gttcaccaat tgattcttaa   480
aatgctaaca gttcataatg ccagtgtaaa cttgtcagtg attggactga agaccttaga   540
tctcctccta acttcaggta aaatcacctt gctgatattg gatgaagaaa gtgatatttt   600
catgttaatt tttgatgcca tgcactcatt ccagccaat gatgaagtcc agaaacttgg   660
atgcaaagct ttacatgtgc tgtttgagag agtctcagag gagcaactga ctgaatttgt   720
tgagaacaaa gattatatga tattgttaag tgcgttaaca aattttaaag atgaagagga   780
aattgtgctt catgtgctgc attgtttaca ttccctagcg attccttgca ataatgtgga   840
agtcctcatg agtggcaatg tcaggtgtta atatttgtg gtggaagcta tgaaagcatt   900
ccctatgagt gaaagaattc aagaagtgag ttgctgtttg ctccataggc ttacattagg   960
taatttttc aatatcctgg tattaaacga agtccatgag tttgtggtga agctgtgca  1020
gcagtaccca gagaatgcag cattgcagat ctcagcgctc agctgtttgg ccctcctcac  1080
tgagactatt ttcttaaatc aagatttaga ggaaaagaat gagaatcaag agaatgatga  1140
tgagggggaa gaagataaat tgttttggct ggaagcctgt tacaaagcat taacgtggca  1200
tagaaagaac aagcacgtgc aggaggccgc atgctgggca ctaaataatc tccttatgta  1260
ccaaaacagt ttacatgaga agattggaga tgaagatggc catttcccag ctcataggga  1320
agtgatgctc tccatgctga tgcattcttc atcaaaggaa gttttccagg catctgcgaa  1380
tgcattgtca actctcttag aacaaaatgt taatttcaga aaaatactgt tatcaaaagg  1440
aatacacctg aatgttttgg agttaatgca gaagcatata cattctcctg aagtggctga  1500
aagtggctgt aaaatgctaa atcatctttt tgaaggaagc aacacttccc tggatataat  1560
ggcagcagtg gtccccaaaa tactaacagt tatgaaacgt catgagacat cattaccagt  1620
gcagctggag gcgcttcgag ctattttaca ttttatagtg cctggcatgc cagaagaatc  1680
cagggaggat acagaatttc atcataagct aaatatggtt aaaaaacagt gtttcaagaa  1740
tgatattcac aaactggtcc tagcagcttt gaacaggttc attggaaatc ctgggattca  1800
gaaatgtgga ttaaaagtaa tttcttctat tgtacatttt cctgatgcat tagagatgtt  1860
atccctggaa ggtgctatgg attcagtgct tcacacactg cagatgtatc cagatgacca  1920
agaaattcag tgtctgggtt taagtcttat aggatacttg attacaaaga gaatgtgtt  1980
cataggaact ggacatctgc tggcaaaaat tctggtttcc agcttatacc gatttaagga  2040
tgttgctgaa atacagacta aaggatttca gacaatctta gcaatcctca aattgtcagc  2100
atcttttcct aagctgctgg tgcatcattc atttgactta gtaatattcc atcaaatgtc  2160
ttccaatatc atggaacaaa aggatcaaca gtttctaaac ctctgttgca gtgttttgc   2220
aaaagtagct atggatgatt acttaaaaaa tgtgatgcta gagagagcgt gtgatcagaa  2280
```

```
taacagcatc atggttgaat gcttgcttct attgggagca gatgccaatc aagcaaagga    2340
gggatcttct ttaatttgtc aggtatgtga gaaagagagc agtcccaaat tggtggaact    2400
cttactgaat agtggatctc gtgaacaaga tgtacgaaaa gcgttgacga taagcattgg    2460
gaaaggtgac agccagatca tcagcttgct cttaaggagg ctggccctgg atgtggccaa    2520
caatagcatt tgccttggag gattttgtat aggaaaagtt gaaccttctt ggcttggtcc    2580
tttatttcca gataagactt ctaatttaag gaaacaaaca aatatagcat ctacactagc    2640
aagaatggtg atcagatatc agatgaaaag tgctgtggaa gaggaacag cctcaggcag     2700 cgatggaaat ttttctgaag atgtgctgtc taaatttgat gaatggacct ttattcctga    2760
ctcttctatg gacagtgtgt tgctcaaag tgatgacctg gatagtgaag gaagtgaagg     2820
ctcatttctt gtgaaaaaga aatctaattc aattagtgta ggagaatttt accgagatgc    2880
cgtattacag cgttgctcac caaatttgca aagacattcc aattccttgg ggcccatttt    2940
tgatcatgaa gatttactga agcgaaaaag aaaaatatta tcttcagatg attcactcag    3000
gtcatcaaaa cttcaatccc atatgaggca ttcagacagc atttcttctc tggcttctga    3060
gagagaatat attacatcac tagacctttc agcaaatgaa ctaagagata ttgatgccct    3120
aagccagaaa tgctgtataa gtgttcattt ggagcatctt gaaaagctgg agcttcacca    3180
gaatgcactc acgagctttc cacaacagct atgtgaaact ctgaagagtt tgacacattt    3240
ggacttgcac agtaataaat ttacatcatt tccttcttat ttgttgaaaa tgagttgtat    3300
tgctaatctt gatgtctctc gaaatgacat tggaccctca gtggttttag atcctacagt    3360
gaaatgtcca actctgaaac agtttaacct gtcatataac cagctgtctt ttgtacctga    3420
gaacctcact gatgtggtag agaaactgga gcagctcatt ttagaaggaa ataaaatatc    3480
agggatatgc tccccccttga gactgaagga actgaagatt taaacctta gtaagaacca    3540 catttcatcc ctatcagaga actttcttga ggcttgtcct aaagtggaga gtttcagtgc    3600
cagaatgaat tttcttgctg ctatgccttt cttgcctcct tctatgacaa tcctaaaatt    3660
atctcagaac aaattttcct gtattccaga agcaatttta aatcttccac acttgcggtc    3720
tttagatatg agcagcaatg atattcagta cctaccaggt cccgcacact ggaaatcttt    3780
gaacttaagg gaactcttat ttagccataa tcagatcagc atcttggact gagtgaaaa    3840 agcatattta tggtctagag tagagaaact gcatctttct cacaataaac tgaaagagat    3900
tcctcctgag attggctgtc ttgaaaatct gacatctctg gatgtcagtt acaacttgga    3960
actaagatcc tttcccaatg aaatgggga attaagcaaa atatgggatc ttcctttgga    4020
tgaactgcat cttaactttg attttaaaca tataggatgt aaagccaaag acatcataag    4080
gtttcttcaa cagcgattaa aaaaggctgt gccttataac cgaatgaaac ttatgattgt    4140
gggaaatact gggagtggta aaaccacctt attgcagcaa ttaatgaaaa ccaagaaatc    4200
agatcttgga atgcaaagtg ccacagttgg catagatgtg aaagactggc ctatccaaat    4260
aagagacaaa agaaagagag atctcgtcct aaatgtgtgg gattttgcag gtcgtgagga    4320
attctatagt actcatcccc attttatgac gcagcgagca ttgtaccttg ctgtctatga    4380
cctcagcaag ggacaggctg aagttgatgc catgaagcct tggctcttca atataaaggc    4440
tcgcgcttct tcttcccctg tgattctcgt tggcacacat ttggatgttt ctgatgagaa    4500
gcaacgcaaa gcctgcatga gtaaaatcac caaggaactc ctgaataagc gagggttccc    4560
tgccatacga gattaccact ttgtgaatgc caccgaggaa tctgatgctt ggcaaaact     4620 tcggaaaacc atcataaacg agagccttaa tttcaagatc cgagatcagc ttgttgttgg    4680
```

```
acagctgatt ccagactgct atgtagaact tgaaaaaatc attttatcgg agcgtaaaaa    4740
tgtgccaatt gaatttcccg taattgaccg gaaacgatta ttacaactag tgagagaaaa    4800
tcagctgcag ttagatgaaa atgagcttcc tcacgcagtt cactttctaa atgaatcagg    4860
agtccttctt cattttcaag acccagcact gcagttaagt gacttgtact ttgtggaacc    4920
caagtggctt tgtaaaatca tggcacagat tttgacagtg aaagtggaag gttgtccaaa    4980
acaccctaag ggcattattt cgcgtagaga tgtggaaaaa tttctttcaa aaaaaggaa     5040 atttccaaag aactacatgt cacagtattt taagctccta gaaaaattcc agattgcttt    5100
gccaatagga gaagaatatt tgctggttcc aagcagtttg tctgaccaca ggcctgtgat    5160
agagcttccc cattgtgaga actctgaaat tatcatccga ctatatgaaa tgccttattt    5220
tccaatggga ttttggtcaa gattaatcaa tcgattactt gagatttcac cttacatgct    5280
ttcagggaga gaacgagcac ttcgcccaaa cagaatgtat tggcgacaag gcatttactt    5340
aaattggtct cctgaagctt attgtctggt aggatctgaa gtcttagaca atcatccaga    5400
gagtttctta aaaattacag ttccttcttg tagaaaaggc tgtattcttt tgggccaagt    5460
tgtggaccac attgattctc tcatggaaga atggtttcct gggttgctgg agattgatat    5520
ttgtggtgaa ggagaaactc tgttgaagaa atgggcatta tatagtttta atgatggtga    5580
agaacatcaa aaaatcttac ttgatgactt gatgaagaaa gcagaggaag agatctctt    5640 agtaaatcca gatcaaccaa ggctcaccat tccaatatct cagattgccc ctgacttgat    5700
tttggctgac ctgcctagaa atattatgtt gaataatgat gagttggaat ttgaacaagc    5760
tccagagttt ctcctaggtg atggcagttt tggatcagtt taccgagcag cctatgaagg    5820
agaagaagtg gctgtgaaga ttttaataa acatacatca ctcaggctgt taagacaaga    5880
gcttgtggtg ctttgccacc tccaccaccc cagtttgata tctttgctgg cagctgggat    5940
tcgtccccgg atgttggtga tggagttagc ctccaagggt tccttggatc gcctgcttca    6000
gcaggacaaa gccagcctca ctagaaccct acagcacagg attgcactcc acgtagctga    6060
tggtttgaga tacctccact cagccatgat tatataccga gacctgaaac cccacaatgt    6120
gctgcttttc acactgtatc ccaatgctgc catcattgca aagattgctg actacggcat    6180
tgctcagtac tgctgtagaa tggggataaa aacatcagag ggcacaccag ggtttcgtgc    6240
acctgaagtt gccagaggaa atgtcattta taaccaacag gctgatgttt attcatttgg    6300
tttactactc tatgacattt tgacaactgg aggtagaata gtagagggtt tgaagttccc    6360
aaatgagttt gatgaattag aaatacaagg aaaattacct gatccagtta aagaatatgg    6420
ttgtgcccca tggcctatgg ttgagaaatt aattaaacag tgtttgaaag aaaatcctca    6480
agaaaggcct acttctgccc aggtctttga catttttgaat tcagctgaat tagtctgtct    6540
gacgagacgc attttattac ctaaaaacgt aattgttgaa tgcatggttg ctacacatca    6600
caacagcagg aatgcaagca tttggctggg ctgtgggcac accgacagag acagctctc    6660 atttcttgac ttaaatactg aaggatacac ttctgaggaa gttgctgata gtagaatatt    6720
gtgcttagcc ttggtgcatc ttcctgttga aaaggaaagc tggattgtgt ctgggacaca    6780
gtctggtact ctcctggtca tcaataccga agatgggaaa aagagacata ccctagaaaa    6840
gatgactgat tctgtcactt gtttgtattg caattccttt tccaagcaaa gcaaacaaaa    6900
aaattttctt ttggttggaa ccgctgatgg caagttagca attttgaag ataagactgt    6960 taagcttaaa ggagctgctc ctttgaagat actaaatata ggaaatgtca gtactccatt    7020
```

```
gatgtgtttg agtgaatcca caaattcaac ggaaagaaat gtaatgtggg gaggatgtgg      7080
cacaaagatt ttctcctttt ctaatgattt caccattcag aaactcattg agacaagaac      7140
aagccaactg ttttcttatg cagctttcag tgattccaac atcataacag tggtggtaga      7200
cactgctctc tatattgcta agcaaaatag ccctgttgtg gaagtgtggg ataagaaaac      7260
tgaaaaactc tgtggactaa tagactgcgt gcactttta agggaggtaa tggtaaaaga       7320
aaacaaggaa tcaaaacaca aaatgtctta ttctgggaga gtgaaaaccc tctgccttca      7380
gaagaacact gctctttgga taggaactgg aggaggccat attttactcc tggatctttc      7440
aactcgtcga cttatacgtg taatttacaa cttttgtaat tcggtcagag tcatgatgac      7500
agcacagcta ggaagcctta aaatgtcat gctggtattg ggctacaacc ggaaaaatac       7560
tgaaggtaca caaagcaga aagagataca atcttgcttg accgtttggg acatcaatct       7620
tccacatgaa gtgcaaaatt tagaaaaaca cattgaagtg agaaaagaat tagctgaaaa      7680
aatgagacga acatctgttg agtaagagag aaataggaat tgtctttgga taggaaaatt      7740
attctctcct cttgtaaata tttattttaa aaatgttcac atggaagggg tactcacatt      7800
ttttgaaata gctcgtgtgt atgaaggaat gttattattt taatttaaa tatatgtaaa       7860 aatacttacc agtaaatgtg tattttaaag aactatttaa aacacaatgt tatatttctt      7920
ataaatacca gttactttcg ttcattaatt aatgaaaata aatctgtgaa gtacctaatt      7980
taagtactca tactaaaatt tataaggccg ataatttttt gttttcttgt ctgtaatgga      8040
ggtaaacttt attttaaatt ctgtgcttaa gacaggacta ttgcttgtcg attttttctag     8100 aaatctgcac ggtataatga aaatattaag acagttccc atgtaatgta ttccttctta      8160
gattgcatcg aaatgcacta tcatatatgc ttgtaaatat tcaaatgaat ttgcactaat      8220
aaagtccttt gttggtatgt gaattctctt tgttgctgtt gcaaacagtg catcttacac      8280
aacttcactc aattcaaaag aaaactccat taaaagtact aatgaaaaaa catgacatac      8340
tgtcaaagtc ctcatatcta ggaaagacac agaaactctc tttgtcacag aaactctctg      8400
tgtctttcct agacataata gagttgtttt tcaactctat gtttgaatgt ggatacctg      8460 aattttgtat aattagtgta aatacagtgt tcagtcccttc aagtgatatt tttatttttt    8520
tattcatacc actagctact tgttttctaa tctgcttcat tctaatgctt atattcatct      8580
tttccctaaa tttgtgatgc tgcagatcct acatcattca gatagaaacc ttttttttt      8640 tcagaattat agaattccac agctcctacc aagaccatga ggataaatat ctaacacttt     8700
tcagttgctg aaggagaaag gagctttagt tatgatggat aaaaatatct gccaccctag      8760
gcttccaaat tatacttaaa ttgtttacat agcttaccac aataggagta tcagggccaa      8820 ataccatgt aataatttga ggtcatttct gcctttaggaa aagtactttc ggtaaattct      8880
ttggccctga ccagtattca ttatttcaga taattccctg tgataggaca actagtacat      8940
ttaatattct cagaacttat ggcatttac tatgtgaaaa cttaaatttt atttatatta       9000
agggtaatca aattcttaaa gatgaaagat ttctgtatt ttaaaggaag ctatgcttta       9060
acttgttatg taattaacaa aaaaatcata tataatagag ctctttgttc cagtgttatc      9120
tctttcattg ttactttgta tttgcaattt tttttaccaa agacaaatta aaaaaatgaa      9180
taccatattt aaatggaata ataaaggttt tttaaaaact ttaaaaaaaa aaaaaaaa       9239
```

<210> SEQ ID NO 4
<211> LENGTH: 2527
<212> TYPE: PRT
<213> ORGANISM: Homo sapiens

<400> SEQUENCE: 4

| | | | | | | | | | | | |
|---|---|---|---|---|---|---|---|---|---|---|---|
|Met|Ala|Ser|Gly|Ser|Cys|Gln|Gly|Cys|Glu|Glu|Asp|Glu|Glu|Thr|Leu
1| | | |5| | | | |10| | | | |15| |

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Leu Thr Asn Phe Lys Asp Glu Glu Ile Val Leu His
210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
        355                 360                 365

Ala Ala Cys Trp Ala Leu Asn Asn Leu Leu Met Tyr Gln Asn Ser Leu
370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln

```
                    405                 410                 415
Ala Ser Ala Asn Ala Leu Ser Thr Leu Leu Glu Gln Asn Val Asn Phe
                420                 425                 430

Arg Lys Ile Leu Leu Ser Lys Gly Ile His Leu Asn Val Leu Glu Leu
                435                 440                 445

Met Gln Lys His Ile His Ser Pro Glu Val Ala Glu Ser Gly Cys Lys
                450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
                500                 505                 510

Val Pro Gly Met Pro Glu Glu Ser Arg Glu Asp Thr Glu Phe His His
                515                 520                 525

Lys Leu Asn Met Val Lys Lys Gln Cys Phe Lys Asn Asp Ile His Lys
                530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
                580                 585                 590

Leu Gln Met Tyr Pro Asp Asp Gln Glu Ile Gln Cys Leu Gly Leu Ser
                595                 600                 605

Leu Ile Gly Tyr Leu Ile Thr Lys Lys Asn Val Phe Ile Gly Thr Gly
                610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
                660                 665                 670

Leu Val Ile Phe His Gln Met Ser Ser Asn Ile Met Glu Gln Lys Asp
                675                 680                 685

Gln Gln Phe Leu Asn Leu Cys Cys Lys Cys Phe Ala Lys Val Ala Met
                690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
                740                 745                 750

Ser Ser Pro Lys Leu Val Glu Leu Leu Asn Ser Gly Ser Arg Glu
                755                 760                 765

Gln Asp Val Arg Lys Ala Leu Thr Ile Ser Ile Gly Lys Gly Asp Ser
                770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
                820                 825                 830
```

```
Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
    850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Ser Asn Ser Ile Ser
                900                 905                 910

Val Gly Glu Phe Tyr Arg Asp Ala Val Leu Gln Arg Cys Ser Pro Asn
                915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
    980                 985                 990

Glu Leu Arg Asp Ile Asp Ala Leu Ser Gln Lys Cys Cys Ile Ser Val
                995                 1000                1005

His Leu Glu His Leu Glu Lys Leu Glu Leu His Gln Asn Ala Leu
    1010                1015                1020

Thr Ser Phe Pro Gln Gln Leu Cys Glu Thr Leu Lys Ser Leu Thr
    1025                1030                1035

His Leu Asp Leu His Ser Asn Lys Phe Thr Ser Phe Pro Ser Tyr
    1040                1045                1050

Leu Leu Lys Met Ser Cys Ile Ala Asn Leu Asp Val Ser Arg Asn
    1055                1060                1065

Asp Ile Gly Pro Ser Val Val Leu Asp Pro Thr Val Lys Cys Pro
    1070                1075                1080

Thr Leu Lys Gln Phe Asn Leu Ser Tyr Asn Gln Leu Ser Phe Val
    1085                1090                1095

Pro Glu Asn Leu Thr Asp Val Val Glu Lys Leu Glu Gln Leu Ile
    1100                1105                1110

Leu Glu Gly Asn Lys Ile Ser Gly Ile Cys Ser Pro Leu Arg Leu
    1115                1120                1125

Lys Glu Leu Lys Ile Leu Asn Leu Ser Lys Asn His Ile Ser Ser
    1130                1135                1140

Leu Ser Glu Asn Phe Leu Glu Ala Cys Pro Lys Val Glu Ser Phe
    1145                1150                1155

Ser Ala Arg Met Asn Phe Leu Ala Ala Met Pro Phe Leu Pro Pro
    1160                1165                1170

Ser Met Thr Ile Leu Lys Leu Ser Gln Asn Lys Phe Ser Cys Ile
    1175                1180                1185

Pro Glu Ala Ile Leu Asn Leu Pro His Leu Arg Ser Leu Asp Met
    1190                1195                1200

Ser Ser Asn Asp Ile Gln Tyr Leu Pro Gly Pro Ala His Trp Lys
    1205                1210                1215

Ser Leu Asn Leu Arg Glu Leu Leu Phe Ser His Asn Gln Ile Ser
    1220                1225                1230
```

```
Ile Leu Asp Leu Ser Glu Lys Ala Tyr Leu Trp Ser Arg Val Glu
1235                1240                1245

Lys Leu His Leu Ser His Asn Lys Leu Lys Glu Ile Pro Pro Glu
1250                1255                1260

Ile Gly Cys Leu Glu Asn Leu Thr Ser Leu Asp Val Ser Tyr Asn
1265                1270                1275

Leu Glu Leu Arg Ser Phe Pro Asn Glu Met Gly Lys Leu Ser Lys
1280                1285                1290

Ile Trp Asp Leu Pro Leu Asp Glu Leu His Leu Asn Phe Asp Phe
1295                1300                1305

Lys His Ile Gly Cys Lys Ala Lys Asp Ile Ile Arg Phe Leu Gln
1310                1315                1320

Gln Arg Leu Lys Lys Ala Val Pro Tyr Asn Arg Met Lys Leu Met
1325                1330                1335

Ile Val Gly Asn Thr Gly Ser Gly Lys Thr Thr Leu Leu Gln Gln
1340                1345                1350

Leu Met Lys Thr Lys Lys Ser Asp Leu Gly Met Gln Ser Ala Thr
1355                1360                1365

Val Gly Ile Asp Val Lys Asp Trp Pro Ile Gln Ile Arg Asp Lys
1370                1375                1380

Arg Lys Arg Asp Leu Val Leu Asn Val Trp Asp Phe Ala Gly Arg
1385                1390                1395

Glu Glu Phe Tyr Ser Thr His Pro His Phe Met Thr Gln Arg Ala
1400                1405                1410

Leu Tyr Leu Ala Val Tyr Asp Leu Ser Lys Gly Gln Ala Glu Val
1415                1420                1425

Asp Ala Met Lys Pro Trp Leu Phe Asn Ile Lys Ala Arg Ala Ser
1430                1435                1440

Ser Ser Pro Val Ile Leu Val Gly Thr His Leu Asp Val Ser Asp
1445                1450                1455

Glu Lys Gln Arg Lys Ala Cys Met Ser Lys Ile Thr Lys Glu Leu
1460                1465                1470

Leu Asn Lys Arg Gly Phe Pro Ala Ile Arg Asp Tyr His Phe Val
1475                1480                1485

Asn Ala Thr Glu Glu Ser Asp Ala Leu Ala Lys Leu Arg Lys Thr
1490                1495                1500

Ile Ile Asn Glu Ser Leu Asn Phe Lys Ile Arg Asp Gln Leu Val
1505                1510                1515

Val Gly Gln Leu Ile Pro Asp Cys Tyr Val Glu Leu Glu Lys Ile
1520                1525                1530

Ile Leu Ser Glu Arg Lys Asn Val Pro Ile Glu Phe Pro Val Ile
1535                1540                1545

Asp Arg Lys Arg Leu Leu Gln Leu Val Arg Glu Asn Gln Leu Gln
1550                1555                1560

Leu Asp Glu Asn Glu Leu Pro His Ala Val His Phe Leu Asn Glu
1565                1570                1575

Ser Gly Val Leu Leu His Phe Gln Asp Pro Ala Leu Gln Leu Ser
1580                1585                1590

Asp Leu Tyr Phe Val Glu Pro Lys Trp Leu Cys Lys Ile Met Ala
1595                1600                1605

Gln Ile Leu Thr Val Lys Val Glu Gly Cys Pro Lys His Pro Lys
1610                1615                1620

Gly Ile Ile Ser Arg Arg Asp Val Glu Lys Phe Leu Ser Lys Lys
```

```
              1625                1630                1635

Arg Lys Phe Pro Lys Asn Tyr Met Ser Gln Tyr Phe Lys Leu Leu
        1640                1645                1650

Glu Lys Phe Gln Ile Ala Leu Pro Ile Gly Glu Glu Tyr Leu Leu
        1655                1660                1665

Val Pro Ser Ser Leu Ser Asp His Arg Pro Val Ile Glu Leu Pro
        1670                1675                1680

His Cys Glu Asn Ser Glu Ile Ile Ile Arg Leu Tyr Glu Met Pro
        1685                1690                1695

Tyr Phe Pro Met Gly Phe Trp Ser Arg Leu Ile Asn Arg Leu Leu
        1700                1705                1710

Glu Ile Ser Pro Tyr Met Leu Ser Gly Arg Glu Arg Ala Leu Arg
        1715                1720                1725

Pro Asn Arg Met Tyr Trp Arg Gln Gly Ile Tyr Leu Asn Trp Ser
        1730                1735                1740

Pro Glu Ala Tyr Cys Leu Val Gly Ser Glu Val Leu Asp Asn His
        1745                1750                1755

Pro Glu Ser Phe Leu Lys Ile Thr Val Pro Ser Cys Arg Lys Gly
        1760                1765                1770

Cys Ile Leu Leu Gly Gln Val Val Asp His Ile Asp Ser Leu Met
        1775                1780                1785

Glu Glu Trp Phe Pro Gly Leu Leu Glu Ile Asp Ile Cys Gly Glu
        1790                1795                1800

Gly Glu Thr Leu Leu Lys Lys Trp Ala Leu Tyr Ser Phe Asn Asp
        1805                1810                1815

Gly Glu Glu His Gln Lys Ile Leu Leu Asp Asp Leu Met Lys Lys
        1820                1825                1830

Ala Glu Glu Gly Asp Leu Leu Val Asn Pro Asp Gln Pro Arg Leu
        1835                1840                1845

Thr Ile Pro Ile Ser Gln Ile Ala Pro Asp Leu Ile Leu Ala Asp
        1850                1855                1860

Leu Pro Arg Asn Ile Met Leu Asn Asn Asp Glu Leu Glu Phe Glu
        1865                1870                1875

Gln Ala Pro Glu Phe Leu Leu Gly Asp Gly Ser Phe Gly Ser Val
        1880                1885                1890

Tyr Arg Ala Ala Tyr Glu Gly Glu Glu Val Ala Val Lys Ile Phe
        1895                1900                1905

Asn Lys His Thr Ser Leu Arg Leu Leu Arg Gln Glu Leu Val Val
        1910                1915                1920

Leu Cys His Leu His His Pro Ser Leu Ile Ser Leu Leu Ala Ala
        1925                1930                1935

Gly Ile Arg Pro Arg Met Leu Val Met Glu Leu Ala Ser Lys Gly
        1940                1945                1950

Ser Leu Asp Arg Leu Leu Gln Gln Asp Lys Ala Ser Leu Thr Arg
        1955                1960                1965

Thr Leu Gln His Arg Ile Ala Leu His Val Ala Asp Gly Leu Arg
        1970                1975                1980

Tyr Leu His Ser Ala Met Ile Ile Tyr Arg Asp Leu Lys Pro His
        1985                1990                1995

Asn Val Leu Leu Phe Thr Leu Tyr Pro Asn Ala Ala Ile Ile Ala
        2000                2005                2010

Lys Ile Ala Asp Tyr Gly Ile Ala Gln Tyr Cys Cys Arg Met Gly
        2015                2020                2025
```

-continued

```
Ile Lys Thr Ser Glu Gly Thr Pro Gly Phe Arg Ala Pro Glu Val
    2030                2035                2040

Ala Arg Gly Asn Val Ile Tyr Asn Gln Gln Ala Asp Val Tyr Ser
    2045                2050                2055

Phe Gly Leu Leu Leu Tyr Asp Ile Leu Thr Thr Gly Gly Arg Ile
    2060                2065                2070

Val Glu Gly Leu Lys Phe Pro Asn Glu Phe Asp Glu Leu Glu Ile
    2075                2080                2085

Gln Gly Lys Leu Pro Asp Pro Val Lys Glu Tyr Gly Cys Ala Pro
    2090                2095                2100

Trp Pro Met Val Glu Lys Leu Ile Lys Gln Cys Leu Lys Glu Asn
    2105                2110                2115

Pro Gln Glu Arg Pro Thr Ser Ala Gln Val Phe Asp Ile Leu Asn
    2120                2125                2130

Ser Ala Glu Leu Val Cys Leu Thr Arg Arg Ile Leu Leu Pro Lys
    2135                2140                2145

Asn Val Ile Val Glu Cys Met Val Ala Thr His His Asn Ser Arg
    2150                2155                2160

Asn Ala Ser Ile Trp Leu Gly Cys Gly His Thr Asp Arg Gly Gln
    2165                2170                2175

Leu Ser Phe Leu Asp Leu Asn Thr Glu Gly Tyr Thr Ser Glu Glu
    2180                2185                2190

Val Ala Asp Ser Arg Ile Leu Cys Leu Ala Leu Val His Leu Pro
    2195                2200                2205

Val Glu Lys Glu Ser Trp Ile Val Ser Gly Thr Gln Ser Gly Thr
    2210                2215                2220

Leu Leu Val Ile Asn Thr Glu Asp Gly Lys Lys Arg His Thr Leu
    2225                2230                2235

Glu Lys Met Thr Asp Ser Val Thr Cys Leu Tyr Cys Asn Ser Phe
    2240                2245                2250

Ser Lys Gln Ser Lys Gln Lys Asn Phe Leu Leu Val Gly Thr Ala
    2255                2260                2265

Asp Gly Lys Leu Ala Ile Phe Glu Asp Lys Thr Val Lys Leu Lys
    2270                2275                2280

Gly Ala Ala Pro Leu Lys Ile Leu Asn Ile Gly Asn Val Ser Thr
    2285                2290                2295

Pro Leu Met Cys Leu Ser Glu Ser Thr Asn Ser Thr Glu Arg Asn
    2300                2305                2310

Val Met Trp Gly Gly Cys Gly Thr Lys Ile Phe Ser Phe Ser Asn
    2315                2320                2325

Asp Phe Thr Ile Gln Lys Leu Ile Glu Thr Arg Thr Ser Gln Leu
    2330                2335                2340

Phe Ser Tyr Ala Ala Phe Ser Asp Ser Asn Ile Ile Thr Val Val
    2345                2350                2355

Val Asp Thr Ala Leu Tyr Ile Ala Lys Gln Asn Ser Pro Val Val
    2360                2365                2370

Glu Val Trp Asp Lys Lys Thr Glu Lys Leu Cys Gly Leu Ile Asp
    2375                2380                2385

Cys Val His Phe Leu Arg Glu Val Met Val Lys Glu Asn Lys Glu
    2390                2395                2400

Ser Lys His Lys Met Ser Tyr Ser Gly Arg Val Lys Thr Leu Cys
    2405                2410                2415
```

-continued

| | | | | | | | | | | |
|---|---|---|---|---|---|---|---|---|---|---|
| Leu | Gln | Lys | Asn | Thr | Ala | Leu | Trp | Ile | Gly | Thr | Gly | Gly | His |
| | 2420 | | | | 2425 | | | | 2430 | | | | |
| Ile | Leu | Leu | Leu | Asp | Leu | Ser | Thr | Arg | Arg | Leu | Ile | Arg | Val | Ile |
| 2435 | | | | | 2440 | | | | 2445 | | | | | |
| Tyr | Asn | Phe | Cys | Asn | Ser | Val | Arg | Val | Met | Met | Thr | Ala | Gln | Leu |
| | 2450 | | | | 2455 | | | | 2460 | | | | | |
| Gly | Ser | Leu | Lys | Asn | Val | Met | Leu | Val | Leu | Gly | Tyr | Asn | Arg | Lys |
| 2465 | | | | | 2470 | | | | 2475 | | | | | |
| Asn | Thr | Glu | Gly | Thr | Gln | Lys | Gln | Lys | Glu | Ile | Gln | Ser | Cys | Leu |
| | 2480 | | | | 2485 | | | | 2490 | | | | | |
| Thr | Val | Trp | Asp | Ile | Asn | Leu | Pro | His | Glu | Val | Gln | Asn | Leu | Glu |
| | 2495 | | | | 2500 | | | | 2505 | | | | | |
| Lys | His | Ile | Glu | Val | Arg | Lys | Glu | Leu | Ala | Glu | Lys | Met | Arg | Arg |
| 2510 | | | | | 2515 | | | | 2520 | | | | | |
| Thr | Ser | Val | Glu |
| 2525 | | | |

```
<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
cctcttacct cagttacaat ttata                                                25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
atacacatat tacctgaagt tagga                                                25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
agtgaaaaca atgcctttac ctgct                                                25

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
ggtatctgcc agaaaatgca cagga                                                25

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 9
aatgctgtag tcagcaatct ttgca                                              25
```